US008008007B2

(12) United States Patent (10) Patent No.: US 8,008,007 B2
Weinhold et al. (45) Date of Patent: Aug. 30, 2011

(54) S-ADENOSYL-L-METHIONINE ANALOGS WITH EXTENDED ACTIVATED GROUPS FOR TRANSFER BY METHYLTRANSFERASES

(75) Inventors: Elmar Weinhold, Aachen (DE); Christian Dalhoff, Berlin (DE); Saulius Klimasauskas, Vilnius (LT); Grazvydas Lukinavicius, Vilnius (LT)

(73) Assignee: RWTH Aachen, Aachen (DE)

( * ) Notice: Subject to any disclaimer, the term of this patent is extended or adjusted under 35 U.S.C. 154(b) by 408 days.

(21) Appl. No.: 11/871,016

(22) Filed: Oct. 11, 2007

(65) Prior Publication Data

US 2009/0018101 A1 Jan. 15, 2009

Related U.S. Application Data

(63) Continuation of application No. PCT/EP2006/003463, filed on Apr. 13, 2006.

(30) Foreign Application Priority Data

Apr. 14, 2005 (EP) ..................................... 05008226

(51) Int. Cl.
*C12Q 1/68* (2006.01)
*C07H 19/167* (2006.01)
*C12P 19/40* (2006.01)
(52) U.S. Cl. ............................ 435/6; 435/88; 536/27.31
(58) Field of Classification Search .................. None
See application file for complete search history.

(56) References Cited

U.S. PATENT DOCUMENTS

2007/0264667 A1* 11/2007 Gellibolian et al. ............ 435/7.1
2009/0018101 A1 1/2009 Weinhold et al.

FOREIGN PATENT DOCUMENTS

WO 88/10315 A1 12/1988
WO 89/09622 A1 10/1989

OTHER PUBLICATIONS

Brada et al., Early Alteration in Liver of Rats Fed 2-Fluorenylacetamide Investigated by L-Ethionine Probe, Chemico-Biological Interactions, 66(3-4), 287-295 (1988): in Search Notes (SRNT), see CAPLUS Answer 4 of 8.*
International Search Report, PCT/EP2006/003463, Oct. 27, 2006.
Pljevaljcic et al., "Design of a New Fluorescent Cofactor for DNA Methyltransferases and Sequence-Specific Labeling of DNA," J. Am. Chem. Soc. 125, (2003) pp. 3486-3492.
Pljevaljcic et al., "Sequence-Specific DNA Labeling U sing Methyltransferases," Methods Mol. Biol. 283, (2004) pp. 145-161.
De La Haba et al., "S-Adenosylmethionine: The Relation of Configuration at the Sulfonium Center to Enzymatic Reactivity," J. Am. Chem. Soc., (1959) vol. 81, pp. 3975-3980.
Stecher et al., "Biocatalytic Friedel-Crafts Alkylation using Non-natural Cofactors," Angew. Chem. Int. Ed. 2009, 48, pp. 9546-9548.
Pljevaljcic et al., "Sequence-specific Methyltransferase-induced Labeling of DNA (SMILing DNA)," ChemBioChem 2004, 5, pp. 265-269.
Schlenk et al., "The S-n-Propyl Analogue of S-Adenosylmethionine," Biochimica et Biophysica Acta, 385 (1975) pp. 312-323.
Schlenk, F., "Recent Studies of the Chemical Properties of Adenosylmethionine and Related Compounds," Biochem, 1977, pp. 3-17.
Liu et al., "Peptide segment ligation strategy without use of protecting groups," Proc. Natl. Acad. Sci, USA, Jul. 1994, vol. 91, pp. 6584-6588.
Dawson et al., "Synthesis of Proteins by Native Chemical Ligation," Science, Nov. 4, 1994, vol. 266, pp. 776-779.
Lewis et al., "Click Chemistry In Situ: Acetylcholinesterase as a Reaction Vessel for the Selective Assembly of a Femtomolar Inhibitor from an Array of Building Blocks," Angew. Chem. Int. Ed., 2002, 41, No. 6, pp. 1053-1057.
Saxon et al., "Cell Surface Engineering by a Modified Staudinger Reaction," Science, Mar. 17, 2000, vol. 287, pp. 2007-2010.
Casalnuovo et al., "Palladium-Catalyzed Alkylations in Aqueous Media," J. Am. Chem. Soc. 1990, 112, pp. 4324-4330.
Dibowski et al., "Bioconjugation of Peptides by Palladium-Catalyzed C-C Cross Coupling in Water," Angew Chem. Int. Ed. 1998, 37, No. 4, pp. 476-478.
Bong et al., "Chemoselective Pd(0)-Catalyzed Peptide Coupling in Water," Organic Letters, 2001, vol. 3, No. 16, pp. 2509-2511.
Devasher et al., "Aqueous-Phase, Palladium-Catalyzed Cross-Coupling of Aryl Bromides under Milder Conditions, Using Water-Soluble, Sterically Demanding Alkylphosphines," J. Org. Chem. 2004, 69, pp. 7919-7927.
Porath et al., "Metal chelate affinity chromatography, a new approach to protein fractionation," Nature, Dec. 18, 1975, vol. 258, pp. 598-599.

(Continued)

*Primary Examiner* — Lawrence E Crane
(74) *Attorney, Agent, or Firm* — Baker Donelson Bearman, Caldwell & Berkowitz, P.C.

(57) ABSTRACT

S-Adenosyl-L-methionine analogs of formula (I):

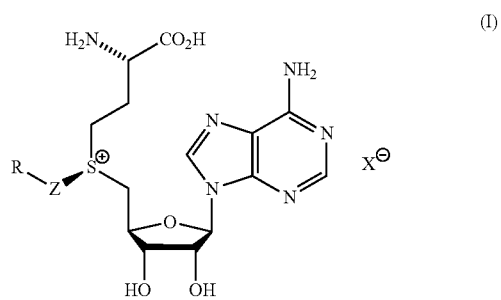

are disclosed wherein R comprises a carbon-carbon double bond, carbon-sulfur double bond, carbon-nitrogen double bond, -a carbon-carbon triple bond, carbon-nitrogen triple bond or an aromatic carbocyclic or heterocyclic system in β-position to the sulfonium center, $X^{\ominus}$ is an organic or inorganic anion carrying one or more negative charges, Z is —$CR^1R^2$—, —O—, —S— or —$NR^3$— and $R^1$, $R^2$ and $R^3$ are independently selected from H, D and $C_1$—C alkyl; as well as complexes with a methyltransferase, pharmaceutical compositions, methods for modifying a biomolecule, and methods for detecting sequences specific methylation of biomolecules.

31 Claims, 12 Drawing Sheets

OTHER PUBLICATIONS

Porath J., "Immobilized Metal Ion Affinity Chromatography," Protein Expression and Purification 3, (1992), pp. 263-281.

Hemdan et al., "Development of Immobilized Metal Affinity Chromatography: II. Interaction of Amino Acids with Immobilized Nickel Iminodiacetate," Journal of Chromatography, 323 (1985) pp. 255-264.

Porath et al., "Cascade-mode multiaffinity chromatography: Fractionation of human serum proteins," Journal of Chromatography, 550 (1991) pp. 751-764.

Schmidt et al., "The random peptide library-assisted engineering of a C-terminal affinity peptide, useful for the detection and purification of a functional Ig Fv fragment," Protein Engineering, vol. 6, No. 1, 1993, pp. 109-122.

Kagan et al., "Widespread Occurrence of Three Sequence Motifs in Diverse S-Adenosylmethionine-Dependent Methyltransferases Suggests a Common Structure for These Enzymes," Archives of Biochemistry and Biophysics, vol. 310, No. 2, May 1, 1994, pp. 417-427.

Walker et al., "Strand displacement amplification-an isothermal, in vitro DNA amplification technique," Nucleic Acids Research, vol. 20, No. 7, 1992, pp. 1691-1696.

Galfre et al., "Preparation of Monoclonal Antibodies: Strategies and Procedures," Methods in Enzymology, vol. 73, pp. 3-46, (1981).

Schier et al., "Efficient in vitro affinity maturation of phage antibodies using BIAcore guided selections," Hum. Antibod. Hybridomas, 1996, vol. 7, 3, pp. 97-105.

Malmborg et al., "BIAcore as a tool in antibody engineering," Journal of Immunological Methods, 183 (1995), pp. 7-13.

Ross et al., "A straightforward preparation of primary alkyl triflates and their utility in the synthesis of derivatives of ethidium," J. Chem. Soc., Perkin Trans. 1, 2000, pp. 571-574.

Kumar et al., "DNA containing 4'-thio-2'-deoxycytidine inhibits methylation by HhaI methyltransferase," Nucleic Acids Research, 1997, vol. 25, No. 14, pp. 2773-2783.

Kunkel T., "Rapid and efficient site-specific mutagenesis without phenotypic selection," Proc. Natl. Acad. Sci. USA, vol. 82, Jan. 1985, pp. 488-492.

Kumar et al., "Purification, Crystallization, and Preliminary X-ray Diffraction Analysis of M.HhaI-AdoMet Complex," Biochemistry 1992, 31, pp. 8648-8653.

Klimasauskas et al., "Dynamic modes of the flipped-out cytosine during HhaI methyltransferase-DNA interactions in solution," The EMBO Journal, vol. 17, No. 1, 1998, pp. 317-324.

Labahn et al., "Three-dimensional structure of the adenine-specific DNA methyltransferase M-Tag I in complex with the cofactor S-adenosylmethionine," Proc. Natl. Acad. Sci. USA, vol. 91, Nov. 1994, pp. 10957-10961.

Kwoh et al., "Transcription-based amplification system and detection of amplified human immunodeficiency virus type 1 with a bead-based sandwich hybridization format," Proc. Natl. Acad. Sci. USA, Feb. 1989, vol. 86, pp. 1173-1177.

Kohler et al., "Continuous cultures of fused cells secreting antibody of predefined specificity," Nature (1975) vol. 256, pp. 495-497.

Ho et al., "Site-directed mutagenesis by overlap extension using the polymerase chain reaction," Gene 77, (1989) pp. 51-59.

Holz et al., "2-Aminopurine as a fluorescent probe for DNA base flipping by methyltransfeerases," Nucleic Acids Res. 26, (1998) pp. 1076-1083.

Goedecke et al., "Structure of the N6-adenine DNA methyltransferase M-TagI in complex with DNA and a cofactor analog," Nature Struct. Biol. 8, (2001) pp. 121-125.

Koudan et al., "Homology Modelling of the CG-specific DNA Methyltransferase SssI and its Complexes with DNA and AdoHcy," J. Biomol Struct. Dyn. 22, (2004) pp. 339-346.

Thomson et al., "Efficient Route to the Pineal Hormone Melatonin by Radical-Based Indole Synthesis," Synth. Commun. 33, (2003) pp. 3631-3641.

Sambrook et al., "Rapid and Efficient Site-directed Mutagenesis by the Single-tube Megaprimer PCR Method,"(2001) Cold Spring Harbor Laboratory Press, pp. 13.31-13.35.

Jeltsch A, "Beyond Watson and Crick: DNA Methylation and Molecular Enzymology of DNA Methyltransferases," ChemBioChem 3, (2002) pp. 275-293.

Cheng X, "Structure and Funtion of DNA Methyltransferases," Annu. Rev. Biophys. Biomol. Struct. 24, (1995) pp. 293-318.

Bird A, "DNA methylation patterns and epigenetic memory," Genes Dev. 16, (2002), pp. 6-21.

Feil et al., "Genomic imprinting in mammals: an interplay between chromatin and DNA methylation?," Trends Genet. 15, (1999), pp. 431-435.

Panning et al., "RNA and the Epigenetic Regulation of X Chromosome Inactivation," Cell 93, (1998), pp. 305-308.

Yoder et al., "Cyrosine methylation and the ecology of intragenomic parasites," Trends Genet. 13, (1997), pp. 335-340.

Baylin et al., "Alternations in DNA Methylation: A Fundamental Aspect of Neoplasia," Adv. Cancer Res. 72, (1998), pp. 141-196.

Jones et al., "Cancer epigenetics comes of age," Nat. Genet. 21, (1999) pp. 163-167.

Graham et al., "Internal labeling of oligonucleotide probes by Diels-Alder cycloaddition," Tetrahedron Letters 43 (2002), pp. 4785-4788.

* cited by examiner

Figure 4A
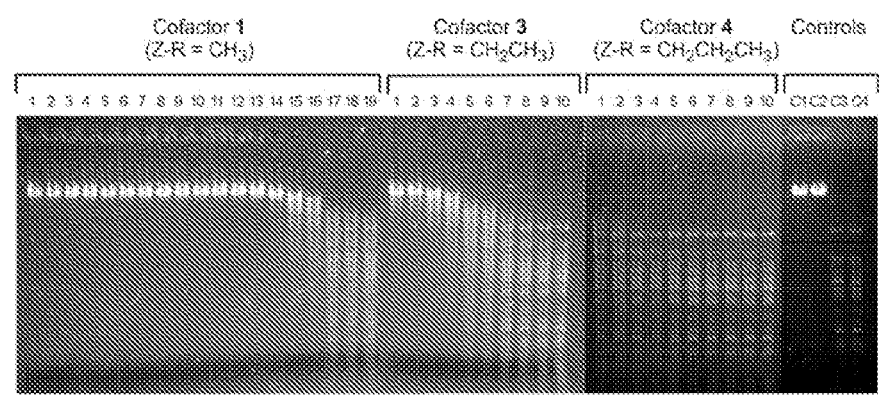
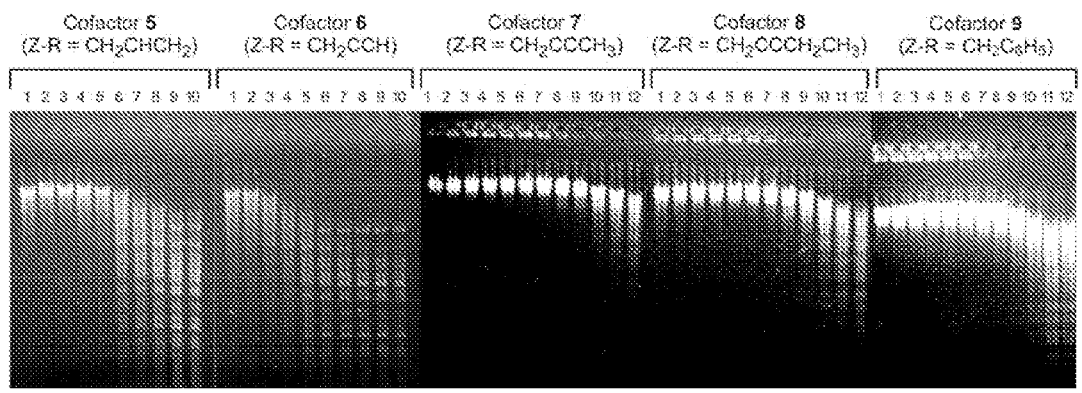
Figure 4B

Figure 5A
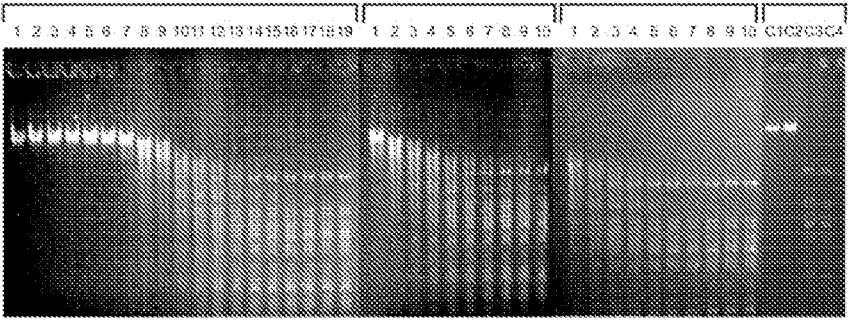
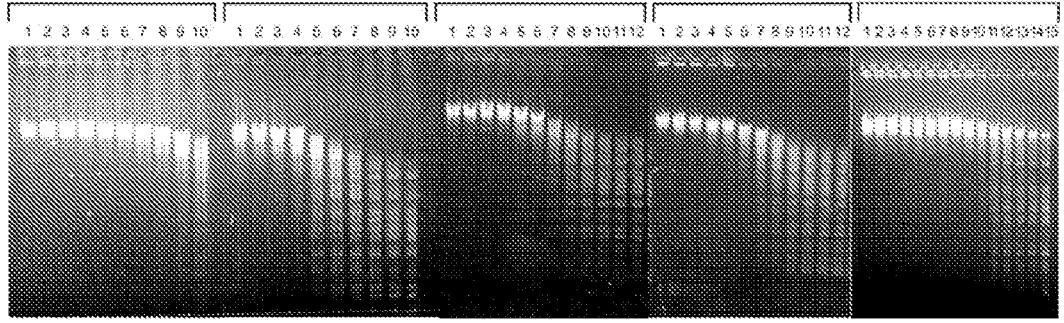
Figure 5B

Figure 6A
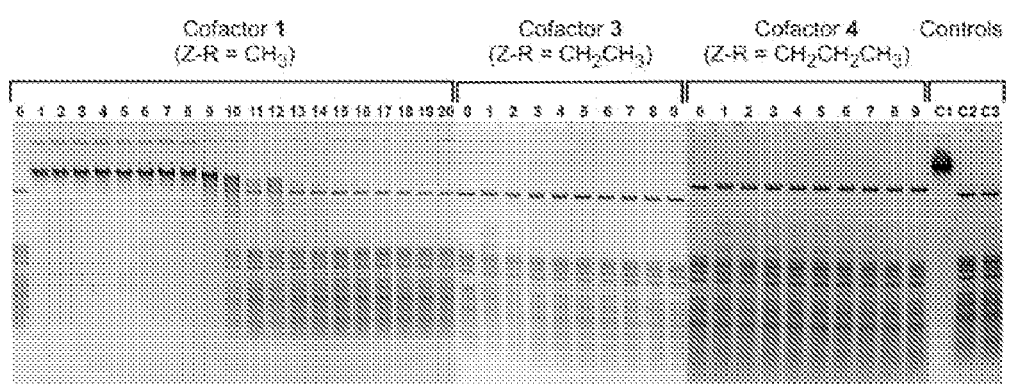
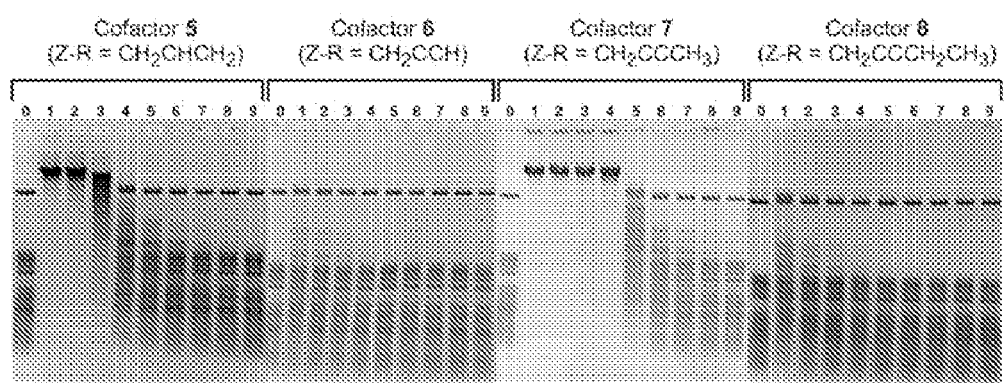
Figure 6B

Figure 7A
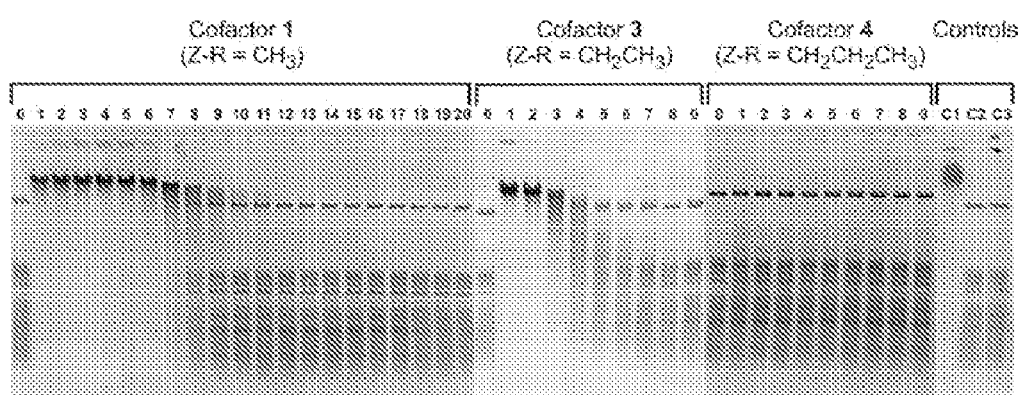
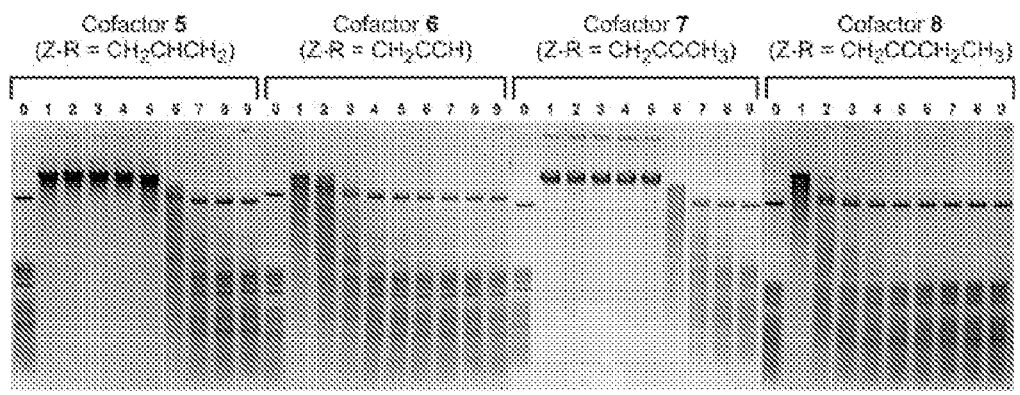
Figure 7B

Figure 8A
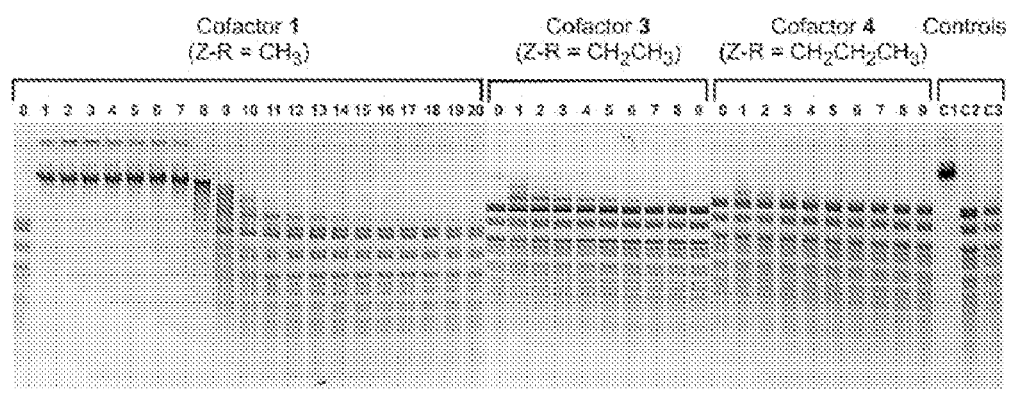
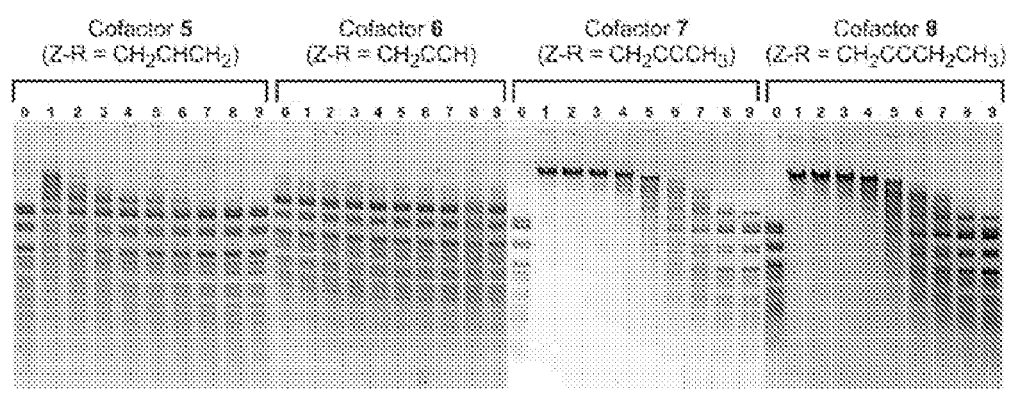
Figure 8B

Figure 10A
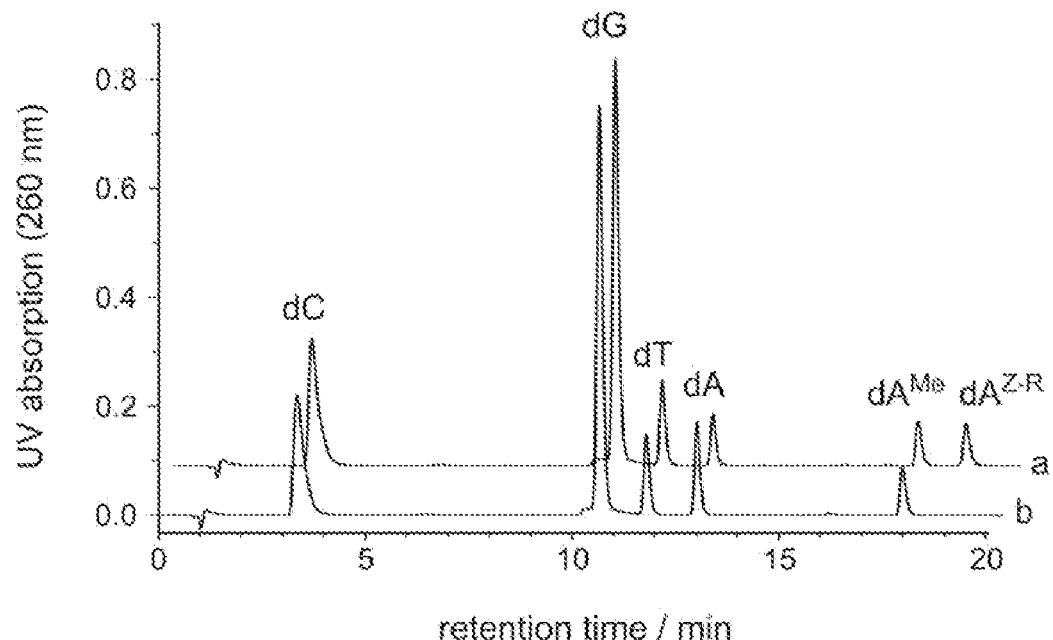
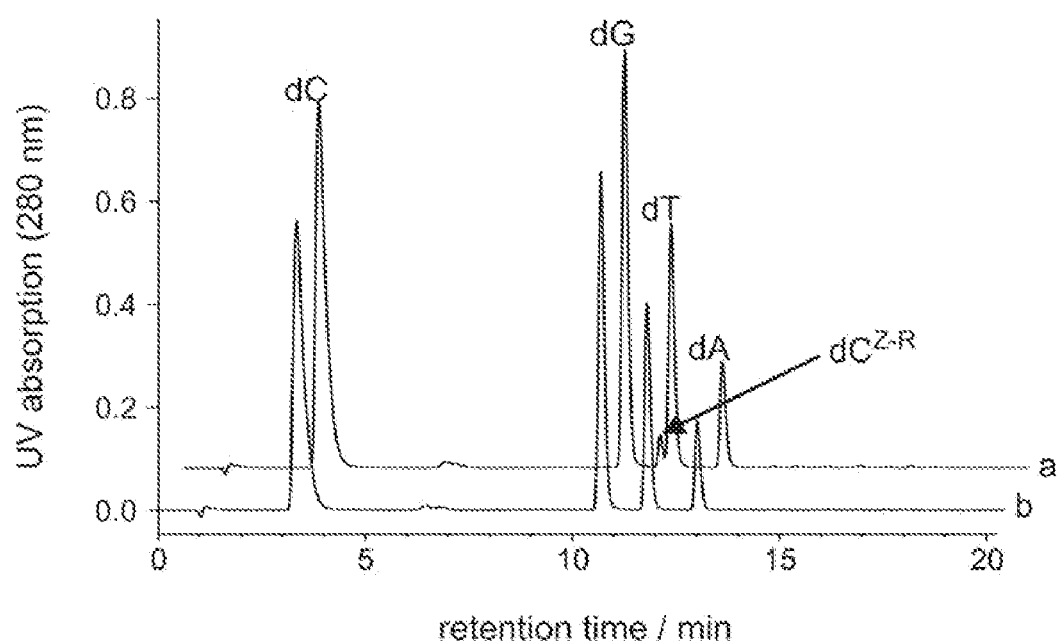
Figure 10B

Figure 12A
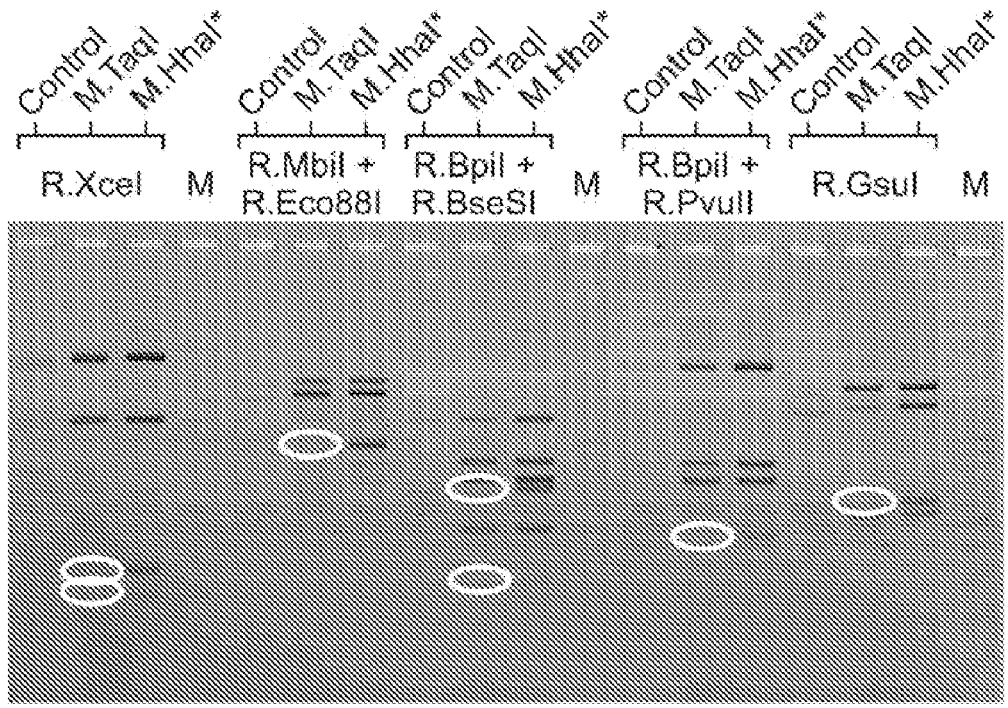
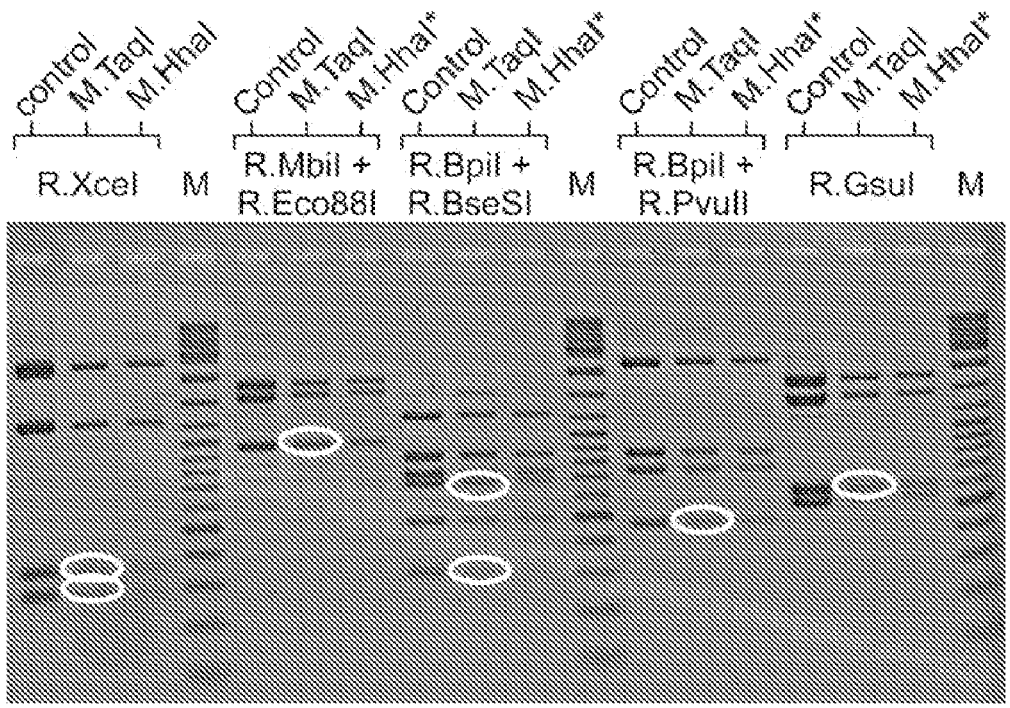
Figure 12B

S-ADENOSYL-L-METHIONINE ANALOGS WITH EXTENDED ACTIVATED GROUPS FOR TRANSFER BY METHYLTRANSFERASES

CROSS-REFERENCE TO RELATED APPLICATIONS

This application is a continuation of PCT/EP2006/003463, filed on 13 Apr. 2006 designating the United States, which claims priority to EP 05008226.2, filed on 14 Apr. 2005, priority to which is claimed under 35 U.S.C. §119(a)-(d).

FIELD OF THE INVENTION

The present invention relates to a compound represented by formula (I)

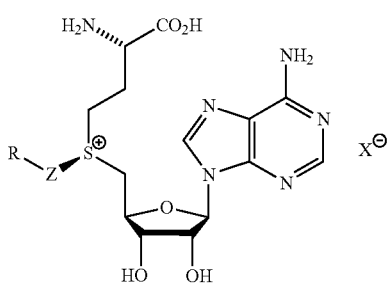

wherein R comprises a carbon-carbon double bond, carbon-oxygen double bond, carbon-sulfur double bond, carbon-nitrogen double bond, a carbon-carbon triple bond, carbon-nitrogen triple bond or an aromatic carbocyclic or heterocyclic system in E-position to the sulfonium center, $X^-$ is an organic or inorganic anion carrying one or more negative charges, Z is $-CR^1R^2-$, $-O-$, $-S-$ or $-NR^3-$, and $R^1$, $R^2$ and $R^3$ are independently selected from H, D and $C_1$-$C_{12}$ alkyl. The present invention also relates to a complex of the compound of the present invention and a methyltransferase which normally uses S-adenosyl-L-methionine (SAM or AdoMet) as a cofactor. Moreover, the present invention relates to a pharmaceutical and a diagnostic composition comprising the compound of the present invention. Finally, the present invention relates to a method for the preparation of a modified target molecule comprising the incubation of the target molecule with a compound of the present invention in the presence of a methyltransferase which is capable of using the compound as a cofactor and under conditions which allow for the transfer of part of the compounds onto the target molecule.

BACKGROUND OF THE INVENTION

Several documents are cited throughout the text of this specification. The disclosure content of the documents cited therein (including manufacture's specifications, instructions, etc.) is herewith incorporated by reference.

Any combination of steps (including single steps only) carried out in vitro and cited through this specification can also be carried out with cell extracts or in vivo.

The present invention is exemplified using DNA methyltransferases (MTases). However, it can also be used with RNA and protein methyltransferases as well as methyltransferases acting on other biomolecules.

DNA methylation is found in almost all organisms (Jeltsch, (2002) ChemBioChem 3, 275-293). The DNA can contain the methylated nucleobases 5-methylcytosine (5-mCyt), N4-methylcytosine (4-mCyt) or N6-methyladenine (6-mAde) in addition to cytosine, adenine, thymine and guanine. These methylated nucleobases are formed by DNA methyltransferases (MTases) which catalyze the transfer of the activated methyl group from the cofactor S-adenosyl-L-methionine (AdoMet) to the C5 carbon of cytosine, the N4 nitrogen of cytosine or the N6 nitrogen of adenine within their DNA recognition sequences (Cheng, (1995) Annu. Rev. Biophys. Biomol. Struct. 24, 293-318). Since a particular nucleotide sequence may exist in its methylated or unmethylated form, DNA methylation can be regarded as an increase of the information content of DNA, which serves a wide variety of biological functions. In prokaryotes DNA methylation is involved in protection of the host genome from endogenous restriction endonucleases, DNA mismatch repair, regulation of gene expression and DNA replication. In eukaryotes DNA methylation plays a role in important regulatory processes such as gene silencing (Bird, (2002) Genes Dev. 16, 6-21), genomic imprinting (Feil and Khosla, (1999) Trends Genet. 15, 431-435), X-chromosome inactivation (Panning and Jaenisch, (1998) Cell 93, 305-308), silencing of intragenomic parasites (Yoder, (1997) Trends Genet. 13, 335-340), and carcinogenesis (Baylin, (1998) Adv. Cancer Res. 72, 141-196; Jones and Laird, (1999) Nat. Genet. 21, 163-167).

Recently, a newly designed fluorescent cofactor for the DNA adenine-6 methyltransferase from *Thermus aquaticus* (M.TaqI) has been presented (Pljevaljcic et al., (2003) J. Am. Chem. Soc. 125, 3486-3492). Naturally, M.TaqI catalyzes the nucleophilic attack of the exocyclic amino group of adenine within the double-stranded, palindromic 5'-TCGA-3' DNA sequence onto the methyl group of the cofactor S-adenosyl-L-methionine (SAM or AdoMet) leading to sequence- and base-specific methyl group transfer. M.TaqI, like other DNA methyltransferases can only transfer one methyl group to each target base and DNA with a fully methylated recognition sequence is not further modified. Replacement of the methionine side chain of the natural cofactor S-adenosyl-L-methionine (SAM or AdoMet) by an aziridinyl residue leads to M.TaqI-catalyzed nucleophilic ring opening and coupling of the whole nucleoside to the target adenine in DNA. The adenosyl moiety is the molecular anchor for cofactor binding. Attachment of a fluorophore via a flexible linker to the 8 position of the adenosyl moiety does not block cofactor binding. This cofactor, 8-amino[1"-(N'-dansyl)-4"-aminobutyl]-5'-(1-aziridinyl)-5'-deoxyadenosine, can be used to sequence-specifically label DNA in a M.TaqI-catalyzed reaction (Pljevaljcic et al., (2003) J. Am. Chem. Soc. 125, 3486-3492).

The prior art describes the above mentioned N-adenosylaziridine derivative as well as 8-amino[1"-(N"-biotinyl)-4"-aminobutyl]-5'-(1-aziridinyl)-5'-deoxyadenosine (Pljevaljcic et al., (2004) Methods Mol. Biol. 283, 145-161) which can be used for labeling biomolecules (Pljevaljcic et al., (2004) ChemBioChem 5, 265-269). Labeling is carried out by using S-adenosyl-L-methionine-dependent methyltransferases. These enzymes naturally catalyze the transfer of the activated methyl group from the cofactor S-adenosyl-L-methionine (1, SAM or AdoMet) to defined nucleophilic positions within various substrates like DNA, RNA, proteins and other biomolecules leading to methylated biomolecules and the demethylated cofactor S-adenosyl-L-homocysteine (2) (Scheme 1). The ability of methyltransferases to catalyze sequence-specific, covalent modifications of biopolymers makes them interesting tools for biotechnology in general and it would be desirable to transfer, in addition to the methyl group, larger chemical entities with additional functionalities to the target biomolecules. In principle, this can be achieved with the N-adenosylaziridine derivatives mentioned above. However, the aziridine cofactors have the disadvantage that they serve as suicide substrates for methyltransferases. After coupling of the aziridine cofactor with the target biomolecule the methyltransferases can not dissociate easily and remain bound to their coupling products. Thus, the methyltransferases do not act as true catalysts and have to be employed in stoichiometric amounts with respect to the target biomolecules. In principle this limitation can be overcome by replacing the methyl group of S-adenosyl-L-methionine (1, SAM or AdoMet) with larger aliphatic groups. Studies by Schlenk (Schlenk and Dainko, (1975) Biochim. Biophy. Acta 385, 312-323; Schlenk, (1977) in Biochem. Adenosylmethionine (eds. Salvatore, Borek and Zappia), Columbia University Press, 3-17) indicated that larger chemical groups like ethyl and propyl can be transferred from S-adenosyl-L-ethionine (3) and S-adenosyl-L-propionine (4) by methyltransferases (Scheme 1). However, it was also found that enzymatic alkyl transfer rates decline drastically with increasing size of the transferable group (methyl >>ethyl>n-propyl group). This general trend was also obtained with different DNA methyltransferases (Example 3).

Scheme 1: Methyltransferases catalyze a nucleophilic attack of various biomolecules on the electrophillic carbon atom next to the sulfonium center of S-adenosyl-L-methionine (1) and analogs with extended saturated side chains.

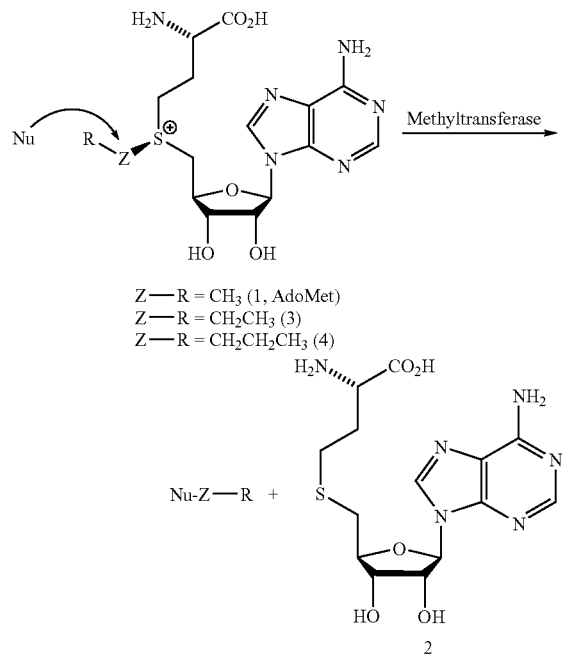

The drastic decline of transfer rates when using transferable groups with increased lengths (see above) prevents S-adenosyl-L-methionine derivatives from being used as effective cofactors of S-adenosyl-L-methionine-dependent methyltransferases. Since S-adenosyl-L-methionine derivatives are closely related to the natural substrates of S-adenosyl-L-methionine-dependent methyltransferases, it would be desirable to develop S-adenosyl-L-methionine-based derivatives with improved transfer rates of sulfonium bound side chains.

SUMMARY OF THE INVENTION

In view of the above, the technical problem underlying the teaching of the present invention was to provide further S-adenosyl-L-methionine-based cofactors for S-adenosyl-L-methionine-dependent methyltransferases.

The solution to this technical problem is achieved by providing the embodiments characterized in the claims.

Accordingly, the present invention relates to a compound represented by formula (I)

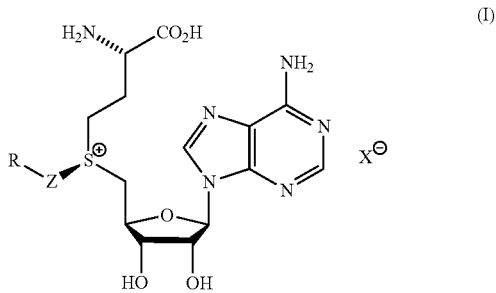

wherein R comprises a carbon-carbon double bond, carbon-oxygen double bond, carbon-sulfur double bond, carbon-nitrogen double bond, a carbon-carbon triple bond, carbon-nitrogen triple bond or an aromatic carbocyclic or heterocyclic system in β-position to the sulfonium center, $X^-$ is an organic or inorganic anion carrying one or more negative charges, Z is —$CR^1R^2$—, —O—, —S— or —$NR^3$— and $R^1$, $R^2$ and $R^3$ are independently selected from H, D and $C_1$-$C_{12}$ alkyl.

BRIEF DESCRIPTION OF THE DRAWINGS

FIG. 4 is a DNA protection assay for M.TaqI-catalyzed transfer of different chemical groups Z—R from the natural cofactor 1 or cofactor analogs 3-9 to phage lambda DNA. DNA (1 µg) and cofactors (300 µM) were first incubated for 4 h with different amounts of M.TaqI (two fold serial dilutions from lanes 1 to 19 starting with 200 ng in lanes 1) and then subjected to fragmentation by R.TaqI. Parallel control experiments with phage lambda DNA were performed in the absence of M.TaqI and cofactors (C1 without R.TaqI and C4 with R.TaqI) and in the presence of M.TaqI (C2 without R.TaqI and C3 with R.TaqI). Complete fragmentation of phage lambda DNA by R.TaqI was observed with all cofactors in the absence of M.TaqI (data not shown).

FIG. 5 shows a DNA protection assay for M.TaqI variant V21G-catalyzed transfer of different chemical groups Z—R from the natural cofactor 1 and cofactor analogs 3-9 to phage lambda DNA. DNA (1 µg) and cofactors (300 µM) were first incubated for 4 h with different amounts of M.TaqI-V21G (two fold serial dilutions from lanes 1 to 21 starting with 200 ng in lanes 1) and then subjected to fragmentation by R.TaqI. Parallel control experiments with phage lambda DNA were performed in the absence of M.TaqI-V21G and cofactors (C1 without R.TaqI and C4 with R.TaqI) and in the presence of M.TaqI-V21G (C2 without R.TaqI and C3 with R.TaqI). Complete fragmentation of phage lambda DNA by R.TaqI was observed with all cofactors in the absence of M.TaqI-V21G (data not shown).

FIG. 6 shows a DNA protection assay for M.HhaI-catalyzed transfer of different chemical groups Z—R from the natural cofactor 1 or cofactor analogs 3-8 to phage lambda DNA. DNA (1.16 µg) and cofactors (300 µM) were first incubated for 4 h with different amounts of M.HhaI (two fold serial dilutions from lanes 1 to 20 starting with 278 ng in lanes 1; M.HhaI is absent in lanes 0) and then subjected to fragmentation by R.Hin6I. Parallel control experiments with phage lambda DNA were performed in the absence of M.HhaI and cofactors (C1 without R.Hin6I and C2 with R.Hin6I) and in the presence of M.HhaI (C3 with R.Hin6I).

FIG. 7 is a DNA protection assay for M.HhaI variant Q82A-catalyzed transfer of different chemical groups Z—R from the natural cofactor 1 and cofactor analogs 3-8 to phage lambda DNA. DNA (1.16 µg) and cofactors (300 µM) were first incubated for 4 h with different amounts of M.HhaI-Q82A (two fold serial dilutions from lanes 1 to 20 starting with 278 ng in lanes 1; M.HhaI-Q82A is absent in lanes 0) and then subjected to fragmentation by R.Hin6I. Parallel control experiments with phage lambda DNA were performed in the absence of M.HhaI-Q82A and cofactors (C1 without R.Hin6I and C2 with R.Hin6I) and in the presence of M.HhaI-Q82A (C3 with R.Hin6I).

FIG. 8 is a DNA protection assay for M.BcnIB-catalyzed transfer of different chemical groups Z—R from the natural cofactor 1 or cofactor analogs 3-8 to phage lambda DNA. DNA (1.1 µg) and cofactors (300 µM) were first incubated for 4 h with different amounts of M.BcnIB (two fold serial dilutions from lanes 1 to 20 starting with 144 ng in lanes 1; M.BcnIB is absent in lanes 0) and then subjected to fragmentation by R.BcnI. Parallel control experiments with phage lambda DNA were performed in the absence of M.BcnIB and cofactors (C1 without R.BcnI and C2 with R.BcnI) and in the presence of M.BcnIB (C3 with R.BcnI).

FIG. 10 depicts an HPLC analysis of enzymatically fragmented duplex oligodeoxynucleotides after DNA methyltransferase-catalyzed modification with cofactor 10. Upper: Fragmentation of duplex oligodeoxynucleotide $I^{Z-R}$-II obtained after treatment with M.TaqI and cofactor 10 (curve a) and fragmentation of duplex oligodeoxynucleotide I-II incubated with M.TaqI in the absence of cofactor 10 for control (curve b). In $dA^{Z-R}$ the chemical group Z—R is attached to the N6 position of dA with $Z=CH_2$, and $R=\!\!-\!\!C\!\!\equiv\!\!CCH_2NHCOCH_2CH_2CH_2NH_2$ ($dA^{Me}$=N6-methyl-2'-deoxyadenosine). Lower: Fragmentation of duplex oligodeoxynucleotide $(III\text{-}IV)^{Z-R}$ obtained after treatment with M.HhaI-Q82A/N304A and cofactor 10 (curve a) and fragmentation of duplex oligodeoxynucleotide III-IV incubated with M.HhaI-Q82A/N304A in the absence of cofactor 10 for control (curve b). In $dC^{Z-R}$ the chemical group Z—R is attached to the C5 position of dC with $Z=CH_2$, and $R=\!\!-\!\!C\!\!\equiv\!\!CCH_2NHCOCH_2CH_2CH_2NH_2$.

FIG. 12 shows sequence-specific two-step fluorescence labeling of pBR322 plasmid DNA according to the present invention. pBR322 plasmid DNA was amino-modified with M.TaqI or M.HhaI variant Q82A/N304A (denoted by M.HhaI*) in the presence of AdoMet analog 10 and reacted with a fluorescein N-hydroxysuccinimidyl ester (Scheme 10). Labeled plasmid DNA was fragmented with different restriction endonucleases or combinations of restriction endonucleases (indicated) and DNA fragments were separated by agarose gel electrophoresis. Fluorescence imaging was performed in the absence (upper) and in the presence of ethidium bromide (lower, for control). DNA fragments derived from pBR322 modification with M.TaqI which do not contain any M.TaqI recognition sequence are not visible in the absence of ethidium bromide staining (indicated by white ellipses). Controls were performed by treating unmodified pBR322 plasmid DNA with fluorescein N-hydroxysuccinimidyl ester followed by restriction endonuclease fragmentation (M=DNA marker).

DETAILED DESCRIPTION OF PREFERRED EMBODIMENTS

Figure 1:
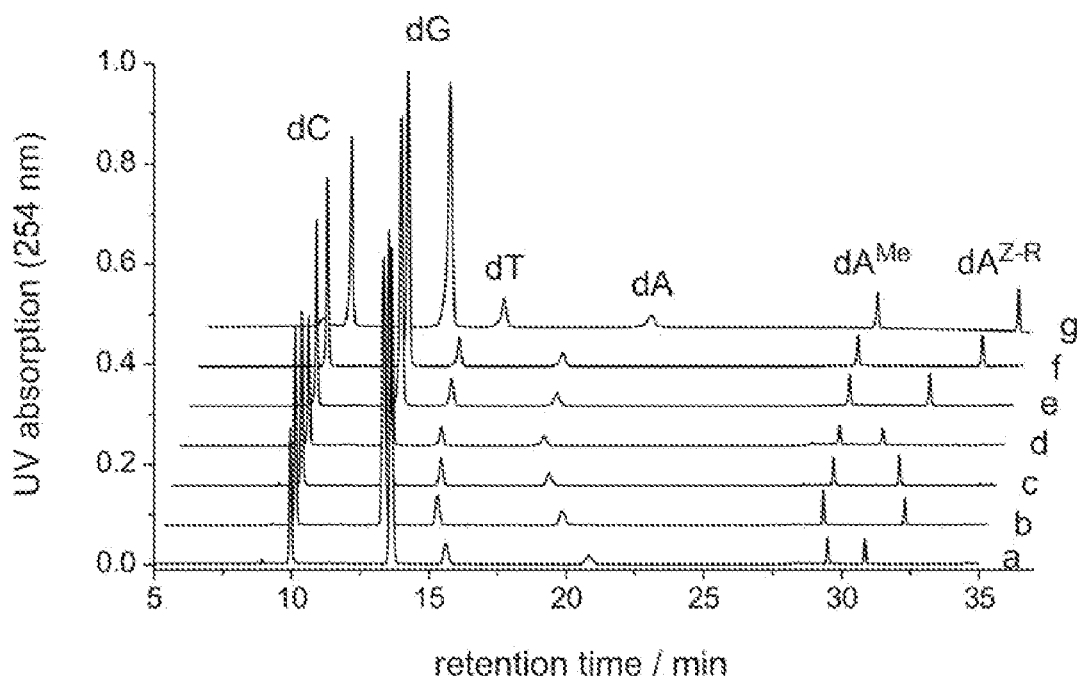
FIG. 1 shows an HPLC analysis of enzymatically fragmented duplex oligodeoxynucleotides $I^{Z-R}$-II obtained after treatment with cofactors 3-9 and M.TaqI ($dA^{Me}$=N6-methyl-2'-deoxyadenosine). In $dA^{Z-R}$ the chemical group Z—R is attached to the N6 position of dA. Curve (a): cofactor 3 with Z=$CH_2$, and R=—$CH_3$; curve (b): cofactor 4 with Z=$CH_2$ and R=—$CH_2CH_3$; curve (c): cofactor 5 with Z=$CH_2$ and R=—CH=$CH_2$; curve (d): cofactor 6 with Z=$CH_2$ and R=—C≡CH; curve (e): cofactor 7 with Z=$CH_2$ and R=—C≡$CCH_3$, curve (f): cofactor 8 with Z=$CH_2$ and R=—C=C—$CH_2CH_3$ and curve (g): cofactor 9 with Z=$CH_2$ and R=—$C_6H_5$.

The teaching of the present application confirms that enzymatic alkyl transfer rates decline drastically with increasing size of the transferable group (methyl >>ethyl>n-propyl group). The reason for this observation has not been elucidated in the art. Based on the experimental data presented in this invention, it is hypothesized that besides steric factors, electronic factors could be responsible for this effect. According to the teaching of the present invention, it is assumed that the reduced transfer rate with increasing length of the transferable group can be overcome by placing a double bond, triple bond, aromatic or heteroaromatic moiety in β-position to the sulfonium center; suitable examples of such substituents of the sulfonium center are allylic, propargylic and benzylic substituents. Indeed, the new AdoMet analogs 5 to 9 with a prop-2-enyl (—CH$_2$CH=CH$_2$; i.e. compound of formula I with Z=CH$_2$ and R=—CH=CH$_2$; cofactor 5), prop-2-ynyl (—CH$_2$C≡CH; i.e. compound of formula I with Z=CH$_2$ and R=—C≡CH; cofactor 6), but-2-ynyl (—CH$_2$C≡C—CH$_3$; i.e. compound of formula I with Z=CH$_2$ and R=—C≡CCH$_3$; cofactor 7), pent-2-ynyl (—CH$_2$C≡CCH$_2$CH$_3$; i.e. compound of formula I with Z=CH$_2$ and R=—C≡CCH$_2$CH$_3$; cofactor 8) or benzyl group (i.e. compound of formula I with Z=CH$_2$ and R=-phenyl; cofactor 9) at the activating sulfonium center serve as good to very good cofactors for various DNA methyltransferases (Example 3). Thus, the poor reactivity of AdoMet analogs with extended saturated alkyl groups at the sulfonium center can be overcome by further activation with a double bond, triple bond or aromatic substituent in β-position to the sulfonium center within the transferable group. Such cofactors should be useful for sequence-specific transfer of reactive groups or other chemical entities to various biomolecules like DNA, RNA and proteins using appropriate methyltransferases as catalysts.

Sequence-specific labeling of biopolymers can be realized in two ways. First, for example the allylic, propargylic or benzylic systems of the cofactors 5, 6 or 9 can be extended with chemical reactive groups, transferred to the target molecule by an appropriate methyltransferase, and then covalently modified with a suitable reactive label (two-step labeling). Second, for example allylic, propargylic or benzylic substituted cofactors with suitable labels can be prepared and these labels then directly transferred to the target molecule by an appropriate methyltransferase (one-step labeling).

These two strategies are illustrated in Scheme 2 using a derivative of cofactor 5, DNA as substrate and the adenine-specific DNA methyltransferase M.TaqI as an example. M.TaqI recognizes the double-stranded DNA sequence 5'-TCGA-3' and naturally transfers the methyl group of S-adenosyl-L-methionine (1, SAM or AdoMet) to the amino group of the adenine residue. With the cofactor 5 an allyl group is sequence- and base-specifically transferred (Example 2A.3). By attaching a chemical reactive group Y to the allylic system via a spacer this reactive group will be efficiently transferred to DNA and can then be modified with a label containing a suitable reactive group V (Scheme 2A). Alternatively, a derivative of cofactor 5 containing a covalently attached label can be synthesized by a reaction of Y and V. The activated group containing the label can then be directly sequence-specifically transferred to DNA by M.TaqI (Scheme 2B). Similar strategies can be envisioned with other compounds according to the present invention, e.g. derivatives of cofactor 6 containing a propargylic and cofactor 9 containing a benzylic activated group.

Scheme 2: Two-step (A) and one-step labeling (B) illustrated by a derivative of cofactor 5, DNA as substrate and the adenine-specific DNA methyltransferase M.TaqI. Y and V are mutually reactive groups, L represents a chemical linkage resulting from the reaction of groups Y and V and the black sphere symbolizes the label.

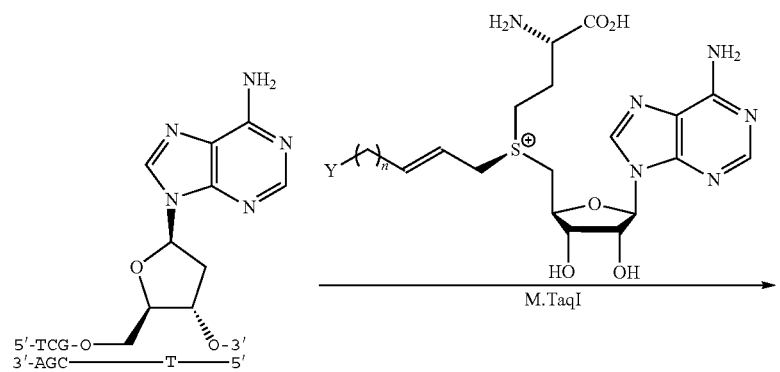

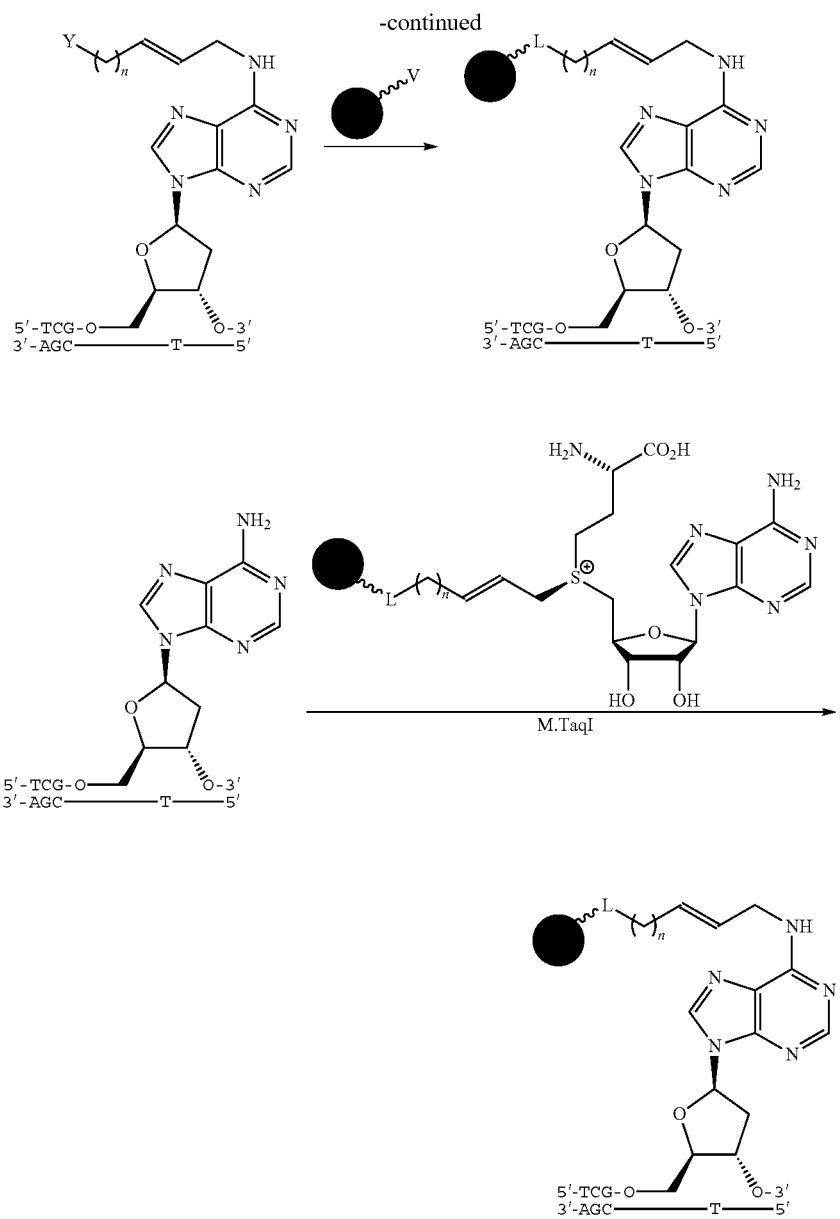

Many chemo-selective ligations defining the reactive groups Y and V and the linkage L are available for attaching a label to the modified biomolecule in aqueous solution. Classical ligations (Garman, (1997) Non-radioactive labeling: A practical introduction, Academic Press) involve primary amino groups which can be reacted with amine reactive groups like N-hydroxysuccinimidyl ester, acyl azide, acyl nitrile, acyl chloride, pentafluorophenyl ester, thioester, sulfonyl chloride, isothiocyanate, imidoester, aldehyde or ketone leading to stable amides, sulfonamides, thioureas, imidates or imines, which can be reduced to stable secondary amines. Thiols specifically react with haloacetamides, maleimides, aziridines or other thiols leading to thioether or disulfide linkages and 1,2-diols can be modified with arylboronic acids. Hydrazines or hydroxylamines can be condensed with aldehydes or ketones leading to hydrazones or oximes. In addition, to these classical ligations several alternative coupling methods proceeding well in aqueous solution have emerged in recent years. 1,2-Aminothiols selectively react with aldehydes or thioesters to form thiazolidines (e.g. N-terminal cysteine residues of polypeptides, Liu and Tam, (1994) Proc. Natl. Acad. Sci. USA 91, 6584-6588) or stable amide bonds (e.g. N-terminal cysteine residues of polypeptides, native chemical peptide ligation, Dawson et al., (1994) Science 266, 776-779). In addition, azides can be reacted with alkynes (Huisgen 1,3-dipolar cycloaddition, Lewis et al. (2002), Angew. Chem. Int. Ed. 41, 1053-1057) or with phosphane esters (Staudinger ligation, Saxon and Bertozzi, (2000) Science 287, 2007-2010) to form 1,2,3-triazoles or amides. Furthermore, Diels-Alder cycloadditions between activated dienes and dienophiles (e.g. furanes and maleimides, Graham et al., (2002) Tet. Lett. 4785-4788) are feasible in aqueous solution. Other modern palladium-catalyzed cross-coupling reactions between arylhalides and terminal alkynes (Sonogashira coupling, Casalnuova and Calabrese, (1990) J. Am. Chem. Soc. 112, 4324-4330; Dibowski and Schmidtchen, (1998) Angew. Chem. Int. Ed. 37, 476-478; Bong and Ghaderi, (2001) Org. Lett. 3, 2509-2511) or between arylhalides and arylboronic acids (Suzuki coupling, Casalnuova and Calabrese, (1990) J. Am. Chem. Soc. 112, 4324-4330; DeVasher et al., (2004) J. Org. Chem. 69, 7919-7927) yielding arylalkynes or biaryls could be used. Additionally, copper-catalyzed alkyne coupling reactions between terminal haloalkynes and terminal alkynes or terminal silylalkyne leading to conjugated diynes can be performed in aqueous solution. Finally, fluorogenic derivatization reagents like 4-halo-7-nitrobenzofurazan, N-methylisatoic anhydride or activated bimanes may be used to label transferred thiol, amino or hydroxyl groups directly.

Nucleic acids generally do not contain highly nucleophilic or electrophilic centers. Thus, in addition to cycloadditions, palladium-catalyzed cross-coupling reactions or copper-catalyzed alkyne coupling reactions, many other reactions between nucleophiles and electrophiles with interchangeable reactive groups Y and V could be used for sequence-specific two-step labeling of nucleic acids (Table 1). In the case of cofactor 6 a terminal alkyne group is transferred to DNA which could be directly coupled with azides (1,3-dipolar cycloaddition), arylhalides (Sonogashira coupling) or terminal haloalkynes (alkyne coupling).

TABLE 1

Sequence-specific two-step labeling of nucleic acids after methyltransferase-catalyzed transfer of reactive groups Y with reactive groups V within the label leading to stable chemical linkages L (compare Scheme 2A).

| Transferred reactive group Y | reactive group V within the label | stable chemical linkage L |
|---|---|---|
| Primary amine | N-hydroxysuccinimidyl ester | amide |
| Primary amine | acyl azide | amide |
| Primary amine | acyl nitrile | amide |
| Primary amine | acyl chloride | amide |
| Primary amine | pentafluorophenyl ester | amide |
| Primary amine | thioester | amide |
| Primary amine | sulfonyl chloride | sulfonamide |
| Primary amine | isothiocyanate | thioureas |
| Primary amine | imidoester | imidate |
| Primary amine | aldehyde, ketone | secondary amine after reduction |
| Thiol | haloacetamide | thioether |
| Thiol | maleimide | thioether |
| Thiol | aziridine | thioether |
| Thiol | thiol | disulfide |
| 1,2-Diol | arylboronic acid | cyclic boronic acid ester |
| Hydrazine | aldehyde, ketone | hydrazone |
| Hydroxylamine | aldehyde, ketone | oxime |
| Haloacetamide | thiol | thioeher |
| Maleimide | thiol | thioether |
| Aldehyde, ketone | primary amine | secondary amine after reduction |
| Aldehyde, ketone | hydrazine | hydrazone |
| Aldehyde, ketone | hydroxylamine | oxime |
| Aldehyde, ketone | 1,2-aminothiols | thiazolidine |
| 1,2-Aminothiol | aldehyde, ketone | thiazolidine |
| 1,2-Aminothiol | thioester | amide |
| Azide | alkyne | 1,2,3-triazole |
| Alkyne | azide | 1,2,3-triazole |
| Azide | phosphane ester | amide |
| Diene | dienophile | cyclohexene |
| Dienophile | diene | cyclohexene |
| Arylhalide | terminal alkyne | arylalkyne |
| Terminal alkyne | arylhalide | arylalkyne |
| Arylhalide | arylboronic acid | biaryl |

TABLE 1-continued

Sequence-specific two-step labeling of nucleic acids after methyltransferase-catalyzed transfer of reactive groups Y with reactive groups V within the label leading to stable chemical linkages L (compare Scheme 2A).

| Transferred reactive group Y | reactive group V within the label | stable chemical linkage L |
|---|---|---|
| Arylboronic acid | Arylhalide | biaryl |
| Terminal haloalkyne | terminal alkyne | diyne |
| Terminal alkyne | terminal haloalkyne | diyne |
| Terminal haloalkyne | terminal silylalkyne | diyne |
| Terminal silylalkyne | terminal haloalkyne | diyne |

For two-step sequence-specific labeling of polypeptides fewer chemo-selective ligation reactions than for nucleic acids are available, because polypeptides generally contain nucleophilic centers (amino and to a lesser extent thiol groups). A list of feasible reactions is given in Table 2. Again, the terminal alkyne group transferred with for instance cofactor 6 could be directly coupled with azides (1,3-dipolar cycloaddition), arylhalides (Sonogashira coupling) or terminal haloalkynes (alkyne coupling).

TABLE 2

Sequence-specific two-step labeling of polypeptides after methyltransferase-catalyzed transfer of reactive groups Y with reactive groups V within the label leading to stable chemical linkages L (compare Scheme 2A).

| Transferred reactive group Y | reactive group V within the label | stable linkage L |
|---|---|---|
| 1,2-Diol | arylboronic acid | cyclic boronic acid ester |
| Hydrazine | aldehyde, ketone | hydrazone |
| Hydroxylamine | aldehyde, ketone | oxime |
| Haloacetamide | thiol | thioeher |
| Maleimide | thiol | thioether |
| Aldehyde, ketone | primary amine | secondary amine after reduction |
| Aldehyde, ketone | hydrazine | hydrazone |
| Aldehyde, ketone | hydroxylamine | oxime |
| Aldehyde, ketone | 1,2-aminothiol | thiazolidine |
| 1,2-Aminothiol | aldehyde | thiazolidine |
| 1,2-Aminothiol | thioester | amide |
| Azide | alkyne | 1,2,3-triazole |
| Alkyne | azide | 1,2,3-triazole |
| Azide | phosphane ester | amide |
| Diene | dienophile | cyclohexene |
| Dienophile | diene | cyclohexene |
| Arylhalide | terminal alkyne | arylalkyne |
| Terminal alkyne | arylhalide | arylalkyne |
| Arylhalide | arylboronic acid | biaryl |
| Arylboronic acid | Arylhalide | biaryl |
| Terminal haloalkyne | terminal alkyne | diyne |
| Terminal alkyne | terminal haloalkyne | diyne |
| Terminal haloalkyne | terminal silylalkyne | diyne |
| Terminal silylalkyne | terminal haloalkyne | diyne |

For one-step labeling (Scheme 2B) labeled cofactors (I) with allylic, propargylic or benzylic systems need to be prepared first. In principle, this can be done in two ways and is illustrated in Scheme 3 for labeled derivatives of the allylic cofactor 5. For example, a label containing a reactive group V can be attached to an allylic alcohol containing a reactive group Y. Afterwards, the alcohol is activated (e.g. X=a halide or sulfonate) and reacted with S-adenosyl-L-homocysteine (2) leading to the desired labeled cofactors (Scheme 3, left). Since covalent attachment of labels can be performed in aqueous or in organic solvents, many combinations for activated groups Y and V are feasible (Table 3). Of course, this reaction scheme requires that the label itself is stable towards the conditions of label attachment, activation and reaction with S-adenosyl-L-homocysteine (2).

Scheme 3: Two synthetic routes to labeled allylic cofactors from S-adenosyl-L-homocysteine (2). Y and V are mutually reactive groups, L represents a chemical linkage, X is a halide or sulfonate and the black sphere symbolizes a label.

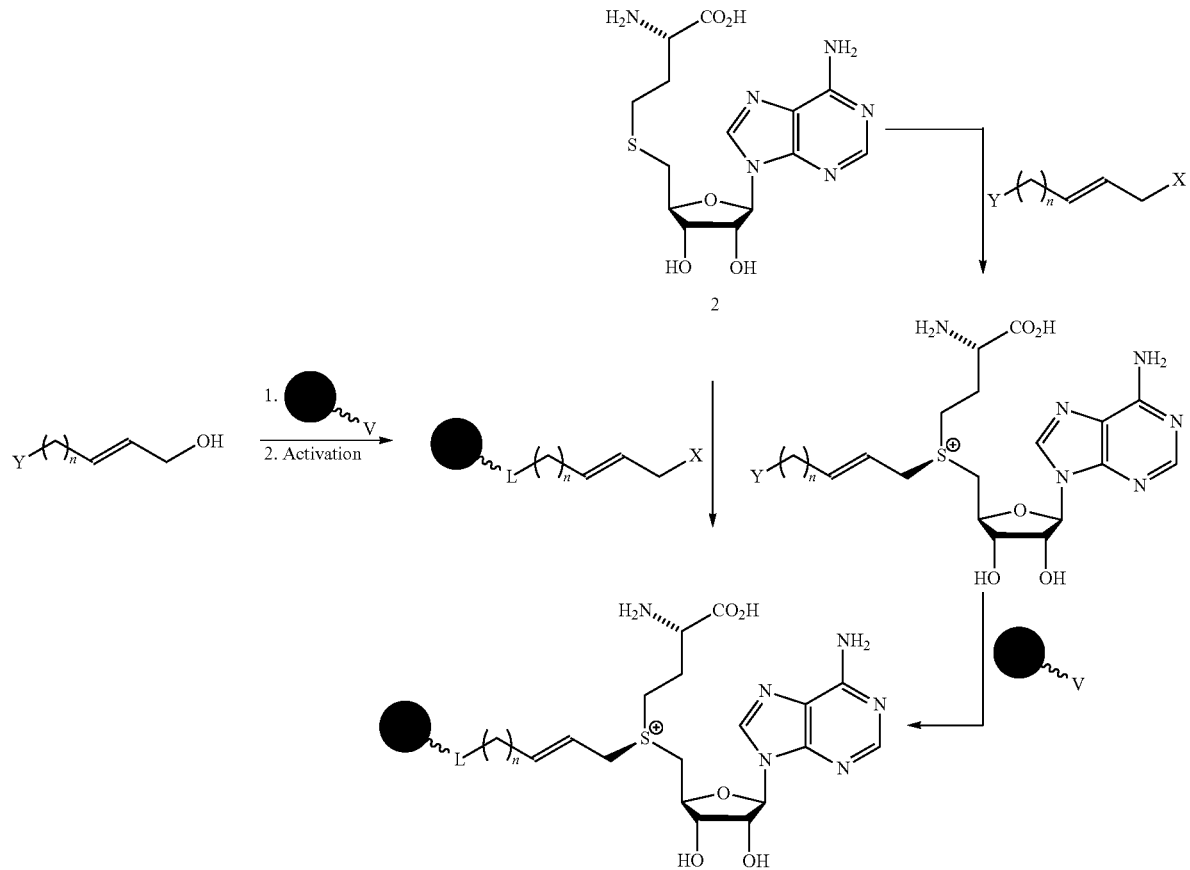

TABLE 3

Attachment of labels containing a reactive group V to allylic, propargylic or benzylic alcohols with a reactive group Y for the synthesis of allylic, propargylic and benzylic cofactors containing a label within the group transferred by methyltransferases (reactive groups Y and V and stable chemical linkages L as in Scheme 3, left).

| Reactive group Y | reactive group V | stable chemical linkage L |
|---|---|---|
| Primary amine | N-hydroxysuccinimidyl ester | amide |
| Primary amine | acyl azide | amide |
| Primary amine | acyl nitrile | amide |
| Primary amine | acyl chloride | amide |
| Primary amine | pentafluorophenyl ester | amide |
| Primary amine | thioester | amide |
| Primary amine | sulfonyl chloride | sulfonamide |
| Primary amine | isothiocyanate | thioureas |
| Primary amine | imidoester | imidate |
| Primary amine | aldehyde, ketone | secondary amine after reduction |
| Thiol | haloacetamide | thioether |
| Thiol | maleimide | thioether |
| Thiol | aziridine | thioether |
| Thiol | thiol | disulfide |
| 1,2-Diol | arylboronic acid | cyclic boronic acid ester |
| 1,2-Aminothiol | thioester | amide |
| 1,2-Aminothiol | aldehyde, ketone | thiazolidine |
| Hydrazine | aldehyde, ketone | hydrazone |
| Hydroxylamine | aldehyde, ketone | oxime |

TABLE 3-continued

Attachment of labels containing a reactive group V to allylic, propargylic or benzylic alcohols with a reactive group Y for the synthesis of allylic, propargylic and benzylic cofactors containing a label within the group transferred by methyltransferases (reactive groups Y and V and stable chemical linkages L as in Scheme 3, left).

| Reactive group Y | reactive group V | stable chemical linkage L |
|---|---|---|
| N-Hydroxysuccinimidyl-ester | primary amine | amide |
| Acyl azide | primary amine | amide |
| Acyl nitrile | primary amine | amide |
| Acyl chloride | Primary amine | amide |
| Pentafluorophenyl-ester | primary amine | amide |
| Thioester | primary amine | amide |
| Sulfonyl chloride | primary amine | sulfonamide |
| Isothiocyanate | primary amine | thioureas |
| Imidoester | primary amine | imidate |
| Aziridine | primary amine | secondary amine |
| Aldehyde, ketone | primary amine | secondary amine after reduction |
| Haloacetamide | thiol | thioeher |
| Maleimide | thiol | thioether |
| Aziridine | thiol | thioether |
| Thiol | thiol | disulfide |
| Aldehyde, ketone | hydrazine | hydrazone |
| Aldehyde, ketone | hydroxylamine | oxime |
| Aldehyde, ketone | 1,2-aminothiol | thiazolidine |
| Arylboronic acid | 1,2-diol | cyclic boronic acid ester |

TABLE 3-continued

Attachment of labels containing a reactive group V to allylic, propargylic or benzylic alcohols with a reactive group Y for the synthesis of allylic, propargylic and benzylic cofactors containing a label within the group transferred by methyltransferases (reactive groups Y and V and stable chemical linkages L as in Scheme 3, left).

| Reactive group Y | reactive group V | stable chemical linkage L |
|---|---|---|
| Azide | alkyne | 1,2,3-triazole |
| Alkyne | azide | 1,2,3-triazole |
| Azide | phosphane ester | amide |
| Phosphane ester | azide | amide |
| Diene | dienophile | cyclohexene |
| Dienophile | diene | cyclohexene |
| Arylhalide | terminal alkyne | arylalkyne |
| Terminal alkyne | arylhalide | arylalkyne |
| Arylhalide | arylboronic acid | biaryl |
| Arylboronic acid | Arylhalide | biaryl |
| Terminal haloalkyne | terminal alkyne | diyne |
| Terminal alkyne | terminal haloalkyne | diyne |
| Terminal haloalkyne | terminal silylalkyne | diyne |
| Terminal silylalkyne | terminal haloalkyne | diyne |

Alternatively, the label could be introduced into cofactors (I) with allylic, propargylic and benzylic systems containing a reactive group Y. This is illustrated in Scheme 3 (right) using a labeled derivative of the allylic cofactor 5 as example. Given the instability of S-adenosyl-L-methionine (1) under basic conditions, chemo-selective ligation reactions proceeding well under slightly acidic conditions in aqueous solution will be advantages for the synthesis of labeled cofactors via this synthetic route. Possible ligation reactions are listed in Table 4. In the case of cofactor 6 a terminal alkyne group is already present which could be directly coupled with arylhalides (Sonogashira coupling) leaving the propargylic system after ligation intact.

TABLE 4

Chemo-selective ligation reactions under slightly acidic aqueous conditions for the synthesis of allylic, propargylic and benzylic cofactors containing a label within the group transferred by methyltransferases (reactive groups Y and V and stable chemical linkages L as in Scheme 3, right).

| Reactive group Y | reactive group V | stable chemical linkage L |
|---|---|---|
| Aldehyde, ketone | hydrazine | hydrazone |
| Aldehyde, ketone | hydroxylamine | oxime |
| Aldehyde, ketone | 1,2-aminothiol | thiazolidine |
| Azide | alkyne | 1,2,3-triazole |
| Alkyne | azide | 1,2,3-triazole |
| Azide | phosphane ester | amide |
| Diene | dienophile | cyclohexene |
| Dienophile | diene | cyclohexene |
| Arylhalide | terminal alkyne | arylalkyne |
| Terminal alkyne | arylhalide | arylalkyne |
| Arylhalide | arylboronic acid | biaryl |
| Arylboronic acid | Arylhalide | biaryl |
| Terminal alkyne | terminal haloalkyne | diyne |
| Terminal haloalkyne | terminal alkyne | diyne |

In a preferred embodiment of the present invention, Z is $CR^1R^2$ with $R^1$, $R^2$ being independently selected from H, D and $C_1$-$C_{12}$ alkyl.

In a more preferred embodiment of the present invention $Z=\!-CR^1R^2-\!$ with $R^1$ and $R^2$ being independently selected from H and D.

In another preferred embodiment of the present invention, R comprises —CH=CH—, —C≡C—, or a phenyl group in β-position to the sulfonium center. Examples of such compounds, which are in accordance with the teaching of the present invention, are represented by formulae (II), (III) or (IV)

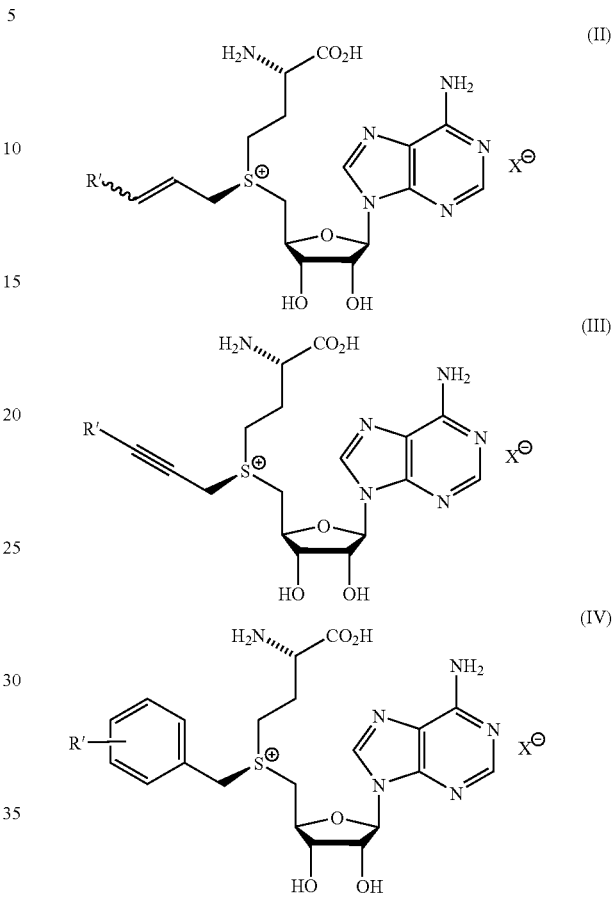

wherein $X^-$ is an organic or inorganic molecule carrying one or more negative charges.

In another preferred embodiment of the present invention said organic or inorganic anion is selected from trifluoroacetate, formate, halide and sulfonate.

In another preferred embodiment of the present invention, R additionally comprises at least one member selected from functional groups, heavy atoms or heavy atom clusters suitable for phasing of X-ray diffraction data, radioactive or stable rare isotopes, and a residue of a member selected from fluorophores, fluorescence quenchers, affinity tags, crosslinking agents, nucleic acid cleaving reagents, spin labels, chromophors, proteins, peptides or amino acids which may optionally be modified, nucleotides, nucleosides, nucleic acids which may optionally be modified, carbohydrates, lipids, transfection reagents, intercalating agents, nanoparticles and beads.

Preferred radioactive or stable rare isotopes are selected from the group consisting of $^3$H (T), $^{14}$C, $^{32}$P, $^{33}$P, $^{35}$S, $^{125}$I, $^{131}$I, $^2$H (D), $^{13}$C, $^{15}$N, $^{17}$O and $^{18}$O. Furthermore, preferred stable isotopes are selected from the group consisting of $^{19}$F and $^{127}$I.

Preferred spin labels which are stable paramagnetic groups (typically a nitryl radical) are selected from the group consisting of 2,2,6,6,-tetramethyl-piperidin-1-oxyl and 2,2,5,5,-tetramethyl-pyrrolidin-1-oxyl.

Preferred amino acid modifications are selected from the group consisting of β- and γ-amino acids and preferred peptide modifications are selected from the group consisting of depsipeptides, vinylogous peptides, permethylated peptides, peptoids, azapeptides (azatides), oligocarbamates, oligoureas, oligosulfones, oligosulfonamides, oligosulfinamides, pyrrole-imidazole-hydroxypyrrole polyamides and peptide nucleic acids (PNA), more preferably said peptide modifications are pyrrole-imidazole-hydroxypyrrole polyamides and peptide nucleic acids (PNA).

Preferred nucleic acid modifications are selected from the group consisting of peptide nucleic acids (PNA), locked nucleic acids (LNA) and phosphorothioate modified nucleic acids.

Preferred transfection reagents are selected from the group consisting of cationic lipids (e.g. Lipofectamin and derivatives commercially available from Invitrogen, Calif., USA), cationic polymers (e.g. polyethyleneimine (PEI) commercially available from Sigma) and polycationic dendrimers.

Preferred intercalating agents which are typically planar or near planar aromatic ring systems binding between neighboring base-pairs in double-stranded nucleic acids are selected from the group consisting of ethidium, thiazole orange, acridine or a derivative thereof, and pyrene.

Preferred nanoparticles are selected from the group consisting of gold and silver clusters.

Preferred beads are selected from the group consisting of silica beads, magnetic beads and polystyrene microspheres (e.g. commercially available from Molecular Probes, Oreg., USA)

In one embodiment of the present invention, said functional group is selected from an amino group, a thiol group, a 1,2-diol group, a hydrazino group, a hydroxyamino group, a haloacetamide group, a maleimide group, an aldehyde group, a ketone group, an 1,2-aminothiol group, an azido group, an alkyne group, a 1,3-diene function, a dienophilic function (e.g. activated carbon-carbon double bond), an arylhalide group, a terminal alkyne group, an arylboronic acid group, a terminal haloalkyne group, a terminal silylalkyne group and a protected amino, thiol, 1,2-diol, hydrazino, hydroxyamino, aldehyde, ketone and 1,2-aminothiol group.

In another embodiment of the present invention, said fluorophore is a compound sold under the trade name of Alexa™, 4,4-difluoro-4-bora-3a,4a-diaza-s-indacene (BODIPY), bimane, coumarin, Cascade blue, dansyl, dapoxyl, fluorescein, mansyl, N-methylanthraniloyl (MANT), Oregon green, pyrene, rhodamine, Texas red, 2-p-toluidinonaphthalene-6-sulfonate (TNS), fluorescent nanocrystals (quantom dots), a cyanine fluorophore and derivatives thereof.

In another preferred embodiment of the present invention, said fluorescence quencher is dabcyl, or those sold under the trade name QSY™ or BHQ™.

In yet another embodiment of the present invention, said affinity tag is selected from peptide tags, metal-chelating groups, isotope coded affinity tags, biotin, maltose, mannose, glucose, N-acetylglucosamine, N-acetylneuraminic acid, galactose, N-acetylgalactosamine, digoxygenin and dinitrophenol.

In another embodiment of the present invention, said peptide tag is selected from his-tags, tags with metal chelating properties, strep-tags, flag-tags, c-myc-tags, HA-tags, epitopes and glutathione.

The term "affinity tag" as used herein relates inter alia to a label which can, for example, be used for affinity purification. A number of affinity tags which are in accordance with the present invention are well known in the art. Such tags may for example have metal chelating properties and may allow to bind the side chain —Z—R of cofactor (I) of the present invention, before or after methyltransferase-catalyzed transfer to a biomolecule, to a matrix used in Immobilized Metal Ion Affinity Chromatography (IMAC). The IMAC technique developed by Porath et al. (Porath et al., (1975) Nature 258, 598-599) is based on the interaction between certain protein superficial residues (histidines, cysteines, and in a lower degree tryptophans) and cations from transition metals which form chelates with polycarboxylic ligands. Typical conditions are described in the art and are known to the skilled person (Porath, (1992) Protein Expression and Purification 3, 263-281; Hemdan, and Porath, (1985) Journal of Chromatography 323, 255-264; Porath and Hansen, (1991) Journal of Chromatography 550, 751-764).

Other preferred tags include "strep-tag" which relates to an 8 amino acid streptavidin binding sequence. This sequence was found through the systematic screening of random peptide libraries in order to identify a peptide binding sequence with optimal affinity tag properties (Schmidt and Skerra, (1993) Prot. Engineering 6, 109-122). When attached to the side chain —Z—R of cofactor (I) of the present invention, modified nucleic acid molecules or (poly)peptides can be affinity purified, e.g. by using a gravity-flow column with a matrix containing StrepTactin, Streptavidin, Avidin or the like. Such matrices are commercially available from, e.g. Sigma-Genosys/The Woodlands (Tx, USA) or IBA/Goettingen (Germany).

Other preferred tags include the "flag-tag" which relates to an 8 amino acid peptide which binds to an anti-flag antibody. When attached to the side chain —Z—R of cofactor (I) of the present invention, modified nucleic acid molecules or (poly)peptides can be affinity purified, e.g. by using a gravity-flow column with a matrix containing an immobilized anti-flag antibody. Such matrix is commercially available from, e.g. Sigma-Aldrich.

Other preferred tags include "c-myc-tag" which relates to a 10 amino acid peptide which binds to an anti-c-myc antibody. When attached to the side chain —Z—R of cofactor (I) of the present invention, modified nucleic acid molecules or (poly)peptides can be affinity purified, e.g. by using a gravity-flow column with a matrix containing an immobilized anti-c-myc antibody. Such matrix is commercially available from, e.g. Pierce Biotechnology (IL, USA).

Other preferred tags include "HA-tag" which relates to 9 amino acid peptide which is derived from the surface hemagglutinin of influenza virus and binds to an anti-HA antibody. When attached to the side chain —Z—R of cofactor (I) of the present invention, modified nucleic acid molecules or (poly) peptides can be affinity purified, e.g. by using a gravity-flow column with a matrix containing immobilized anti-HA antibody.

In another embodiment of the present invention, said metal-chelating group is nitrilotriacetic acid, ethylenediaminetetraacetic acid (EDTA), 1,10-phenanthroline, a crown ether and a $His_{4-8}$ peptide.

Preferably, said crosslinking agent is selected from mono- or bifunctional platinum(II) complexes, maleimides, iodacetamides, aldehydes and photocrosslinking agents like arylazide, a diazo compound, a 2-nitrophenyl compound, psoralen and a benzophenone compound.

In another embodiment of the present invention, said heavy atom or heavy atom cluster is preferably selected from copper, zinc, selenium, bromine, iodine, ruthenium, palladium, cadmium, tungsten, platinum, gold, mercury, bismuth, samarium, europium, terbium, uranium, $Ta_6Br_{14}$, $Fe_4S_4$ and $P_2W_{18}O_{62}$ suitable for phasing X-ray diffraction data.

Preferred nucleic acid cleaving reagents are selected from the group consisting of iron-EDTA, copper-1,10-phenanthroline, acridine or a derivative thereof, an enediyne compound and a rhodium complex, more preferably said nucleic acid cleaving reagent is selected from iron-EDTA, copper-1,10-phenanthroline and a rhodium complex.

The present invention also relates to a complex of a compound (I) of the present invention and a methyltransferase which normally uses S-adenosyl-L-methionine (SAM or AdoMet) as a cofactor.

In a preferred embodiment of the present invention, said methyltransferase normally transfers the methyl residue of S-adenosyl-L-methionine (SAM or AdoMet) onto a nucleic acid molecule, a polypeptide, a carbohydrate or a small molecule. An overview on SAM (AdoMet)-dependent methyltransferases is for instance given by Kagan and Clarke, (1994) Archives of Biochemistry and Biophysics 310, 417-427. This article also gives a list of small molecule O-methyltransferases and small molecule N-methyltransferases which include for example catechol O-methyltransferase and glycine N-methyltransferase.

The terms "nucleic acid molecule", "polypeptide", "carbohydrate" or "small molecule" are sometimes referred to as biomolecules. Biomolecules may be entirely natural, i.e. unmodified, synthetic or modified and may exist as complexes. Accordingly, for example the term "nucleic acid molecule" comprises DNA and RNA molecules as well as modified DNA and RNA molecules. DNA may be for example cDNA or genomic DNA. RNA may be for example mRNA, hnRNA, spliced and unspliced RNA etc. Whenever the term polypeptide is used herein, it is to be understood as comprising protein, peptides and polypeptides. Peptides may be as short as for example 10, 11, 12, 13, 14, 15 or 16 residues in length.

In a more preferred embodiment of the present invention, said methyltransferase is an orphan DNA methyltransferase or part of a bacterial restriction modification system.

Said DNA methyltransferase may be selected from the group consisting of M.AacDam, M.AatII, M.AbaORFDP, M.AbaORFKP, M.AbrI, M.AbrI, M.AbrIII, M.AciI, M.AcII, M.AcuI, M.Afa22MI, M.AflII, M.AflIII, M.AgeI, M.AhdI, M.AhyBP, M.AlaK2I, M.AluI, M.AlwI, M.Alw26I, M.ApaI, M.ApaLI, M.ApeKI, M.ApoI, M.AquI, M.AscI, M.AseI, M.AseII, M.AsiSI, M.AspCNI, M.AtuCI, M.AtuCORF1997P, M.AtuDORF794P, M.AtuDORF3839P, M.AvaI, M.AvaII, M.AvaIII, M.AvaIVP, M.AvaV, M.AvaVI, M.AvaVII, M.AvaVIII, M.AvaIX, M.AvaORF3700P, M.AvaORF7270P, M.AvrI, M.AvrII, M.BabI, M.BaeI, M.BalI, M.BamHI, M.BamHII, M.BanI, M.BanII, M.BanIII, M.BatAORF3814P, M.BatA581ORF3846P, M.Bbu297I, M.BbvI, M1.BbvCI, M2.BbvCI, M.BbvSI, M1.BccI, M2.BccI, M.Bce1247I, M1.BceAI, M2.BceAI, M.Bce14579ORF939P, M.BceSORF365P, M.BceSORF4605P, M1.BceSORF5606P, M2.BceSORF5606P, M.Bcep1P, M.Bcep43ORFAP, M.BchI, M.BclI, M1.BcnI, M2.BcnI (M.BcnIB), M1.BcoKI, M2.BcoKI, M.Bcs139P, M.BdiI, M.BepI, M1.BfaI, M2.BfaI, M.BfaORFC157P, M2.BfiI (M.BfiC2), M1.BfuAI, M2.BfuAI, M.BgII, M.BgIII, M1.BhaI, M2.BhaI, M.BhaII, M.BjaORF2509P, M.BloNORF564P, M.BloNORF1473P, M.BlpI, M.BmaI, M.BmaPhiE125ORF56P, M.Bme216I, M.BmeLORF1444P, M.BmeTI, M1.BmrI, M2.BmrI, M.BnaI, M.BpmI, M1.Bpu10I, M2.Bpu10I, M1.BsaI, M2.BsaI, M.BsaAI, M.BsaJI, M.BsaWI, M1.BscGI, M2.BscGI, M.Bse634I, M.BseCI, M.BseDI, BseMII, M.BseRI, M.BseRI, M.BseYI, BsgI, M.BsgI, M.BsiWI, M.BslI, M1.BsmI, M2.BsmI, M.BsmAI, M.BsmBI, M.BsoBI, M.BspI, M.Bsp6I, M.Bsp50I, M.Bsp98I, M.Bsp106I, M.Bsp143II, BspCNI, M.BspCNI, M.BspEI, M.BspHI, M.BsplS4I, M.BspKT6I, BspLU11III, M1.BspLU11III, M2.BspLU11III, M1.BspMI, M2.BspMI, M.BspMII, M.BspRI, M.BspST5I, M1.BsrI, M2.BsrI, M1.BsrBI, M2.BsrBI, M.BsrFI, M.BssHI, M.BssHII, M.BssSI, M.BstI, M.BstEII, M.BstEIII, M1.BstF5I, M2.BstF5I, M3.BstF5I, M4.BstF5I, M.BstGII, M.BstLVI, M.BstNI, M.BstNBI, M.BstVI, M.BstXI, M.BstYI, M.Bsu15I, M.Bsu36I, M.Bsu6633I, M.BsuBI, M.BsuEII, M.BsuFI, M.Bsu1330ORF491P, M.BsuRI, M.BthIPS78, M.BthVORF4625P, M.BusLBORFC747P; M.BusLBORFC755P, M.Cac8I, M.Cac824I, M.Cac824ORF3358P, M.CauJORFC101P, M.CauJORFC102P, M.CauJORFC103P, M.CauJORFC104P, M.CauJORFC107P, M.CauJORFC110P, M.CauJORFC111P, M.CboI, M.CcrMI, M.Cdi630I, M.CdiCD6I, M.CdiCD6II, M.Cdi630ORFC898P, M.CefORF1493P, M.CeqI, M.CfrI, M.Cfr6I, M.Cfr9I, M.Cfr10I, M.Cfr13I, M.Cfr42I, M.CfrAI, M.CfrBI, M.CggI, M.CgIASI, M.CgILP6P, M.CjeNI, M.Cje81116ORFBP, M.Cje81116ORFCP, M.ClaI, M.Csp6I, M.Csp68KI, M.Csp68KIV, M.Csp68 KV, M.CteEORF387P, M.CthORFS26P, M.CthORFS34P, M.CthORFS93P, M.CviAI, M.CviAII, M.CviAIV, M.CviBI, M.CviBII, M.CviBIII, M.CviJI, M.CviORF5P, M.CviORF2111P, M.CviPI, M.CviQI, M.CviQII, M.CviQIII, M.CviQIVP, M.CviQVP, M.CviQVI, M.CviQVII, M.CviQVIIIP, M.CviQIXP, M.CviQXP, M.CviQXI, M.CviRI, M.CviRII, M.CviSI, M.CviSII, M.CviSIII, M.CviSIVP, M.CviSVP, M.CviSVIP, M.CviTI, M.DdeI, DhaORFC135P, M1.DpnII, M2.DpnII, M.DraI, M.DraII, M.DraIII, M.DsaV, M.DvuORF19P, M.DvuORF2842P, M.EacI, M.EaeI, M.EagI, M1.EarI, M2.EarI, M.EcaI, M.Ec118kI, M1.Eco3I, M2.Eco3I, M.Eco32I, M.Eco47II, M.Eco47III, M.Eco56I, Eco57I, M.Eco57I, M.Eco64I, M.Eco72I, M.Eco88I, M.Eco98I, M.Eco105, M.Eco147I, M.Eco23I, M.Eco255I, M.Eco536P, M.Eco1639P, M.Eco183I, M.Eco248534P, M.EcoAI, M.EcoBI, M.EcoCFTDamP, M.EcoCFTDam2P, M.EcoCFTDam3P, M.EcoCFTDcmP, M.EcoDI, M.EcoDR2, M.EcoDR3, M.EcoDXXI, M.Eco67Dam, M.EcoEI, M.EcoHI, M.EcoHK31I, M.EcoKI, M.EcoKII, M.EcoKDam, M.EcoKDcm, M.EcoKO157DamP, M.EcoKO157Dam2P, M.EcoKO157Dam3P, M.EcoKO157DcmP, M.EcoKO157ORF1953P, M.EcoLahn1P, M.EcoLahn3P, M.EcoNI, M.EcoNi12P, M.EcoO109I, M.EcoO157DamP, M.EcoO157DcmP, M.EcoO157ORF1454P, M.EcoO157ORF2389P, M.EcoO157ORF3349P, M.Eco536ORF3P, M.EcoPI, M.EcoP15I, M.EcoP1Dam, M.EcoPhi4795DamP, M.EcoRI, M.EcoRII, M.EcoRV, M.EcoR124I, M.EcoR124II, M.EcoRD2, M.EcoRD3, M.EcoStx1DamP, M.EcoStx2DamP, M.EcoT22I, M.EcoT38I, M.EcoT1Dam, M.EcoT2Dam, M.EcoT4Dam, M.EcoVIII, M.EcoVT2Dam, M.EcoWphiP, M.Eco29kI, M.EcopHSHP, M.EcopHSH2P, M.EcoprrI, M.EfaHGSOR-FHP, M.EphPI ORF1P, M.EsaBC1I, M.EsaBC3I, M.EsaBC4I, M.EsaBS1I, M.EsaBS9I, M.EsaDix1I, M.EsaDix2I, M.EsaDix3I, M.EsaDix4I, M.EsaDix5I, M.EsaDix6I, M.EsaDix7I, M.EsaLHCI, M.EsaLHCIII, M.EsaRM1P, M.EsaRM13P, M.EsaRM16P, M.EsaRM17P, M.EsaRM21P, M.EsaRM38P, M.EsaRM61P, M.EsaRM63P, M.EsaRM65P, M.EsaRM67P, M.EsaRM69P, M1.EsaS1I, M2.EsaS1I, M.EsaS3I, M.EsaS4I, M.EsaS6I, M.EsaS7I, M.EsaS8I, M.EsaSS2P, M.EsaSS5P, M.EsaSS12P, M.EsaSS13P, M.EsaSS15P, M.EsaSS16P, M.EsaSS18P, M.EsaSS19P, M.EsaSS22P, M.EsaSS30P, M.EsaSS31P, M.EsaSS35P, M.EsaSS36P, M.EsaSS40P, M.EsaSS43P, M.EsaSS47P, M.EsaSS48P, M.EsaSS49P, M.EsaSS52P, M.EsaSS55P, M.EsaSS57P, M.EsaSS67P, M.EsaSS69P, M.EsaSS70P, M.EsaSS71P, M.EsaSS72P, M.EsaSS73P, M.EsaSS74P, M.EsaSS75P, M.EsaSS76P, M.EsaSS79P, M.EsaSS81P, M.EsaSS83P, M.EsaSS87P, M.EsaSS88P, M.EsaSS90P, M.EsaSS96P, M.EsaSS97P, M.EsaSS103P, M.EsaSS104P, M.EsaSS105P, M.EsaSS106P, M.EsaSS107P, M.EsaSS108P, M.EsaSS109P, M.EsaSS110P, M.EsaSS111P, M.EsaSS113P, M.EsaSS117P, M.EsaSS120P, M.EsaSS123P, M.EsaSS126P, M.EsaSS130P, M.EsaSS131P, M.EsaSS134P, M.EsaSS136P, M.EsaSS137P, M.EsaSS144P, M.EsaSS145P, M.EsaSS150P, M.EsaSS153P, M.EsaSS154P, M.EsaSS155P, M.EsaSS156P, M.EsaSS160P, M.EsaSS163P, M.EsaSS165P, M.EsaSS167P, M.EsaSS169P, M.EsaSS170P, M.EsaSS172P, M.EsaSS174P, M.EsaSS177P, M.EsaSS181P, M.EsaSS182P, M.EsaSS186P, M.EsaSS187P, M.EsaSS192P, M.EsaSS195P, M.EsaSS200P, M.EsaSS214P, M.EsaSS215P, M.EsaSS216P, M.EsaSS218P, M.EsaSS221P, M.EsaSS222P, M.EsaSS223P, M.EsaSS225P, M.EsaSS228P, M.EsaSS237P, M.EsaSS238P, M.EsaSS241P, M.EsaSS244P, M.EsaSS245P, M.EsaSS246P, M.EsaSS247P, M.EsaSS254P, M.EsaSS259P, M.EsaSS264P, M.EsaSS266P, M.EsaSS268P, M.EsaSS269P, M.EsaSS270P, M.EsaSS275P, M.EsaSS278P, M.EsaSS281P, M.EsaSS282P, M.EsaSS283P, M.EsaSS289P, M.EsaSS297P, M.EsaSS302P, M.EsaSS303P, M.EsaSS305P, M.EsaSS315P, M.EsaSS317P, M.EsaSS318P, M.EsaSS319P, M.EsaSS323P, M.EsaSS326P, M.EsaSS328P, M.EsaSS329P, M.EsaSS334P, M.EsaSS335P, M.EsaSS336P, M.EsaSS51DamP, M.EsaSS65DamP, M.EsaSS138DamP, M.EsaSS198DamP, M.Esp3I, M.Esp1396I, M.EspRB49DamP, M.FauI, M.FnuDI, M.FnuDII, M.FnuDIII, M.Fnu4HI, M.FnuVDamP, M.FokI, M.FseI, M.FspI, M.FssI, M.GmeORFC6P, M.GmeORFC16P, M.GsuI, M.GviDamP, M.H2I, M.HaeII, M.HaeIII, M.HapII, M.HduDamP, M1.HgaI, M2.HgaI, M.HgiAI, M.HgiBI, M.HgiCI, M.HgiCII, M.HgiDI, M.HgiDII, M.HgiEI, M.HgiGI, M.HhaI, M.HhaII, M.HheORF238P, M.HheORF1050P, M.HheORF1244P, M.HheORF1445P, M.Hin1II, M.HinB231ORFDP, M.HinHP1Dam, M.HinHP2Dam, M.HinPII, M.HincII, M.HindI, M.HindII, M.HindIII, M.HindV, M.HindDam, M.HinfI, M.HinfIII, M.HjaI, M.HpaI, M.HpaII, M1.HphI, M2.HphI, M.HpyI, M.Hpy8I, M.Hpy87AP, M.Hpy99I, M.Hpy99II, M.Hpy99III, M.Hpy99IV, M1.Hpy99V, M2.Hpy99VP, M.Hpy99VI, M.Hpy99VIII, M.Hpy99IX, M.Hpy99X, M.Hpy99XI, M.Hpy166IV, M.Hpy1781P, M.Hpy188I, M.Hpy188II, M.Hpy188III, M.Hpy788606P, M.Hpy788845P, M.Hpy788849P, M.Hpy789115P, M.Hpy789117P, M.Hpy789137P, M.Hpy789145P, M.Hpy790101P, M.Hpy959772P, M.HpyAI, M1.HpyAII, M2.HpyAII, M.HpyAIII, M.HpyAIV, M.HpyAV, M1.HpyAVI, M2.HpyAVI, M.HpyAVII, M.HpyAVIII, M.HpyAIX, M.HpyAX, M.Hpy87AI, M.HpyAORF263P, M.HpyAORF369P, M.HpyAORF481P, M.HpyAORF483P, M1.HpyCII, M2.HpyCII, M.HpyCH4IV, M.HpyCH4V, M.HpyCR2ORF1P, M.HpyCR2ORF3P, M1.HpyCR4RM1P, M2.HpyCR4RM1P, M.HpyCR9RM1P, M.HpyCR9RM2P, M.HpyCR14RM1P, M.HpyCR14RM2P, M.HpyCR15RM2P, M.HpyCR16RM1P, M.HpyCR29RM1P, M.HpyCR29RM2P, M.HpyCR35RM1P, M.HpyCR35RM2P, M1.HpyCR38RM1P, M2.HpyCR38RM1P, M.HpyCR38RM2P, M.HpyFl7I, M.Hpy99ORF430P, M.Hpy99ORF433P, M.Hpy99ORF846P, M.Hpy99ORF1012P, M.HspNORF1543P, M.KasI, M.KpnI, M.Kpn2I, M.KpnAI, M.KpnBI, M.Kpn19097DamP, M.Kpn19097Dam2P, M.Kpn19097ORFFP, M.Kpn2kI, M.Lci22RP, M.LinFORF11323P, M.LinFORF12222P, M.LinFORF12737P, M.LinLORF903P, M.LinLORF1547P, M.LinLORF2668P, M1.LlaAI, M2.LlaAI, M.LlaBI, M.LlaCI, M.LlaDI, M.LlaDII, M1.LlaDCHI, M2.LlaDCHI, M.LlaKR2I, M.LmoAP, M.LmoEORF470P, M.LmoFORF327P, M.Lmo19115ORF1P, M.Lsp1109I, M.MamI, M1.MboI, M2.MboI, M1.MboII, M2.MboII, M.Mca43617ORFAP, M.Mca43617ORFBP, M1.Mca43617ORFDP, M2.Mca43617ORFDP, M.Mca43617ORFJP, M.MfeI, M.MjaI, M.MjaII, M.MjaIII, M.MjaIVP, M.MjaV, M.MjaVI, M.MloORFmIr7520P, M.MluI, M.MlyI, M.MmaMORFC174P, M.MmaSORF735P, M.MmeI, M.MmeII, M.MmoORF950P, M.MmoORF3450P, M.MmyIP, M.MmySCORF186P, M.MmySCORF216P, M.MmySCORF950P, M1.MnlI, M2.MnlI, M.MpeORF1230P, M1.MpeORF1780P, M2.MpeORF1780P, M.MpeORF4940P, M.MpeORF9800P, M.MpuCORF430P, M.MscI, M.MseI, M.MsmChe9cORF76P, M.MsmChe9cORF77P, M.MsmChe9cORF80P, M.MsmcdP, M.MsmomegaORF127P, M.MspI, M.MspAII, M.MspSD10I, M.MthFI, M.MthTI, M.MthZI, M.MunI, M.MvaI, M.Mva12691, M.MwoI, M.NaeI, M.NarAORFC306P, M.NcoI, M.NdeI, M.NdeII, M.Ngo18785P, M.Ngo185840P, M.Ngo185841P, M.NgoAI, M.NgoAII, M.NgoAIII, M.NgoAIV, M.NgoAV, M.NgoAVIIP, M.NgoAXIP, M.NgoAORFC708P, M1.NgoAORFC717P, M2.NgoAORFC717P, M.NgoBI, M.NgoBII, M.NgoBIIIP, M.NgoBIVP, M.NgoBV, M1.NgoBVIII, M2.NgoBVIII, M.NgoBIX, M.NgoBXII, M.NgoDIII, M.NgoEI, M.NgoFVII, M.NgoGI, M.NgoGII, M.NgoGIII, M.NgoGIVP, M.NgoGV, M.NgoHIP, M.NgoHIIP, M.NgoHIIIP, M.NgoHIVP, M.NgoHVP, M.NgoHVIP; M.NgoHVIIP, M.NgoHVIII, M.NgoKVIP, M.NgoLIP, M.NgoLII, M.NgoLIIIP, M.NgoLIVP, M.NgoLVP, M.NgoMI, M.NgoMII, M.NgoMIII, M.NgoMIV, M.NgoMV, M.NgoMVIII, M.NgoMXV, M.NgoNIP, M.NgoNII, M.NgoNIIIP, M.NgoNIVP, M.NgoNVP, M.NgoPIP, M.NgoPII, M.NgoPIII, M.NgoPIVP, M.NgoPVP, M.NgoQIP, M.NgoQIIP, M.NgoQIIIP, M.NgoQIVP, M.NgoQVP, M.NgoSIP, M.NgoSII, M.NgoSIIIP, M.NgoSIVP, M.NgoSVP, M.NgoTIP, M.NgoTII, M.NgoTIIIP, M.NgoTIVP, M.NgoTVP, M.Ngo125VIIP, M.NlaI, M.NlaIII, M.NlaIV, M.NlaX, M.NlaL17ORFAP, M.NmaPhiCh1I, M.NmeAORF1453P, M.NmeAORF1500P, M1.NmeBI, M2.NmeBI, M.NmeBF13P, M.NmeBORF1033P, M.NmeBORF1290P, M.NmeSI, M.NmeST1117ORF1P, M.NmepNLE1P, M.NpuORFC221P, M.NpuORFC222P, M.NpuORFC224P, M.NpuORFC226P, M.NpuORFC228P, M.NpuORFC230P, M.NpuORFC231P, M.NpuORFC234P, M.NsiI, M.NspI, M.NspIII, M.NspV, M.NspHI, M.OihORF3333P, M.OihORF3336P, M.OkrAI, M.Pac25I, M.PaeI, M.PaeIMORF3201P, M.PaeMSHORF1P, M.Pae2164ORF7P, M.PaeR7I, M.PflMI, M.PgiI, M.PhaI, M.PhiBssHII, M.PhiMx8I, M.Phi3TI, M.Phi3TII, M.PhoI, M.PhoII, M.PhoWORFBP, M.PhsOYDam1 P, M.PhsOYDam2P, M.PhsOYDam3P, M.PhsOYDam4P, M.PhsOYDam5P, M.PleI, M.PleLFBORF8P, M.PluTDamP, M.PluTDcmP, M.PluTORF600P, M.PluTORF2710P, M.PluTORF2942P, M.Pmi16525DamP, M.PmiI 6525Dam2P, M.Pmi16525ORFDP, M.PmuADam, M.PmuDam, M.Ppu21I, M.Ppu111I, M.Ppu1253I, M.PpuMI, M.PshAI, M.PspGI, M.PspPI, M.PstI, M.PvuI, M.PvuII, M.PvuRts1DamP, M.PvuRts1Dam2P, M.RcoORF690P, M.ReuORF325P, M.Rho11sI, M.Rho11sII, M.Rle39BI, M.RmeADam, M.RpaORF1026P, M.RpapRPA4P, M.Rrh4273I, M.RruMORFS5P, M.RruMORFS15P, M.RsaI, M.RshI, M.RshIII, M.RsrI, M.RsrII, M.SPBetaI, M.SsrII, M.SacI, M.SacII, M.SalI, M2.5apI, M.Sau96I, M.Sau3239I, M.Sau6782I, M.Sau3AI, M.SauLPI, M.SbaI, M.SbfI, M.Sbo13I, M.ScaI, M1.5crF1, M2.5crFI, M.SduI, M.SenPI, M.SenPhiE15P, M.SenPhiE15DamP, M.SenpCI, M.SeqORFC57P, M.SeqORFC272P, M.SeqORFC448P, M.SfaNI, M.SfeI, M.SfiI, M.Sfl2DamP, M.Sfl2DcmP, M.Sfl2ORF3300P, M.SflSf6DamP, M.SfITDamP, M.SfITDcmP, M.SfITORF3517P, M.Sfl2al, M.SfoI, M.Sho27844P, M.SinI, M.SmaI, M.SmaII, M.SmapR478DcmP, M.SmapR478ORF272P, M.SmelP, M1.SmuUORF504P, M2.5muUORF504P, M.SnaBI, M.SonDamP, M.SonORF4P, M.SpeI, M.SphI, M.Spn526P, M.Spn6BI, M1.Spn19FORF24P, M2.5pn19FORF24P, M.Spn19FORF927P, M.SpnHGORF4P, M.SpnORF1431 P, M.SpnORF1849P, M.SpnRORF1287P, M.SpomI, M.SptAI, M.SscL1I, M.Sse9I, M.SsIII, M.SsoI, M.SsoII, M.Ssp68031, M.Ssp6803ORF729P, M.Ssp6803ORF1803P, M.SspPhiBtl P, M.SssI, M.SstI, M.Ssu211I, M.Ssu2121, M1.Ssu24791, M2.5su2479I, M1.Ssu4109I, M2.5su4109I, M1.Ssu4961I, M2.5su4961I, M1.Ssu8074I, M2.5su8074I, M1.Ssu11318I, M2.5su11318I, M1.SsuDAT1I, M2.5suDAT1I, M.Sth368I, M.SthSt81P, M.StsI, M.StyI, M.StyCDamP, M.StyCDam2P, M.StyCDam3P, M.StyCDam4P, M.StyCDcmP, M.StyD4I, M.StyDam, M.StyDam2P, M.StyDam3P, M.Sty1344Dam, M.Sty14028Dam, M.StyHCM1ORF187P, M.StyLTI, M.StyLTIII, M.StyLT2Dam, M.StyLT2DcmP, M.StyLT2FelsDamP, M.StyR27ORF154P, M.StySJI, M.StySKI, M.StySPI, M.StySQI, M.StySopEDamP, M.StyTDamP, M.StyTDam2P, M.StyTDam3P, M.StyTDam4P, M.StyTDcmP, M.SuaI, M.TaeII, M.TaqI, M.TdeII, M.TdeIII, M.TdeORF706P, M.TelBORF1578P, M.TelBORF1640P, M.TelBORF1878P, M1.TerORFS1P, M2.TerORFS1P, M.TerORFS14P, M.TerORFS18P, M.TerORFS62P, M.TerORFS122P, M.TfiTok6A1I, M.ThaI, M.ThaII, M.ThaIII, M.TliI, M.TmaI, M.TpaI, M.TrsKTI, M.TrsSI, M.TrsTI, M.TseI, M.Tsp32I, M.Tsp45I, M.Tsp509I, M.TspRI, M.Tth111I, Tth111II, M.TthHB8I, M.TthHB27P, M.TthHB27ORF41P, M.TvoORF849P, M.TvoORF1192P, M.TvoORF1400P, M.TvoORF1413P, M.TvoORF1416P, M.TwhORF771P, M.TwhTORF783P, M.Uba580P, M.Ucrl P, M.Van91II, M.VchADamP, M.Vch569BdamP, M.VchO395Dam, M.VchKl39I, M.VpaRDamP, M.VspI, M.VvuDamP, M.VvuYDamP, M.WsuORF1405P, M.WsuORF1930P, M.XamI, M.XaxCORF2436P, M.XbaI, M.XcmI, M.XcyI, M.XfaAORFC345P, M.XfaAORFC348P, M.XfaOORFC725P, M.XfaORF1804P, M.XfaTORF577P, M.XfaTORF1062P, M.XfaTORF1607P, M.XhoI, M.XhoI, M.XmaI, M.XmaIII, M.XmnI, M.XorII, M.XphI, M.YenI, M.YenSDamP, M.YenSORFC666P, M.YenWI, M.YpeDamP, M.YpeKDamP, M.YpeKORF2224P, M.YpeKORF3792P, M.YpeMDamP, M.YpeMORF1932P, M.YpeMORF3790P, M.YpeORF391P, M.YpeORF2088P, and M.YpsDam.

In a more preferred embodiment of the present invention, the methyltransferase is selected from the group consisting of the DNA methyltransferases M.TaqI, M.HhaI, M.BcnIB (M2.BcnI), M.SssI, M.BseCI, M.RsrI, M2.BfiI (M.BfiC2), and M2.Eco31I, or a derivative thereof.

The present invention also relates to a kit comprising a compound (I) of the present invention. The various components of the kit may be packed in one or more containers, optionally dissolved in suitable buffer for storage. A leaflet with instructions for use may be added.

In a preferred embodiment of the present invention, the kit of the present invention further comprises a methyltransferase as defined in the present invention.

The present invention also relates to a kit comprising a complex of the present invention.

The present invention also relates to a pharmaceutical composition comprising a compound (I) of the present invention or a complex of the present invention and optionally a pharmaceutically acceptable carrier.

The present invention also relates to a diagnostic composition comprising a compound (I) of the present invention or a complex of the present invention. According to one embodiment, the diagnostic composition is a liquid composition. The preferred solvent of the diagnostic composition is aqueous in nature. In addition, the composition may contain other ingredients or carriers for modifying or maintaining the pH, osmolarity, viscosity, clarity, color, sterility, stability, rate of dissolution, or odor of the formulation. Similarly, the composition may contain still other pharmacologically acceptable ingredients for modifying or maintaining the stability, rate of dissolution, release, or absorption of the diagnostic composition. Once the diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to use.

The present invention also relates to the use of a compound (I) of the present invention or a mixture thereof for modifying a target molecule. Typical uses are methods according to the teaching of the present invention such as the methods described herein.

In a preferred embodiment of the present invention, the modification of the target molecule is achieved by using a compound (I) of the present invention or mixtures thereof as a cofactor of a methyltransferase which transfers part of the compounds onto the target molecule.

In a preferred embodiment of the present invention, the target molecule is a nucleic acid molecule, a polypeptide optionally modified in a sequence-specific manner, a carbohydrate or a small molecule.

In a preferred embodiment of the present invention, the nucleic acid molecule is DNA, RNA or a hybrid thereof, more preferably the DNA or RNA molecule is modified in a sequence-specific manner.

In another more preferred embodiment of the present invention, the small molecule is selected from phospholipids, amino acids, hormones, nucleotides, nucleosides and derivatives thereof.

In another more preferred embodiment of the present invention, the methyltransferase is a DNA methyltransferase as defined above.

The present invention also relates to a method for the preparation of a modified target molecule comprising the incubation of the target molecule with a compound (I) of the present invention in the presence of a methyltransferase which is capable of using the compound as a cofactor and under conditions which allow for the transfer of part of the compounds onto the target molecule.

In a preferred embodiment of the present invention, the target molecule is a nucleic acid molecule, a polypeptide, a carbohydrate, or a small molecule or a complex between them.

In a more preferred embodiment of the present invention, the small molecule is a phospholipid, an amino acid, a hormone, a nucleotide, a nucleoside or a derivative thereof.

In a more preferred embodiment of the present invention, the polypeptide is modified in a sequence-specific manner.

In a more preferred embodiment of the present invention, the DNA or RNA molecule is modified in a sequence-specific manner.

In another more preferred embodiment of the present invention, the modification results from the transfer of a group onto the target molecule which is suitable as a label and which allows for the identification of the labeled molecule among other unlabeled molecules. Finally, in a more preferred embodiment of the present invention, the label is selected from fluorophores, fluorescence quenchers, affinity tags, spin labels, mass tags, radioactive or stable rare isotopes, chromophors and a detectable nanoparticle.

The present invention also relates to a method for detecting sequence-specific methylation in a biomolecule, comprising: (a) contacting a biomolecule with an S-adenosyl-L-methionine-dependent methyltransferase in the presence of a detectable cofactor of said methyltransferase; and (b) detecting whether the recognition site of said methyltransferase has been modified with the cofactor or a derivative thereof, wherein modification of the recognition site of said methyltransferase is indicative of an absence of methylation at said recognition site, wherein said cofactor is the compound of formula (I) of the present invention or a derivative thereof, which is described herein above in detail.

The term "biomolecule" means DNA, RNA or (poly)peptide. The term "(poly)peptide" refers alternatively to peptide or to polypeptide. Peptides conventionally are covalently linked amino acids of up to 30 residues, whereas polypeptides (also referred to as "proteins") comprise 31 and more amino acid residues. Preferably, the biomolecule is chromosomal or genomic DNA.

The term "contacting a biomolecule with a methyltransferase" means bringing into contact the biomolecule with the methyltransferase. Generally, this may be done by adding the methyltransferase to a sample containing the biomolecule. Alternatively, the sample containing the biomolecule may be added to a solution containing the methyltransferase. The skilled person knows that particular buffer conditions might be required for optimal enzyme activity. These conditions are either known to the skilled person or can be obtained by studying enzyme activity under various assay conditions.

Normally, the biomolecule is contacted by the methyltransferase in the presence of a cofactor of the methyltransferase. Preferably, said cofactor is the compound of formula (I) or a derivative thereof, which is described herein above in detail.

The term "methyltransferase" refers to enzymes normally transferring the activated methyl from S-adenosyl-L-methionine (AdoMet) onto their substrate. Preferably, the methyltransferase is an enzyme capable of methylating DNA, RNA or (poly)peptides. More preferably, the methyltransferase is a DNA methyltransferase selected from M.TaqI, M.HhaI, M.BcnIB (M2.BcnI), M.SssI, M.BseCI, M.RsrI, M2.BfiI (M.BfiC2) and M2.Eco3I or a derivative thereof.

The term "detecting whether the recognition sequence of said methyltransferase has been modified with the cofactor or a derivative thereof" means assessing whether the cofactor of formula (I) or a derivative thereof is attached to the biomolecule. Preferably, detection methods involve identifying the particular residue, within the recognition sequence of the methyltransferase, modified by the cofactor or the derivative thereof. Said derivative may be any compound resulting from the reaction between the compound of formula (I) or a derivative thereof and the biomolecule.

The term "recognition sequence" refers to the particular sequence or structure within the biomolecule recognized by the methyltransferase. In case the methyltransferase is a DNA methyltransferase, the recognition sequence may comprise 2, 3, 4, 5, 6, or 8 nucleotides or nucleotide pairs. As used herein, the recognition sequence normally comprises the acceptor site for the compound of formula (I) of the present invention or the derivative thereof. The teaching of the present invention allows sequence-specific labeling in a methylation-dependent manner. DNA labeling of cytosine residues located in so-called CpG islands is a particular aspect of the present invention, as this allows to assess the methylation status of human chromosomal DNA. Therefore, the methods of the present invention are particularly useful for, but not limited to, diagnosing diseases associated with an altered methylation status of the chromosomal DNA. It should also be useful to access the methylation status of DNA from other sources as well as the methylation status of RNA or (poly)peptides. In addition, the cofactor of formula (I) or a derivative thereof in complex with a methyltransferase could be used to sequence-specifically label DNA, RNA or (poly)peptides which should be useful for various applications in biochemistry, molecular biology, gene therapy and nanobiotechnology. Furthermore, the cofactor of formula (I) or a derivative thereof could be used to find new methylation targets for methyltransferases.

In a preferred embodiment of the present invention, said biomolecule is a nucleic acid molecule or a (poly)peptide. Nucleic acid molecules shall be understood to encompass DNA and RNA. Preferably, DNA is chromosomal or genomic DNA. The biomolecule may be of any length. The term "chromosomal DNA" also encompasses fragments of a chromosome. Preferably, said fragment has a length of up to 500 nucleotides (nt), 1 kilobase (kb), 2 kb, 3 kb, 4 kb, 5 kb, 6 kb, 7 kb, 8 kb, 9 kb, 10 kb or even longer. However, also encompassed by the term chromosomal DNA are short fragments with a length of up to 5 nt, 10 nt, 15 nt, 20 nt, 25 nt, 30 nt, 35 nt, 40 nt, 45 nt, 50 nt, 100 nt, 200 nt, 300 nt, 400 nt, or 500 nt.

In yet another preferred embodiment of the present invention, said step (a) is performed in vitro, with cell extracts or in vivo. Generally, suitable reaction conditions for treatment with restriction enzymes and DNA methyltransferases are known to the skilled person and are documented, for example, in standard textbooks of molecular biology (see e.g. Sambrook et al., "Molecular Cloning, A Laboratory Manual"; ISBN: 0879695765, CSH Press, Cold Spring Harbor, 2001). Suitable conditions for cofactor labeling mediated by M.SssI variant Q142A are, e.g. 300 µM of the compound of formula (I) or a derivative thereof, 31.3 fmol double-stranded DNA, 73 µmol M.SssI variant Q142A in buffer (10 mM Tris hydrochloride, 50 mM sodium chloride, 1 mM dithiothreitol, pH 7.9). Incubation may be performed at 37° C. for 4 h. When the methods of the present invention are carried in vitro a biological sample is isolated from an individual prior to analysis. The term "biological sample" relates to the specimen taken from the individual. Preferably, said specimen is taken from hair, skin, mucosal surfaces, body fluids, including blood, plasma, serum, urine, saliva, sputum, tears, liquor cerebrospinalis, semen, synovial fluid, amniotic fluid, breast milk, lymph, pulmonary sputum, bronchial secretion or stool.

The individual may be a human or an animal. Preferably, the individual is avian including turkey or hen, or the individual is a mammal including human, primate, rat, mouse, guinea pig, pig, cattle, cat or rabbit.

In a more preferred embodiment of the present invention, said nucleic acid molecule is DNA. Preferably, said DNA is chromosomal DNA.

In another more preferred embodiment of the present invention, the method further comprises prior to step (a) a step of treating the DNA with a restriction enzyme. Restriction enzymes may be selected from the group consisting of R.AatII, R.AccI, R.Acc65I, R.AciI, R.AclI, R.AfeI, R.AflII, R.AflIII, R.AgeI, R.AhdI, R.AluI, R.AlwI, R.AlwNI, R.ApaI, R.ApaLI, R.ApoI, R.AscI, R.AseI, R.AsiSI, R.AvaI, R.AvaII, R.AvrII, R.BaeI, R.BamHI, R.BanI, R.BanII, R.BbsI, R.BbvI, R.BbvCI, R.BceAI, R.BcgI, R.BciVI, R.BclI, R.BfaI, R.BfrBI, R.BfuAI, R.BglI, R.BglII, R.BlpI, R.Bme1580I, R.BmgBI, R.BmrI, R.BpmI, R.BsaI, R.BsaAI, R.BsaBI, R.BsaHI, R.BsaJI, R.BsaWI, R.BsaXI, R.BseRI, R.BsgI, R.BsiEI, R.BsiHKAI, R.BsiWI, R.BslI, R.BsmI, R.BsmAI, R.BsmBI, R.BsmFI, R.BsoBI, R.Bsp1286I, R.BspCNI, R.BspDI, R.BspEI, R.BspHI, R.BspMI, R.BsrI, R.BsrBI, R.BsrDI, R.BsrFI, R.BsrGI, R.BssHII, R.BssKI, R.BssSI, R.BstAPI, R.BstBI, R.BstEII, R.BstF5I, R.BstNI, R.BstUI, R.BstXI, R.BstYI, R.BstZ17I, R.Bsu36I, R.BtgI, R.BtrI, R.BtsI, R.Cac8I, R.ClaI, R.DdeI, R.DpnI, R.DpnII, R.DraI, R.DraIII, R.DrdI, R.EaeI, R.EagI, R.EarI, R.EciI, R.EcoNI, R.EcoO109I, R.EcoRI, R.EcoRV, R.FauI, R.Fnu4HI, R.FokI, R.FseI, R.FspI, R.HaeII, R.HaeIII, R.HgaI, R.HhaI, R.HinP1I, R.HincII, R.HindIII, R.HinfI, R.HpaI, R.HpaII, R.HphI, R.Hpy99I, R.Hpy188I, R.Hpy188III, R.HpyCH4III, R.HpyCH4IV, R.HpyCH4V, R.KasI, R.KpnI, R.MboI, R.MboII, R.MfeI, R.MluI, R.MlyI, R.MnlI, R.MscI, R.MseI, R.MslI, R.MspI, R.MspA1I, R.MwoI, R.NaeI, R.NarI, R.NciI, R.NcoI, R.NdeI, R.NgoMIV, R.NheI, R.NlaIII, R.NlaIV, R.NotI, R.NruI, R.NsiI, R.NspI, R.PacI, R.PaeR7I, R.PciI, R.PflFI, R.PflMI, R.PleI, R.PmeI, R.PmlI, R.PpuMI, R.PshAI, R.PsiI, R.PspGI, R.PspOMI, R.PstI, R.PvuI, R.PvuII, R.RsaI, R.RsrII, R.SacI, R.SacII, R.SalI, R.SapI, R.Sau96I, R.Sau3AI, R.SbfI, R.ScaI, R.ScrFI, R.SexAI, R.SfaNI, R.SfcI, R.SfiI, R.SfoI, R.SgrAI, R.SmaI, R.SmlI, R.SnaBI, R.SpeI, R.SphI, R.SspI, R.StuI, R.StyI, R.SwaI, R.TaqI, R.TfiI, R.TliI, R.TseI, R.Tsp45I, R.Tsp509I, R.TspRI, R.Tth111I, R.XbaI, R.XcmI, R.XhoI, R.XmaI and R.XmnI.

In yet another more preferred embodiment of the present invention, said DNA molecule is immobilized on a solid support. Solid supports that may be employed in accordance with the invention include filter material, chips, wafers, microtiter plates. Immobilization on the solid support may be achieved by different means including covalent coupling to an activated surface or by hybridization to nucleic acid molecules.

In another more preferred embodiment of the present invention said DNA molecule is coupled to the solid support by hybridizing the DNA molecule to an oligonucleotide which is attached to said solid support. Hybridization conditions may be of low, intermediate or high stringency. The term "stringent conditions", as used herein, is well known to the skilled artesian and corresponds to conditions of high stringency. Appropriate stringent hybridization conditions for each sequence may be established by a person skilled in the art by modifying parameters such as temperature, composition of the nucleic acid molecules, salt conditions etc.; see, for example, Sambrook et al., "Molecular Cloning, A Laboratory Manual"; ISBN: 0879695765, CSH Press, Cold Spring Harbor, 2001 or Higgins and Hames (eds.), "Nucleic acid hybridization, a practical approach", IRL Press, Oxford 1985, see in particular the chapter "Hybridization Strategy" by Britten & Davidson, 3 to 15. Stringent hybridization conditions are, for example, conditions comprising overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/mL denatured, sheared salmon sperm DNA, followed by washing the filters in 0.1×SSC at about 65° C. Other stringent hybridization conditions are for example 0.2×SSC (30 mM NaCl, 3 mM sodium citrate, pH 7) at 65° C. In addition, to achieve even lower stringency, washes performed following stringent hybridization can be done at higher salt concentrations (e.g. 5×SSC). Note that variations in the above conditions may be accomplished through the inclusion and/or substitution of alternate blocking reagents used to suppress background in hybridization experiments. Typical blocking reagents include, but are not limited to, Denhardt's reagent, BLOTTO, heparin, denatured salmon sperm DNA, and commercially available proprietary formulations. The inclusion of specific blocking reagents may require modification of the hybridization conditions described above, due to problems with compatibility. Also contemplated are hybridization conditions of lower stringency. Changes in the stringency of hybridization and signal detection are, for example, accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3 M NaCl, 0.2 M NaH$_2$PO$_4$, 0.02 M EDTA, pH 7.4), 0.5% SDS, 30% formamide, 100 µg/mL salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

In another more preferred embodiment of the present invention, the methyltransferase is an orphan DNA methyltransferase or part of a bacterial restriction modification system.

In yet another more preferred embodiment of the present invention, said methyltransferase is selected from M.TaqI, M.HhaI, M.BcnIB (M2.BcnI), M.SssI, M.BseCI, M.RsrI, M2.BfiI (M.BfiC2) and M2.Eco31I or a derivative thereof. The term "M.HhaI" refers to the DNA methyltransferase deposited in the Swissprot database under accession number PO5102. The term "M.TaqI" refers to the DNA methyltransferase deposited in the Swissprot database under accession number P14385. The term "M.BseCI" refers to the DNA methyltransferase deposited in the Swissprot database under accession number P43423. However, any other methyltransferase with the same sequence specificity, i.e. with the same recognition sequence, or a reduced sequence specificity comprising only part of the recognition sequence of M.TaqI, M.HhaI, M.BcnIB (M2.BcnI), M.SssI, M.BseCI, M.RsrI, M2.BfiI (M.BfiC2) and M2.Eco31I could be useful for the methods of the present invention.

In another more preferred embodiment of the present invention, (a) the compound of formula (I) of the present invention or a derivative thereof blocks restriction enzyme cleavage at or near the recognition sequence of the DNA methyltransferase; and (b) methylation is detected by testing whether the modification of the DNA by said compound blocks cleavage mediated by a restriction enzyme at or near said recognition sequence. Any restriction enzyme and DNA methyltransferase mentioned in the present invention may be used when performing this method.

It has been observed by the inventor of the present invention that the presence of the compound of formula (I) of the present invention at the acceptor site of the recognition sequence blocks DNA cleavage by restriction enzymes with an overlapping or the same recognition sequence. Blocking restriction enzyme cleavage, as used herein, means preventing the restriction enzyme from cutting the DNA strands. Without being bound to theory, it is assumed that steric hindrance blocks accessibility of the recognition sequence so that the restriction enzyme can no longer bind to its target sequence in a productive manner. This observation can be exploited by assays which involve an initial labeling step with the compound of the present invention and a subsequent cleavage step with a restriction enzyme. Naturally, the choice of the restriction enzyme depends on the particular DNA methyltransferase employed in the labeling step. As a general guideline, the recognition sequence of the restriction enzyme should be nearby the modified base. Preferably, the recognition sequence of the restriction enzyme comprises the modified base. More preferably, the recognition sequence of the DNA methyltransferase and the recognition sequence of the restriction enzyme are the same. The choice of particular combinations of restriction enzyme and DNA methyltransferase is obvious to the skilled person and needs no further explanation. Moreover, the labeling reaction performed by the DNA methyltransferase and the restriction enzyme cleavage may be performed under standard conditions.

In yet another more preferred embodiment of the present invention, (a) the compound of formula (I) of the present invention or a derivative thereof interferes with nucleic acid amplification at the recognition site of the methyltransferase; and (b) methylation is detected by testing whether amplification of the nucleic acid molecule at the recognition site of the methyltransferase has been retarded.

Retardation of amplification may be achieved by interfering with primer binding or with strand elongation during an amplification reaction.

The term "amplification" or "amplify" means increase in copy number. The person skilled in the art knows various methods to amplify nucleic acid molecules, these methods may also be used in the present invention's method of diagnosing. Amplification methods include, but are not limited to, "polymerase chain reaction" (PCR), "ligase chain reaction" (LCR, EPA320308), "cyclic probe reaction" (CPR), "strand displacement amplification" (SDA, Walker et al., (1992) Nucleic Acid Res. 7, 1691-1696), "transcription based amplification systems" (TAS, Kwoh et al., (1989) Proc. Nat. Acad. Sci. USA 86, 1173; Gingeras et al., PCT Application WO 88/10315). Preferably, amplification of DNA is accomplished by using polymerase chain reaction (PCR) [Methods in Molecular Biology, Vol. 226 (Bartlett and Stirling, eds.): PCR protocols, 2nd edition; PCR Technology: Principles and Applications for DNA Amplification (Erlich, ed.), New York 1992; PCR Protocols: A guide to methods and applications (Innis et al., eds.), Academic Press, San Diego 1990]. Nucleic acid amplification methods may be particularly useful in cases when the sample contains only minute amounts of nucleic acid. If said nucleic acid is RNA, an RT-PCR might be performed. Subsequently, another amplification step involving PCR may be performed. Alternatively, if said nucleic acid contained in the sample is DNA, PCR may be performed.

The PCR, generally, consists of many repetitions of a cycle which consists of: (a) a denaturing step, which melts both strands of a DNA molecule; (b) an annealing step, which is aimed at allowing the primers to anneal specifically to the melted strands of the DNA molecule; and (c) an extension step, which elongates the annealed primers by using the information provided by the template strand. Generally, PCR can be performed for example in a 50 µL reaction mixture containing 5 µL of 10×PCR buffer with 1.5 mM $MgCl_2$, 200 µM of each deoxynucleoside triphosphate, 0.5 µL of each primer (10 µM), about 10 to 100 ng of template DNA and 1 to 2.5 units of Taq DNA Polymerase. The primers for the amplification may be labeled or be unlabeled. DNA amplification can be performed, e.g. with a model 2400 thermal cycler (Applied Biosystems, Foster City, Calif.): 2 min at 94° C., followed by 35 cycles consisting of annealing (30 s at 50° C.), extension (1 min at 72° C.), denaturing (10 s at 94° C.) and a final annealing step at 55° C. for 1 min as well as a final extension step at 72° C. for 5 min. However, the person skilled in the art knows how to optimize these conditions for the amplification of specific nucleic acid molecules or to scale down or increase the volume of the reaction mix.

A further method of nucleic acid amplification is the "reverse transcriptase polymerase chain reaction" (RT-PCR). This method is used when the nucleic acid to be amplified consists of RNA. The term "reverse transcriptase" refers to an enzyme that catalyzes the polymerization of deoxyribonucleoside triphosphates to form primer extension products that are complementary to a ribonucleic acid template. The enzyme initiates synthesis at the 3' end of the primer and proceeds toward the 5' end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. Suitable polymerases for use with a DNA template include, for example, *E. coli* DNA polymerase I or its Klenow fragment, T.sub.4 DNA polymerase, Tth polymerase, and Taq polymerase, a heat-stable DNA polymerase isolated from *Thermus aquaticus* and developed and manufactured by Hoffmann-La Roche and commercially available from Perkin Elmer. The latter enzyme is widely used in the amplification and sequencing of nucleic acids. The reaction conditions for using Taq DNA polymerase are known in the art and are described, e.g. in: PCR Technology, Erlich (1989, Stockton Press, New York; or in: Innis, Gelfand, Sninsky and White. 1990, PCR Protocols: A guide to methods and applications. Academic Press, New York. High-temperature RT provides greater primer specificity and improved efficiency. Copending U.S. patent application Ser. No. 07/746,121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT reaction can be performed, for example, in a 20 µL reaction mix containing: 4 µL of 5×ANV-RT buffer, 2 µL of oligo dT (100 µg/mL), 2 µL of 10 mM dNTPs, 1 µL total RNA, 10 units of AMV reverse transcriptase, and $H_2O$ to 20 µL final volume. The reaction may be, for example, performed by using the following conditions: The reaction is held at 70° C. for 15 minutes to allow for reverse transcription. The reaction temperature is then raised to 95° C. for 1 minute to denature the RNA-cDNA duplex. Next, the reaction temperature undergoes two cycles of 95° C. for 15 seconds and 60° C. for 20 seconds followed by 38 cycles of 90° C. for 15 seconds and 60° C. for 20 seconds. Finally, the reaction temperature is held at 60° C. for 4 minutes for the final extension step, cooled to 15° C., and held at that temperature until further processing of the amplified sample.

The term "primer" or "oligonucleotide", as used throughout the invention, refers to a short nucleic acid molecule from about 8 to about 30, eventually to about 50 nucleotides in length, whether natural or synthetic, capable of acting as a point of initiation of nucleic acid synthesis under conditions in which synthesis of a primer extension product complementary to a template nucleic acid strand is induced, i.e., in the presence of four different nucleoside triphosphates or analogues thereof and an agent for polymerisation (i.e., DNA polymerase or reverse transcriptase) in an appropriate buffer and at a suitable temperature. Preferably, a primer is a single-stranded oligodeoxyribonucleotide. The appropriate length of a primer depends on the intended use of the primer but typically ranges for PCR primers and primers used in sequencing reactions from 10 to 25 nucleotides. Short primer molecules generally require cooler temperatures to form sufficiently stable hybrid complexes with the template. A primer need not reflect the exact sequence of the template but must be sufficiently complementary to hybridize specifically with a template, provided its ability to mediate amplification is not compromised. "Hybridize" refers to the binding of two single-stranded nucleic acids via complementary base pairing, i.e. A to T (in RNA: U), G to C. The term "primer pair" refers to two primers that hybridize with the plus and minus strand, respectively, of a double-stranded nucleic acid molecule, and allow the amplification of e.g. DNA fragments, as for example in a PCR reaction. A primer can be labeled, if desired, by incorporating a compound detectable by spectroscopic, photochemical, biochemical, immunochemical, or chemical means. For example, useful labels include, but are not limited to, fluorescent dyes, electron-dense reagents, biotin, or small peptides for which antisera or monoclonal antibodies are available. A label can also be used to "capture" the primer, so as to facilitate a selection of amplified nucleic acid or fragments thereof. Carboxyfluorescein (FAM) and 6-carboxy-X-rhodamine (ROX) are preferred labels. However, other preferred labels include fluorochromes, e.g. fluorescein isothiocyanate (FITC), Texas Red, phycoerythrin, allophycocyanin, 6-carboxyfluorescein (6-FAM), 2',7'-dimethoxy-4',5'-dichloro-6-carboxyfluorescein (JOE),5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc.

The label may also be a two stage system, where the primer is conjugated to biotin, haptens, etc. having a high affinity binding partner, e.g. avidin, specific antibodies, etc., where the binding partner is conjugated to a detectable label. The label may be conjugated to one or both of the primers.

During said method for diagnosing, a step of nucleic acid sequencing may be performed. Any methods known in the art may be used for sequencing. Preferably, the nucleic acid sequence is determined by a method based on the sequencing techniques of Sanger or Maxam/Gilbert (see for example: Methods in Molecular Biology, Vol. 167 (Graham and Hill, eds.): DNA sequencing protocols. 2nd edition, 2001; Galas and McCormack, Genomic Technologies: Present and Future. Caister Academic Press, Wymondham, Uk., 2002).

In a preferred embodiment of the present invention, PCR is real-time PCR. In another preferred embodiment of the present invention, nucleic acid amplification is carried out by real-time PCR.

In yet another more preferred embodiment of the present invention, (a) the compound of formula (I) of the present invention or a derivative thereof contains a fluorescent label; and (b) methylation is detected by measuring the presence or amount of fluorescence in said nucleic acid molecule. Said compound of formula (I) of the present invention or a derivative thereof may be labeled with any of the fluorescent labels mentioned in the present invention or known to the skilled artisan. In accordance with the present invention, Alexa, BODIPY, bimane, coumarin, Cascade blue, dansyl, dapoxyl, fluorescein, mansyl, MANT, Oregon green, pyrene, rhodamine, Texas red, TNS, fluorescent nanocrystals (quantom dots), a cyanine fluorophore and derivatives thereof are particularly preferred labels.

"Measuring the presence or amount of fluorescence" means assessing whether or not or how much fluorescence can be detected by fluorescence spectroscopy.

In another more preferred embodiment of the present invention, (a) nucleic acid molecules modified at the methyltransferase recognition sequence are purified by affinity purification; and (b) the compound of formula (I) of the present invention or a derivative thereof contains an affinity tag.

Nucleic acid molecules may be purified by using a compound capable of specifically binding to the label of compound of formula (I) of the present invention or a derivative thereof. In that case the label corresponds to or comprises an affinity tag. An affinity tag may be combined with one or more fluorescent labels. Preferably, the compound capable of binding to the label or affinity tag is an antibody, a protein, a peptide or an aptamer, wherein binding of these compounds is specific. The affinity tag may be an epitope such as the flag-tag, c-myc-tag, HA-tag, digoxygenin or dinitrophenol. Alternatively, the affinity tag may be an artificial peptide such as the His tag. "His tags" may be selected from $His_4$, $His_5$, $His_6$, $His_7$, $His_8$, $His_9$, $His_{10}$, $His_{11}$, $His_{12}$, $His_{13}$, $His_{14}$, $His_{15}$. Moreover, the affinity tag may be biotin, strep-tag, glutathione, nickel-nitrilotriacetic acid (NTA) or maltose. If the affinity tag is a "His tag", nickel coupled to a solid support may be used for purification. If the affinity tag is an epitope, an antibody-affinity coupled to a solid support may be used for purification. If the affinity tag is biotin or strep-tag, avidin or streptavidin or the like bound to a solid support may be used for purification. If the affinity tag is glutathione, glutathione transferase (GST) bound to a solid support may be used for purification. If the affinity tag is maltose, maltose binding protein bound to a solid support may be used for purification. If the affinity tag is nickel-nitrilotriacetic acid (NTA), a peptide containing several histidine residues bound to a solid support may be used for purification.

Affinity purification generally involves the separation of molecules in solution (mobile phase) based on differences in binding interaction with a ligand that is immobilized to a stationary material (solid phase). A support or matrix in affinity purification is any material to which a ligand may be covalently attached. Typically, the material to be used as an affinity matrix is insoluble in the system in which the target molecule is found. Usually, but not always, the insoluble matrix is solid. Hundreds of substances have been described and employed as affinity matrices. Useful affinity supports are those with a high surface area to volume ratio, chemical groups that are easily modified for covalent attachment of ligands, minimal nonspecific binding properties, good flow characteristics and mechanical and chemical stability. Preferred solid supports are agarose, sepharose and polystyrene beads.

Preferably, affinity purification is performed by using biotin, digoxygenin, glutathione or nickel-nitrilotriacetic acid (NTA) as the affinity tag of the compound of formula (I) of the present invention or a derivative thereof.

In another more preferred embodiment of the present invention, the compound of formula (I) of the present invention or a derivative thereof is added to a cytosine residue and cannot be added to a 5-methylcytosine residue in DNA.

In a preferred embodiment of the present invention, the method comprises after step (a) the additional step of sequencing the DNA molecule. Any methods known in the art may be used for sequencing. Preferably, the nucleic acid sequence is determined by a method based on the sequencing techniques of Sanger or Maxam/Gilbert (see for example: Methods in Molecular Biology, Vol. 167 (Graham and Hill, eds.): DNA sequencing protocols. $2^{nd}$ edition, 2001; Galas and McCormack, Genomic Technologies: Present and Future. Caister Academic Press, Wymondham, UK, 2002).

In another preferred embodiment of the present invention, the label of said detectable cofactor is detected by (a) an antibody specifically binding to the label of said detectable cofactor or by (b) avidin or streptavidin specifically binding to the label of said detectable cofactor.

The term "antibody", as used throughout the invention, refers to monoclonal antibodies, polyclonal antibodies, chimeric antibodies, single chain antibodies, or a fragment thereof. Preferably the antibody is specific for its epitope. The antibodies may be humanized antibodies, synthetic antibodies, antibody fragments, such as Fab, F(ab2)', Fv or scFv fragments etc., or a chemically modified derivative of any of these. Monoclonal antibodies can be prepared, for example, by the techniques as originally described in Köhler and Milstein, (1975) Nature 256, 495, and Galfré, (1981) Meth. Enzymol. 73, 3, which comprise the fusion of mouse myeloma cells to spleen cells derived from immunized mammals with modifications developed by the art. Furthermore, antibodies or fragments thereof can be obtained by using methods which are described, e.g. in Harlow and Lane "Antibodies, A Laboratory Manual", CSH Press, Cold Spring Harbor, 1998. When derivatives of said antibodies are obtained by the phage display technique, surface plasmon resonance as employed in the BIAcore system can be used to increase the efficiency of phage antibodies which bind to an epitope to be analyzed (Schier, (1996) Human Antibodies Hybridomas 7, 97-105; Malmborg, (1995) J. Immunol. Methods 183, 7-13). The production of chimeric antibodies is described, for example, in WO89/09622.

Antibodies may be labelled, wherein the label may be any of the labels mentioned in the present invention.

Finally, in another preferred embodiment of the present invention, the identity of said DNA molecule is determined by DNA sequencing, hybridization, Maldi-T of or analysis of nucleoside composition by enzymatic fragmentation and chromatography.

The invention is further illustrated by the following examples without being restricted to these examples.

EXAMPLE 1

Syntheses of Cofactor Analogs 3-9

The syntheses of cofactor analogs 3-9 were carried out as shown in Scheme 1.

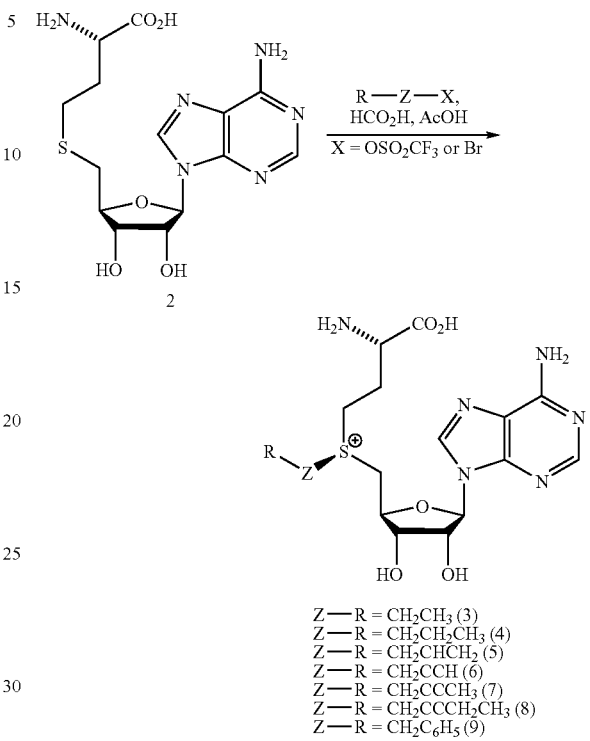

Scheme 4: Chemical syntheses of cofactor analogs 3-9, with cofactor analogs 5 to 9 being according to the present invention and cofactor analogs 3 and 4 being present for comparison only.

General Procedure for the Syntheses of Cofactor Analogs 3-9

To S-adenosyl-L-homocysteine (2, Sigma-Aldrich) in formic acid and acetic:acid (1:1 mixture) was slowly added an alkyl triflate or alkyl bromide at 0° C. The solution was allowed to warm up at room temperature and incubated at room temperature with shaking. The progress of the reaction leading to cofactors 3-6 and 9 was analyzed by analytical cation exchange HPLC (EC 250/4 Nucleosil 100-5 SA, equipped with a CC 8/4 Nucleosil 100-5 SA pre-column, Macherey-Nagel, Düren, Germany). Compounds were eluted isocratically with triethylammonium acetate buffer (100 mM, pH 4.0) containing sodium azide (1 mM) and a flow of 1 mL/min. Compounds were detected at 260 nm and 278 nm. The formation of cofactors 7 and 8 was analyzed by analytical reversed-phase HPLC (Discovery C18 150×2.1 mm, 5 µm, equipped with a Supelguard Discovery C18 20×2.1 mm, 5 µm pre-column, Supelco, Germany) coupled with a mass spectrometric detector (HP 1100 series ESI-MS equipped with a single quadruple). Compounds were eluted with methanol (0% for 6 min followed by linear gradients to 100% in 6 min and 100% in 4 min) in aqueous ammonium formate (20 mM, pH 3.5) and a flow of 0.3 mL/min. Post-column mobile phase modification (equal co-flow of 1% $CF_3COOH$ in methanol) was used to enhance the efficiency of MS detection. In addition, compounds were detected at 210 nm, 260 nm and 280 nm.

The reaction was quenched by adding water (30 mL for cofactors 3-6 and 9 or 20 mL for cofactors 7 and 8) and the aqueous phases were extracted with diethyl ether (3×5 mL for cofactors 3-6, 3×20 mL for cofactors 7, 8 and 3×15 mL for cofactor 9). The aqueous phase containing cofactors 3-6 and 9 was concentrated by lyophilisation and the resulting light brown oil was dissolved in water (5 mL) containing 0.01% trifluoroacetic acid. Purification and separation of the cofactor epimers at the sulfur centre (no separation of epimers was obtained for cofactor 9) were performed by preparative reversed-phase HPLC (Prontosil-ODS 5 μm, 120 Å, 250×20 mm, equipped with a Prontosil-ODS 5 μm, 120 Å, 30×20 mm pre-column, Bischoff, Leonberg, Germany). Compounds were eluted with acetonitrile (cofactors 3-6: linear gradients to 10% in 15 min and to 70% in 5 min, cofactor 9: linear gradients from 14% to 42% in 10 min and to 70% in 5 min) in aqueous trifluoroacetic acid (0.01%) and a flow of 10 mL/min. Compounds were detected at 260 nm and 278 nm or 285 nm. Purification of cofactors 7 and 8 was performed by preparative reversed-phase HPLC (Discovery C18 250×10 mm, 5 μm, equipped with a Supelguard Discovery C18 20×10 mm, 5 μm pre-column, Supelco, Germany). Compounds were eluted with methanol (linear gradient to 100% in 12 min) in aqueous ammonium formate (20 mM, pH 3.5) and a flow of 4.5 mL/min at 20° C. Compounds were detected at 210 nm, 260 nm and 280 nm. Product containing fractions were collected and solvents removed by lyophilisation. The yield was determined by UV spectroscopy using an extinction coefficient of 15400 L mol$^{-1}$ cm$^{-1}$ at 260 nm for the adenine chromophore in the cofactor.

A. 5'-[(S)-[(3S)-3-Amino-3-carboxypropyl]ethylsulfonio]-5'-deoxy-adenosine (S-adenosyl-L-ethionine), Cofactor 3 (Comparison)

S-Adenosyl-L-homocysteine (2) (20 mg, 52 μmol) was dissolved in a 1:1 mixture of formic acid and acetic acid (3 mL) and ethyltrifluoromethyl sulfonate (1.21 mL, 9.36 mmol, Sigma-Aldrich) was added. The reaction was performed and worked up after 2 h as described under general procedure. Purification by preparative reversed-phase HPLC yielded 3 (retention time 7.5 min, 10.9 μmol, 21%) and its epimer (retention time 7.8 min, 6.0 μmol, 12%) as white solids.

ESI-MS m/z (relative intensity): 413.2 (2) [M]$^+$, 334.2 (5) [5'-ethylthio-5'-deoxyadenosine+Na]$^+$, 250.1 (88) [M−ethionine]$^+$, 136.2 (100) [adenine+H]$^+$.

B. 5'-[(S)-[(3S)-3-Amino-3-carboxypropyl]propylsulfonio]-5'-deoxy-adenosine (S-adenosyl-L-propionine), Cofactor 4 (Comparison)

S-Adenosyl-L-homocysteine (2) (20 mg, 52 μmol) was dissolved in a 1:1 mixture of formic acid and acetic acid (3 mL) and propyltrifluoromethyl sulfonate (1.8 g, 9.36 mmol, prepared according to a method by Ross et al., (2000) J. Chem. Soc., Perkin Trans. 1, 571-574) was added. The reaction was performed and worked up after 2.5 h as described under general procedure. Purification by preparative reversed-phase HPLC yielded 4 (retention time 16.6 min, 10.5 μmol, 20%) and its epimer (retention time 16.9 min, 8.3 μmol, 16%) as white solids.

ESI-MS m/z (relative intensity): 348.0 (17) [5'-propylthio-5'-deoxyadenosine+Na]$^+$, 326.0 (100) [5'-propylthio-5'-deoxyadenosine+H]$^+$.

C. 5'-[(S)-[(3S)-3-Amino-3-carboxypropyl]prop-2-enylsulfonio]-5'-deoxyadenosine, Cofactor 5

S-Adenosyl-L-homocysteine (2) (20 mg, 52 μmol) was dissolved in a 1:1 mixture of formic acid and acetic acid (3 mL) and allyl bromide (264 μL, 3.12 mmol, Sigma-Aldrich) was added. The reaction was performed and worked up after 4 d as described under general procedure. Purification by preparative reversed-phase HPLC yielded 5 (retention time 17.1 min, 7.2 μmol, 14%) and its epimer (retention time 17.9 min, 11.6 μmol, 22%) as white solids.

ESI-MS m/z (relative intensity): 346.0 (30) [5'-(prop-2-enyl)thio-5'-deoxyadenosine+Na]$^+$, 324.0 (100) [5'-(prop-2-enyl)thio-5'-deoxyadenosine+H]$^+$.

D. 5'-[(S)-[(3S)-3-Amino-3-carboxypropyl]prop-2-ynylsulfonio]-5'-deoxy-adenosine, Cofactor 6

S-Adenosyl-L-homocysteine (2) (20 mg, 52 μmol) was dissolved in a 1:1 mixture of formic acid and acetic acid (3 mL) and propargyltrifluoromethyl sulfonate (1.76 g, 9.36 mmol, prepared according to a method by Ross et al., (2000) J. Chem. Soc., Perkin Trans. 1, 571-574). The reaction was performed and worked up after 30 min as described under general procedure. Purification by preparative reversed-phase HPLC yielded 6 (retention time 8.8 min, 10.8 μmol, 21%) and its epimer (retention time 9.5 min, 7.7 μmol, 15%) as white solids.

ESI-MS m/z (relative intensity): 344.0 (26) [5'-(prop-2-ynyl)thio-5'-deoxyadenosine+Na]$^+$, 322.0 (100) [5'-(prop-2-ynyl)thio-5'-deoxyadenosine+H]$^+$, 136.0 (8) [adenine+H]$^+$.

E. 5'-[(S)-[(3S)-3-Amino-3-carboxypropyl]but-2-ynylsulfonio]-5'-deoxyadenosine, Cofactor 7

S-Adenosyl-L-homocysteine (2) (20 mg, 52 μmol) was dissolved in a 1:1 mixture of formic acid and acetic acid (1 mL) and but-2-ynyltrifluoromethyl sulfonate (200 equivalents) was added. The reaction was performed and worked up after 2 h as described under general procedure. The product eluting with a retention time of 13.4 min during analytical reversed-phase HPLC was purified by preparative reversed-phase HPLC. Cofactor 7 (2.6 μmol, 5%) was obtained as a mixture of epimers at the sulfur centre.

ESI-MS m/z (relative intensity): 437.1 (100) [M]$^+$, 336.1 (2) [5'-(but-2-ynyl)thio-5'-deoxyadenosine+H]$^+$, 250.1 (88) [5'-deoxyadenosine]$^+$.

F. 5'-[(S)-[(3S)-3-Amino-3-carboxypropyl]pent-2-ynylsulfonio]-5'-deoxyadenosine, Cofactor 8

S-Adenosyl-L-homocysteine (2) (10 mg, 26 μmol) was dissolved in a 1:1 mixture of formic acid and acetic acid (0.5 mL) and pent-2-ynyltrifluoromethyl sulfonate (200 equivalents) was added. The reaction was performed and worked up after 2 h as described under general procedure. The product and its epimer eluting with a retention time of 16.0 min and 15.8 min, respectively, during analytical reversed-phase HPLC were purified by preparative reversed-phase HPLC. Cofactor 8 (1.8 μmol, 7.0%) and its epimer (2.0 μmol, 7.7%) were obtained as white solids.

ESI-MS m/z (relative intensity): 451.1 (100) [M]$^+$, 350.1 (10) [5'-(pent-2-ynyl)thio-5'-deoxyadenosine)+H]$^+$, 250.1 (20) [5'-deoxyadenosine]$^+$.

G. 5'-[(S)-[(3S)-3-Amino-3-carboxypropyl]benzylsulfonio]-5'-deoxyadenosine, Cofactor 9

S-Adenosyl-L-homocysteine (2) (20 mg, 52 μmol) was dissolved in a 1:1 mixture of formic acid and acetic acid (1 mL) and benzyl bromide (1.1 mL, 9.4 mmol). The reaction was performed and worked up after 5 h as described under general procedure. Purification by preparative reversed-phase HPLC yielded 9 as a mixture of epimers at the sulfur centre (retention time 9.0 min, 24.7 μmol, 47.5%) as a white solid.

ESI-MS m/z (relative intensity): 475.2 (100) [M]$^+$. ESI-MS-MS (475.2) m/z (relative intensity): 374.0 (88.5) [5'-benzylthio-5'-deoxyadenosine+H]$^+$, 340.0 (59.5) [M−adenine]$^+$, 250.2 (86.1) [5'-deoxyadenosine]$^+$, 226.2 (100) [S-benzyl-homocysteine+H]$^+$.

Example 2

Sequence-Specific Modifications of Short Duplex Oligodeoxynucleotides with Cofactors 3-9 and DNA Methyltransferases from Different Classes Transfer of the activated ethyl ($CH_2CH_3$), propyl ($CH_2CH_2CH_3$), prop-2-enyl ($CH_2CHCH_2$), prop-2-ynyl group ($CH_2CCH$), but-2-ynyl ($CH_2CCCH_3$), pent-2-ynyl ($CH_2CCCH_2CH_3$) or benzyl group ($CH_2C_6H_5$) from cofactors 3-9 by the DNA adenine-N6 methyltransferase M.TaqI, the DNA cytosine-C5 methyltransferase M.HhaI variant Q82A or the DNA cytosine-N4 methyltransferase M.BcnIB to DNA was first investigated using short duplex oligodeoxynucleotides as substrates. After enzymatic transfer the duplex oligodeoxynucleotides were enzymatically fragmented and the resulting modified nucleosides were analyzed by reversed-phase HPLC coupled with ESI-MS.

A. Modifications of Adenine-N6 within a Duplex Oligodeoxynucleotide by M.TaqI

The hemimethylated duplex oligodeoxynucleotide I-II was produced by mixing equal molar amounts (15 nmol) of complementary single-stranded oligodeoxynucleotide I (5'-GCCGCTCGATGCCG-3') (SEQ ID NO. 1) and II (5'-CGGCATCGA$^{Me}$GCGGC-3', A$^{Me}$=N6-methyl-2'-deoxyadenosine) (SEQ ID NO. 2) in buffer (150 µL, 20 mM Tris-acetate, 50 mM potassium acetate, 10 mM magnesium acetate, 1 mM dithiothreitol, 0.01% Triton X-100, pH 7.9), heating at 95° C. for 5 min and slow cooling to room temperature. Enzymatic modifications (Scheme 5) were performed by incubation of duplex oligodeoxynucleotide I.II (20 µM) with cofactors 3-9 (3-6 400 µM, 7-8 200 µM and 9 300 µM) and M.TaqI (22 µM, produced as described in Goedecke et al., (2001) Nature Struct. Biol. 8, 121-125) in buffer (20 mM Tris-acetate, 50 mM potassium acetate, 10 mM magnesium acetate, 1 mM dithiothreitol, 0.01% Triton X-100, pH 7.9) at 37° C. over night. M.TaqI was denatured by heating to 95° C. for 10 min and removed by centrifugation (13200 rpm/min, 2 min). The modified duplex oligodeoxynucleotides I$^{Z—R}$-II were desalted by gel filtration (NAP-5 column, Amersham Biosciences, Freiburg, Germany), eluted with water (1 mL) and lyophilized.

The modified duplex oligodeoxynucleotides I$^{Z—R}$-II were dissolved in buffer (100 µL, 10 mM Tris hydrochloride, 10 mM magnesium chloride, 1 mM zinc acetate, pH 7.5) containing Nuclease PI (1500 u, Sigma, Taufkirchen, Germany) and calf intestine alkaline phosphatase (30 u, MBI Fermentas, St. Leon-Rot, Germany) and incubated at 37° C. for 4 h. Nucleosides were analyzed by reversed-phase HPLC (Symmetry-$C_{18}$ 5 µm, 100 Å, 250×4.6 mm, equipped with a Symmetry-$C_{18}$ 5 µm, 100 Å, 20×4.6 mm pre-column, Waters, Eschborn, Germany). Compounds were eluted with acetonitrile (5% for 7 min, followed by linear gradients to 6% in 15 min, to 35% in 8 min and to 70% in 2 min) in triethylammonium acetate buffer (10 mM, pH 7.0) at a flow of 1 mL/min and detected at 254 nm.

For HPLC-coupled ESI-MS measurements compounds were eluted with methanol (0% for 3 min, followed by a linear gradient to 100% in 22 min) in ammonium formate buffer (20 mM, pH 3.5). A post-column mobile phase modification (equal co-flow of 96% methanol, 4% formic acid) was used to Scheme 5: Sequence-specific modifications of the hemimethylated duplex oligodeoxynucleotide I-II by the DNA adenine-N6 methyltransferase M.TaqI. Note that the 5'-TCGA-3' DNA recognition sequence of M. TaqI (in bold) contains only one modifiable target adenine which is located in the upper strand I. The other target adenine in the lower strand II is blocked by methylation (A$^{Me}$ = N6-methyl-2'-deoxyadenosine). Thus, modification of the recognition sequence can only occur in the upper strand I.

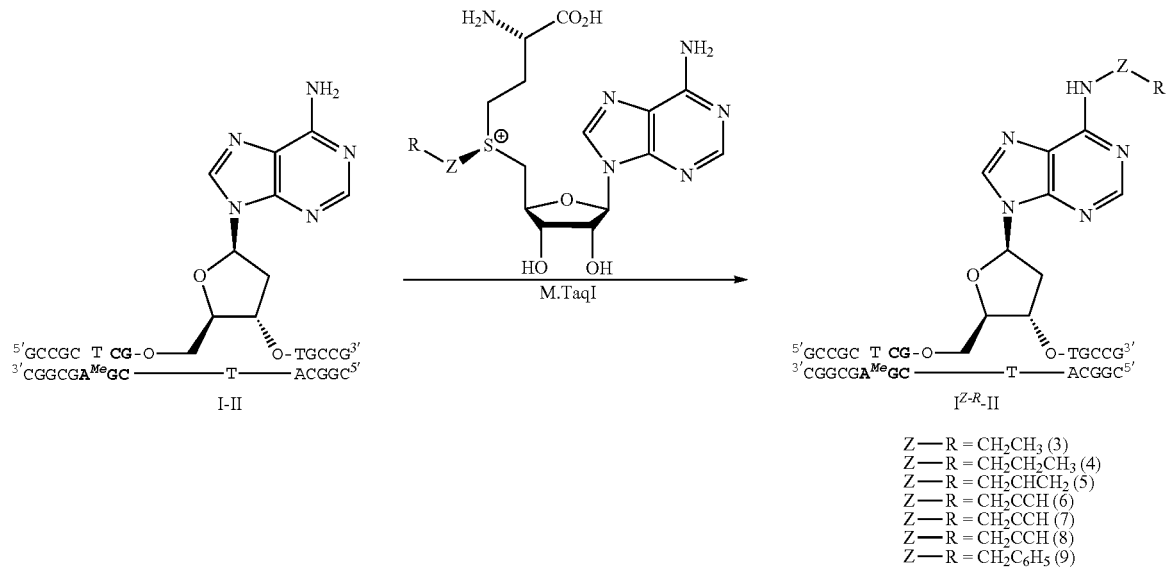

Z—R = $CH_2CH_3$ (3)
Z—R = $CH_2CH_2CH_3$ (4)
Z—R = $CH_2CHCH_2$ (5)
Z—R = $CH_2CCH$ (6)
Z—R = $CH_2CCH$ (7)
Z—R = $CH_2CCH$ (8)
Z—R = $CH_2C_6H_5$ (9)

enhance the detection efficiency of 2'-deoxyadenosine and its derivatives. Mass spectra were recorded in 200-370 m/z range.

A.1 Duplex Oligodeoxynucleotide Analysis after Treatment with Cofactor 3 (—Z—R=—$CH_2CH_3$) and M.TaqI (Comparison)

Fragmentation of the modified duplex oligodeoxynucleotide $I^{Z-R}$-II with —Z—R=—$CH_2CH_3$ (trace a in FIG. 1) revealed in addition to the natural nucleosides dC, dG, dT, dA and $dA^{Me}$ a new compound with a longer retention time (30.5 min) than $dA^{Me}$. This new compound was analyzed by coupled ESI-MS and the observed mass (m/z: 280.1 [M]$^+$) is in agreement with N6-ethyl-2'-deoxyadenosine ($dA^{Ethyl}$). The experimentally determined nucleotide composition of the modified duplex oligodeoxynucleotide was found to be in good agreement with the theoretical nucleotide composition (given in brackets): dC 11.4 (11), dG 10.6 (11), dT 3.0 (3), dA 0.9 (1), $dA^{Me}$ 1.0 (1) and $dA^{Ethyl}$ 1.0 (1). Thus, the AdoMet analog 3 functions as a cofactor for M.TaqI.

A.2 Duplex Oligodeoxynucleotide Analysis after Treatment with Cofactor 4 (—Z—R=—$CH_2CH_2CH_3$) and M.TaqI (Comparison)

Fragmentation of the modified duplex oligodeoxynucleotide $I^{Z-R}$.II with —Z—R=—$CH_2CH_2CH_3$ (trace b in FIG. 1) revealed in addition to the natural nucleosides dC, dG, dT, dA and $dA^{Me}$ a new compound with a longer retention time (32.0 min) than $dA^{Me}$. This new compound was analyzed by coupled ESI-MS and the observed mass (m/z: 294.2 [M]$^+$) is in agreement with N6-propyl-2'-deoxyadenosine ($dA^{Propyl}$). The experimentally determined nucleotide composition of the modified duplex oligodeoxynucleotide was found to be in good agreement with the theoretical nucleotide composition (given in brackets): dC 11.4 (11), dG 10.7 (11), dT 2.9 (3), dA 1.0 (1), $dA^{Me}$ 1.0 (1) and $dA^{Propyl}$ 1.0 (1). Thus, the AdoMet analog 4 functions as a cofactor for M.TaqI.

A.3 Duplex Oligodeoxynucleotide Analysis after Treatment with Cofactor 5 (—Z—R=—$CH_2CH=CH_2$) and M.TaqI Fragmentation of the modified duplex oligodeoxynucleotide $I^{Z-R}$.II with —Z—R=—$CH_2CH=CH_2$ (trace c in FIG. 1) revealed in addition to the natural nucleosides dC, dG, dT, dA and $dA^{Me}$ a new compound with a longer retention time (31.5 min) than $dA^{Me}$. This new compound was analyzed by coupled ESI-MS and the observed mass (m/z: 292.2 [M]$^+$) is in agreement with N6-propenyl-2'-deoxyadenosine ($dA^{Propenyl}$). The experimentally determined nucleotide composition of the modified duplex oligodeoxynucleotide was found to be in good agreement with the theoretical nucleotide composition (given in brackets): dC 11.4 (11), dG 10.7 (11), dT 3.0 (3), dA 0.9 (1), $dA^{Me}$ 1.0 (1) and $dA^{Propenyl}$ 1.1 (1). Thus, the AdoMet analog 5 functions as a cofactor for M.TaqI.

A.4 Duplex Oligodeoxynucleotide Analysis after Treatment with Cofactor 6 (—Z—R=—$CH_2C\equiv CH$) and M.TaqI Fragmentation of the modified duplex oligodeoxynucleotide $I^{Z-R}$.II with —Z—R=—$CH_2C\equiv CH$ (trace d in FIG. 1) revealed in addition to the natural nucleosides dC, dG, dT, dA and $dA^{Me}$ a new compound with a longer retention time (30.5 min) than $dA^{Me}$. This new compound was analyzed by coupled ESI-MS and the observed mass (m/z: 290.2 [M]$^+$) is in agreement with N6-propynyl-2'-deoxyadenosine ($dA^{Propynyl}$). The experimentally determined nucleotide composition of the modified duplex oligodeoxynucleotide was found to be in good agreement with theoretical nucleotide composition (given in brackets): dC 11.4 (11), dG 11.1 (11), dT 2.7 (3), dA 0.9 (1), $dA^{Me}$ 1.0 (1) and $dA^{Propynyl}$ 0.9 (1). Thus, the AdoMet analog 6 functions as a cofactor for M.TaqI.

A.5 Duplex Oligodeoxynucleotide Analysis after Treatment with Cofactor 7 (—Z—R=—$CH_2C\equiv CCH_3$) and M.TaqI Fragmentation of the modified duplex oligodeoxynucleotide $I^{Z-R}$.II with —Z—R=—$CH_2C\equiv CCH_3$ (trace e in FIG. 1) revealed in addition to the natural nucleosides dC, dG, dT, dA and $dA^{Me}$ a new compound with a longer retention time (31.9 min) than $dA^{Me}$. This new compound was analyzed by coupled ESI-MS and the observed mass (m/z: 304.2 [M]$^+$) is in agreement with N6-but-2-ynyl-2'-deoxyadenosine ($dA^{But-2-ynyl}$). The experimentally determined nucleotide composition of the modified duplex oligodeoxynucleotide was found to be in good agreement with theoretical nucleotide composition (given in brackets): dC 11.2 (11), dG 10.9 (11), dT 2.8 (3), dA 0.9 (1), $dA^{Me}$ 1.0 (1) and $dA^{But-2-ynyl}$ 1.0 (1). Thus, the AdoMet analog 7 functions as a cofactor for M.TaqI.

A.6 Duplex Oligodeoxynucleotide Analysis after Treatment with Cofactor 8 (—Z—R=—$CH_2C\equiv CCH_2CH_3$) and M.TaqI Fragmentation of the modified duplex oligodeoxynucleotide $I^{Z-R}$.II with —Z—R=—$CH_2C\equiv CCH_2CH_3$ (trace f in FIG. 1) revealed in addition to the natural nucleosides dC, dG, dT, dA and $dA^{Me}$ a new compound with a longer retention time (33.5 min) than $dA^{Me}$. This new compound was analyzed by coupled ESI-MS and the observed mass (m/z: 318.2 [M]$^+$) is in agreement with N6-pent-2-ynyl-2'-deoxyadenosine ($dA^{Pent-2-ynyl}$). The experimentally determined nucleotide composition of the modified duplex oligodeoxynucleotide was found to be in good agreement with theoretical nucleotide composition (given in brackets): dC 11.2 (11), dG 10.9 (11), dT 2.8 (3), dA 0.9 (1), $dA^{Me}$ 1.0 (1) and $dA^{Pent-2-ynyl}$ 1.0 (1). Thus, the AdoMet analog 8 functions as a cofactor for M.TaqI.

A.7 Duplex Oligodeoxynucleotide Analysis after Treatment with Cofactor 9 (—Z—R=—$CH_2C_6H_5$) and M.TaqI Fragmentation of the modified duplex oligodeoxynucleotide $I^{Z-R}$.II with —Z—R=—$CH_2C_6H_5$ (trace g in FIG. 1) revealed in addition to the natural nucleosides dC, dG, dT, dA and $dA^{Me}$ a new compound with a longer retention time (34.3 min) than $dA^{Me}$. This new compound was isolated and analyzed by ESI-MS and the observed mass (m/z: 341 [M]$^+$) is in agreement with N6-benzyl-2'-deoxyadenosine ($dA^{Benzyl}$). The experimentally determined nucleotide composition of the modified duplex oligodeoxynucleotide was found to be in good agreement with theoretical nucleotide composition (given in brackets): dC 11.3 (11), dG 11.0 (11), dT 3.0 (3), dA 0.8 (1), $dA^{Me}$ 1.0 (1) and $dA^{Benzyl}$ 0.9 (1). Thus, the AdoMet analog 9 functions as a cofactor for M.TaqI.

B. Modifications of Cytosine-C5 within a Duplex Oligodeoxynucleotide by the M.HhaI Variant Q82A Scheme 6: Sequence-specific modifications of the duplex oligodeoxynucleotide III-IV by the DNA cytosine-C5 methyltransferase M.HhaI-Q82A. Note that the double-stranded 5'-GCGC-3' DNA recognition sequence (in bold) contains two modifiable target cytosines and modification of the second cytosine residue within the recognition sequence can either occur in the upper strand III (shown) or in the lower strand IV (not shown).

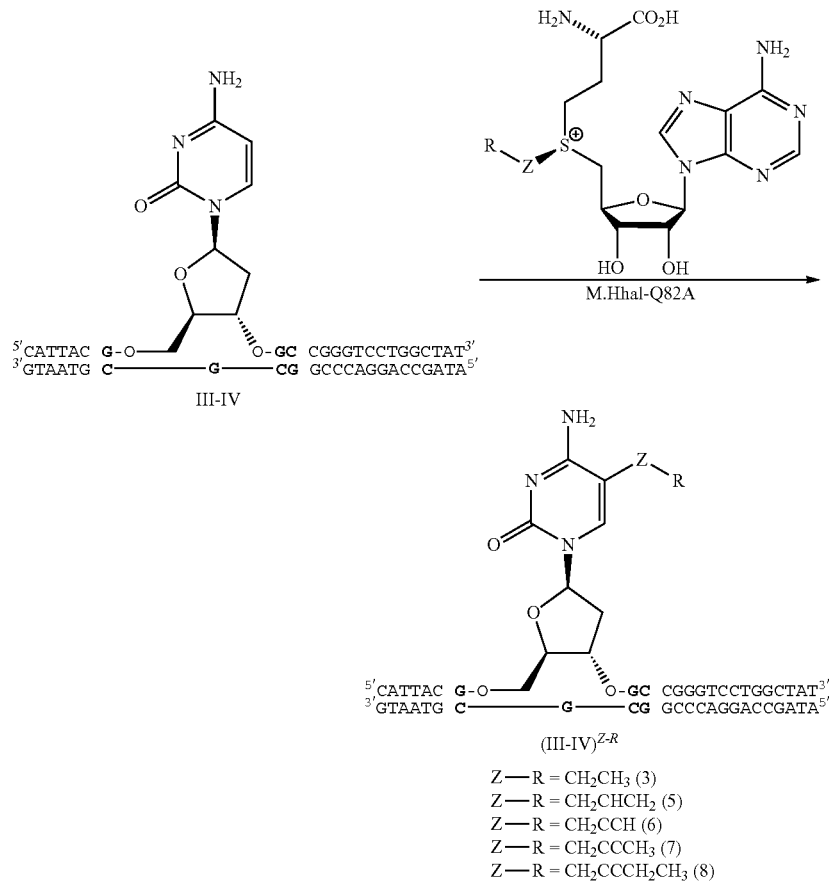

to room temperature. Enzymatic modifications (Scheme 6) were investigated by incubation of duplex oligodeoxynucleotide III.IV (12.5 µM) with cofactors 3-8 (300 µM) and M.HhaI-Q82A (15 µM) in buffer (50 mM Tris hydrochloride, 10 mM sodium chloride, 0.5 mM ethylenediaminetetraacetic acid, 2 mM 2-mercaptoethanol, 0.2 mg/mL bovine serum albumin, pH 7.4 for cofactors 3-5, 7 and 8; 25 mM 3-morpholino-propanesulfonic acid, 25 mM 2-morpholino-ethanesulfonic acid, 10 mM sodium chloride, 0.5 mM ethylenediaminetetraacetic acid, 2 mM 2-mercaptoethanol, 0.2 mg/mL bovine serum albumin, pH 6.0 for cofactor 6 at 37° C. over night. M.HhaI-Q82A was denatured by heating to 80° C. for 10 min and incubation with Proteinase K at 55° C. for 1 h. Hydrolysis products were removed by gel filtration (G-25 column, Amersham Biosciences).

The three-dimensional structure of M.HhaI in complex with DNA and the natural cofactor AdoMet 1 (PDB id: 6 MHT; Kumar et al., (1997) Nucleic Acids Res. 25, 2773-2783) suggested that Q82 could lead to unfavorable steric interactions with cofactor analogs containing extended methyl group replacements. Therefore, the codon for Q82 was changed to a codon for alanine by standard Kunkel mutagenesis (Kunkel et al., (1989) Proc. Natl. Acad. Sci. USA 82, 488-492) and the correct DNA sequence of the complete gene was verified by DNA sequencing. Expression and purification of the Q82A variant was performed as described for the wild-type enzyme (Kumar et al., (1992) Biochemistry 31, 8648-8653; Klimasauskas et al., (1998) EMBO J. 17, 317-324). The presence of the amino acid substitution was verified by mass spectrometric analysis of purified M.HhaI-Q82A.

The duplex oligodeoxynucleotide III.IV was produced by mixing equal molar amounts (2.5 nmol) of complementary single-stranded oligodeoxynucleotide III (5'-CAT-TACGCGCCGGGTCCTGGCTAT-3') (SEQ ID NO. 3) and IV (5'-ATAGCCAGGACCCGGCGCGTAATG-3') (SEQ ID NO. 4) in water, heating at 85° C. for 5 min and slow cooling The obtained solutions of duplex oligodeoxynucleotides were treated with buffer (1/10 volume, 100 mM Tris hydrochloride, 100 mM magnesium chloride, 10 mM zinc acetate, pH 7.5) containing Nuclease P1 (1500 u, Sigma) and calf intestine alkaline phosphatase (30 u, MBI Fermentas) and incubated at 37° C. for 4 h. Nucleosides were analyzed by reversed-phase HPLC (Discovery C18 150×2.1 mm, 5 µm, equipped with a Supelguard Discovery C18 20×2.1 mm, 5 µm, pre-column, Supelco, Germany) coupled with a mass spectrometric detector (HP 1100 series ESI-MS equipped with single quadruple). Compounds were eluted with methanol (0% for 6 min, followed by linear gradients to 56% in 15 min and to 80% in 1 min) in ammonium formate buffer (20 mM, pH 4.25 for cofactors 3, 4, 6 and pH 3.5 for cofactors 5, 7, 8) at a flow of 0.3 mL/min and detected at 280 nm. For on-line mass spectrometric detection post-column mobile phase modification (equal co-flow of 96% methanol, 4% formic acid and 1 mM sodium hydroxide) was used to enhance the detection efficiency of 2'-deoxycytidine and its derivatives. Mass spectra were recorded in 50-600 m/z range.

B.1 Duplex Oligodeoxynucleotide Analysis after Treatment with Cofactor 3 (—Z—R=—CH$_2$CH$_3$) and M.HhaI-Q82A (Comparison)

Figure 2A:
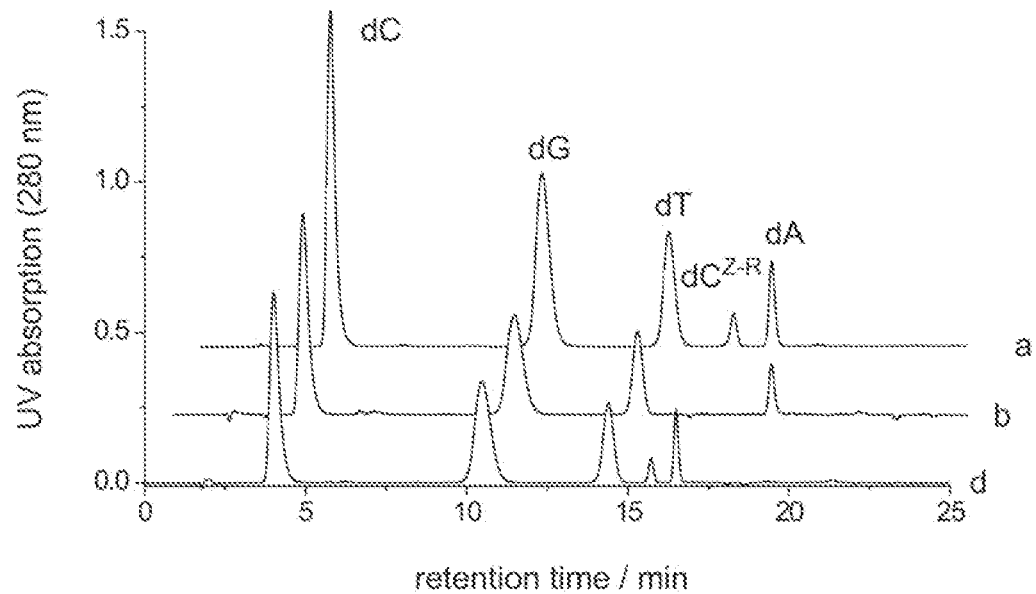
FIG. 2 shows an HPLC analysis of enzymatically fragmented duplex oligodeoxynucleotides (III-IV)$^{Z-R}$ obtained after treatment with cofactors 3-8 and M.HhaI-Q82A. In $dC^{Z-R}$ the chemical group Z—R is attached to the C5 position of dC. Curve (a): cofactor 3 with Z=$CH_2$, and R=—$CH_3$; curve (b): cofactor 4 with Z=$CH_2$ and R=—$CH_2CH_3$; curve (c): cofactor 5 with Z=$CH_2$ and R=—CH=$CH_2$; curve (d): cofactor 6 with Z=$CH_2$ and R=—C≡CH; curve (e): cofactor 7 with Z=$CH_2$ and R=—C≡$CCH_3$ and curve (f): cofactor 8 with Z=$CH_2$ and R=—C≡C—$CH_2CH_3$.
Figure 2B:
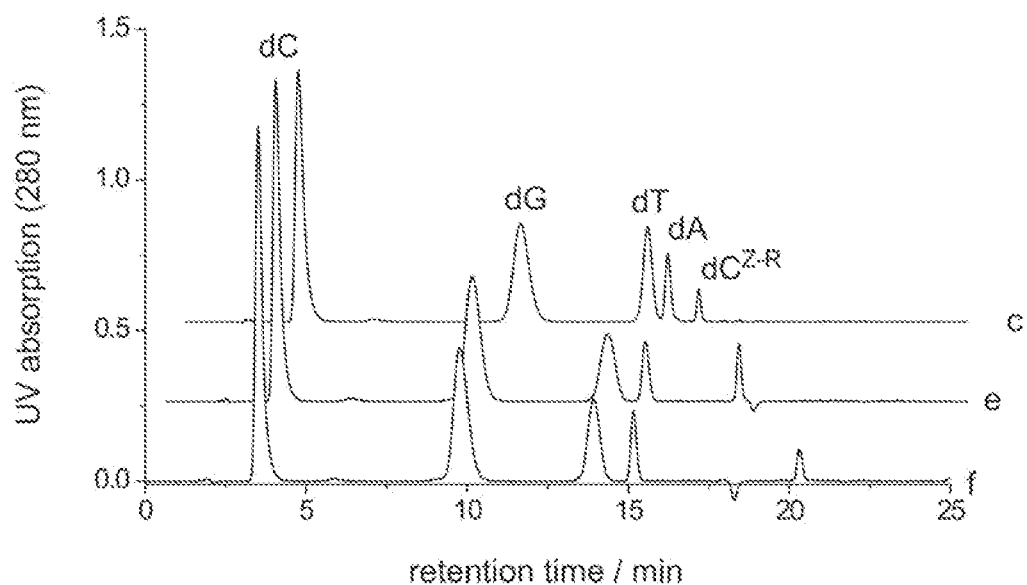

Fragmentation of the modified duplex oligodeoxynucleotide (III.IV)Z—R with —Z—R=—CH$_2$CH$_3$ (trace a in FIG. 2) revealed in addition to the natural nucleosides dC, dG, dT and dA a new compound with a retention time of 16.5 min. This new compound was analyzed by coupled ESI-MS and the observed mass (m/z: 278 [M+Na]$^+$, 162 [C5-ethyl-cytosine+Na]$^+$) is in agreement with C5-ethyl-2'-deoxycytidine (dC$^{C5-Ethyl}$). Thus, the AdoMet analog 3 functions as a cofactor for M.HhaI-Q82A.

B.2 Duplex Oligodeoxynucleotide Analysis after Treatment with Cofactor 4 (—Z—R=—CH$_2$CH$_2$CH$_3$) and M.HhaI-Q82A (Comparison)

Fragmentation of the duplex oligodeoxynucleotide (trace b in FIG. 2) revealed only the natural nucleosides dC, dG, dT and dA. Thus, the AdoMet analog 4 does not function as a cofactor for M.HhaI-Q82A.

B.3 Duplex Oligodeoxynucleotide Analysis after Treatment with Cofactor 5 (—Z—R=—CH$_2$CH=CH$_2$) and M.HhaI-Q82A Fragmentation of the modified duplex oligodeoxynucleotide (III.IV)$^{Z—R}$ with —Z—R=—CH$_2$CH=CH$_2$ (trace c in FIG. 2) revealed in addition to the natural nucleosides dC, dG, dT and dA a new compound with a retention time of 15.9 min. This new compound was analyzed by coupled ESI-MS and the observed mass (m/z: 290 [M+Na]$^+$, 174 [C5-propenyl-cytosine+Na]$^+$) is in agreement with C5-propenyl-2'-deoxycytidine (dC$^{C5-Propenyl}$). Thus, the AdoMet analog 5 functions as a cofactor for M.HhaI-Q82A.

B.4 Duplex Oligodeoxynucleotide Analysis after Treatment with Cofactor 6 (—Z—R=—CH$_2$C≡CH) and M.HhaI-Q82A Fragmentation of the modified duplex oligodeoxynucleotide (III.IV)$^{Z—R}$ with —Z—R=—CH$_2$C≡CH (trace d in FIG. 2) revealed in addition to the natural nucleosides dC, dG, dT and dA a new compound with a retention time of 15.7 min. This new compound was analyzed by coupled ESI-MS and the observed mass (m/z: 288 [M+Na]$^+$, 172 [C5-propynyl-cytosine+Na]$^+$) is in agreement with C5-propynyl-2'-deoxycytidine (dC$^{C5-Propynyl}$). Thus, the AdoMet analog 6 functions as a cofactor for M.HhaI-Q82A.

B.5 Duplex Oligodeoxynucleotide Analysis after Treatment with Cofactor 7 (—Z—R=—CH$_2$C≡CCH$_3$) and M.HhaI-Q82A Fragmentation of the modified duplex oligodeoxynucleotide (III.IV)$^{Z—R}$ with —Z—R=—CH$_2$C≡CCH$_3$ (trace e in FIG. 2) revealed in addition to the natural nucleosides dC, dG, dT and dA a new compound with a retention time of 17.8 min. This new compound was analyzed by coupled ESI-MS and the observed mass (m/z: 302 [M+Na]$^+$, 186 [C5-but-2-ynyl-cytosine+Na]$^+$) is in agreement with C5-but-2-ynyl-2'-deoxycytidine (dC$^{C5-But-2-ynyl}$). Thus, the AdoMet analog 7 functions as a cofactor for M.HhaI-Q82A.

B.6 Duplex Oligodeoxynucleotide Analysis after Treatment with Cofactor 8 (—Z—R=—CH$_2$C≡CCH$_2$CH$_3$) and M.HhaI-Q82A Fragmentation of the modified duplex oligodeoxynucleotide (III.IV)$^{Z—R}$ with —Z—R=—CH$_2$C≡CCH$_2$CH$_3$ (trace f in FIG. 2) revealed in addition to the natural nucleosides dC, dG, dT and dA a new compound with a retention time of 20.3 min. This new compound was analyzed by coupled ESI-MS and the observed mass (m/z: 316 [M+Na]$^+$, 200 [C5-pent-2-ynyl-cytosine+Na]$^+$) is in agreement with C5-pent-2-ynyl-2'-deoxycytidine (dC$^{C5-Pent-2-ynyl}$). Thus, the Ado Met analog 8 functions as a cofactor for M.HhaI-Q82A.

C. Modifications of Cytosine-N4 within a Duplex Oligodeoxynucleotide by M.BcnIB

Scheme 7: Sequence-specific modifications of the duplex oligodeoxynucleotide V-VI by the DNA cytosine-N4 methyltransferase M.BcnIB. Note that the double-stranded 5'CCGGG-3' DNA recognition sequence (in bold) within the duplex contains two modifiable target cytosines and modification of the second cytosine residue within the recognition sequence can either occur in the upper strand V (shown) or in the lower strand VI (not shown).

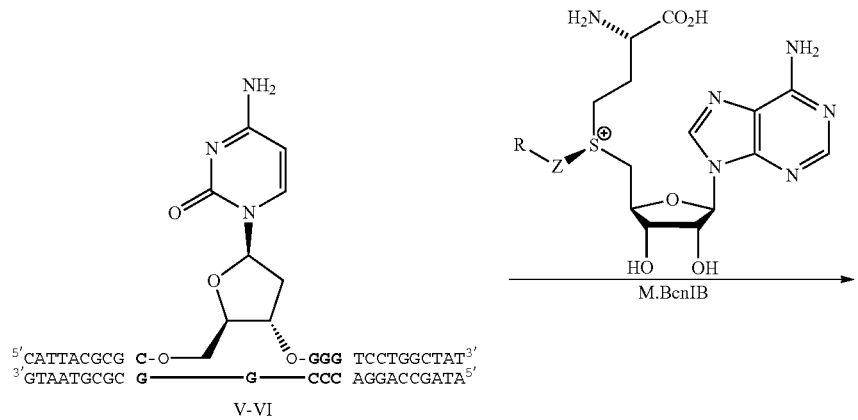

-continued

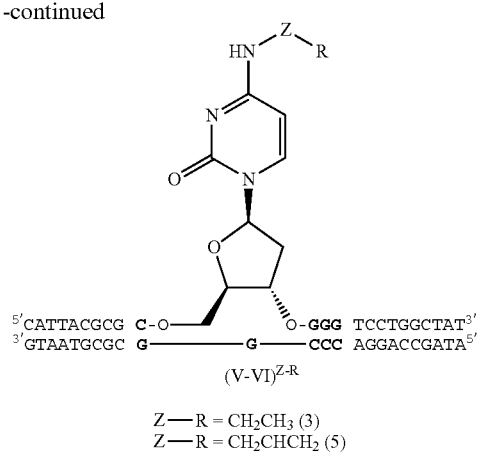

5'CATTACGCG C-O— —O-GGG TCCTGGCTAT3'
3'GTAATGCGC G——————G————CCC AGGACCGATA5'

(V·VI)$^{Z\text{-}R}$

Z—R = CH$_2$CH$_3$ (3)
Z—R = CH$_2$CHCH$_2$ (5)

The duplex oligodeoxynucleotide V.VI was produced by mixing equal molar amounts (2.5 nmol) of complementary single-stranded oligodeoxynucleotide V (5'-CATTACGCGCCGGGTCCTGGCTAT-3') (SEQ ID NO. 3) and VI (5'-ATAGCCAGGACCCGGCGCGTAATG-3') (SEQ ID NO. 4) in water, heating at 85° C. for 5 min and slow cooling to room temperature. Enzymatic modifications (Scheme 7) were investigated by incubation of duplex oligodeoxynucleotide V.VI (12.5 μM) with cofactors 3-6 (300 μM) and M.BcnIB (15 μM) in buffer (50 mM Tris hydrochloride, 10 mM sodium chloride, 0.5 mM ethylenediaminetetraacetic acid, 2 mM 2-mercaptoethanol, 0.2 mg/mL bovine serum albumin, pH 7.4 for cofactors 3-5; 25 mM 3-morpholino-propanesulfonic acid, 25 mM 2-morpholino-ethanesulfonic acid, 10 mM sodium chloride, 0.5 mM ethylenediaminetetraacetic acid, 2 mM 2-mercaptoethanol, 0.2 mg/mL bovine serum albumin, pH 6.0 for cofactor 6) at 37° C. over night. M.BcnIB was denatured by heating to 80° C. for 10 min and incubated with proteinase K at 55° C. 1 h. Hydrolysis products were removed using gel filtration column (G-25 column, Amersham Biosciences).

The obtained solutions of duplex oligodeoxynucleotides were treated with buffer (1/10 volume, 100 mM Tris-HCl, 100 mM magnesium chloride, 10 mM zinc acetate, pH 7.5) containing Nuclease P1 (1500 u, Sigma) and calf intestine alkaline phosphatase (30 u, MBI Fermentas) and incubated at 37° C. for 4 h. Nucleosides were analyzed by reversed-phase HPLC (Discovery C18 150×2.1 mm, 5 μm, equipped with a Supelguard Discovery C18 20×2.1 mm, 5 μm, pre-column, Supelco, Germany) coupled with a mass spectrometric detector (HP 1100 series ESI-MS equipped with single quadruple). Compounds were eluted with methanol (0% for 6 min, followed by linear gradients to 56% in 15 min and to 80% in 1 min) in ammonium formate buffer (20 mM, pH 4.25 for cofactors 3, 4, 6 and pH 3.5 for cofactor 5) at a flow of 0.3 mL/min and detected at 280 nm. For on-line mass spectrometric detection post-column mobile phase modification (equal co-flow of 96% methanol, 4% formic acid and 1 mM sodium hydroxide) was used to enhance the detection efficiency of 2'-deoxycytidine and its derivatives. Mass spectra were recorded in 50-600 m/z range.

C.1 Duplex Oligodeoxynucleotide Analysis after Treatment with Cofactor 3 (—Z—R=—CH$_2$CH$_3$) and M.BcnIB (Comparison)

Figure 3A:
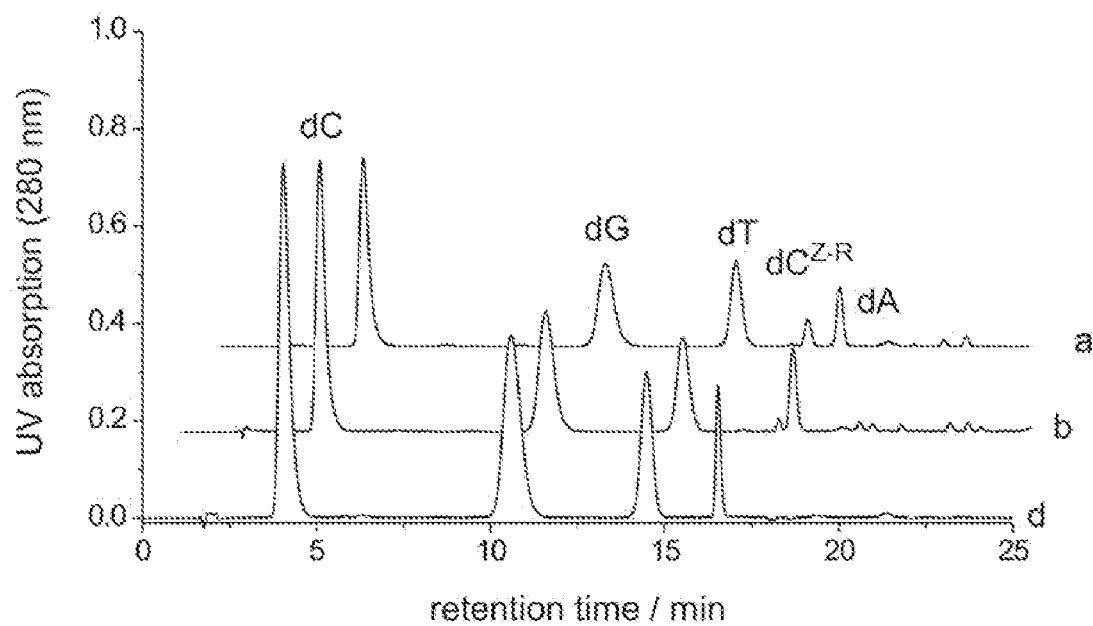
FIG. 3 is an HPLC analysis of enzymatically fragmented duplex oligodeoxynucleotides (V-VI)$^{Z-R}$ obtained after treatment with cofactors 3-6 and M.BcnIB. In $dC^{Z-R}$ the chemical group Z—R is attached to the N4 position of dC. Curve (a): cofactor 3 with Z=$CH_2$, and R=—$CH_3$; curve (b): cofactor 4 with Z=$CH_2$ and R=—$CH_2CH_3$; curve (c): cofactor 5 with $Z=CH_2$ and $R=\!\!-\!\!CH\!\!=\!\!CH_2$ and curve (d): cofactor 6 with $Z=CH_2$ and $R=\!\!-\!\!C\!\!\equiv\!\!CH$.
Figure 3B:
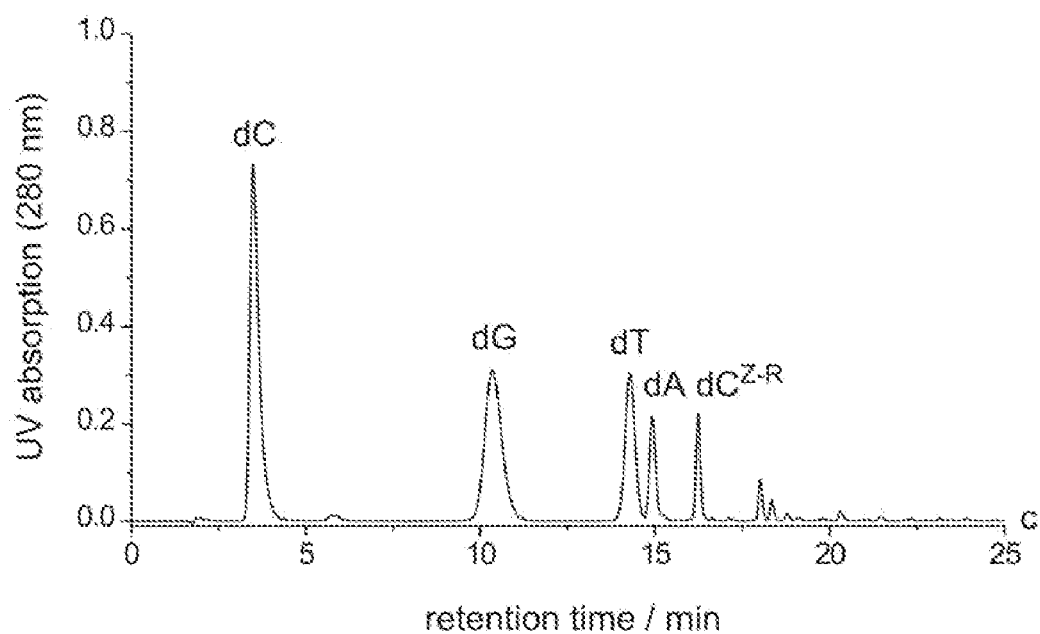

Fragmentation of the modified duplex oligodeoxynucleotide (V.VI)$^{Z\text{-}R}$ with —Z—R=—CH$_2$CH$_3$ (trace a in FIG. 3) revealed in addition to the natural nucleosides dC, dG, dT and dA a new compound with a retention time of 16.9 min. This new compound was analyzed by coupled ESI-MS and the observed mass (m/z: 278 [M+Na]$^+$, 162 [N4-ethyl-cytosine+Na]$^+$) is in agreement with N4-ethyl-2'-deoxycytidine (dC$^{N4\text{-}Ethyl}$). Thus, the AdoMet analog 3 functions as a cofactor for M.BcnIB.

C.2 Duplex Oligodeoxynucleotide Analysis after Treatment with Cofactor 4 (—Z—R=—CH$_2$CH$_2$CH$_3$) and M.BcnIB (Comparison)

Fragmentation of the duplex oligodeoxynucleotide (trace b in FIG. 3) revealed only the natural nucleosides dC, dG, dT and dA. Thus, the AdoMet analog 4 does not function as a cofactor for M.BcnIB.

C.3 Duplex Oligodeoxynucleotide Analysis after Treatment with Cofactor 5 (—Z—R=—CH$_2$CH=CH$_2$) and M.BcnIB Fragmentation of the modified duplex oligodeoxynucleotide (V.VI)$^{Z\text{-}R}$ with —Z—R=—CH$_2$CH=CH$_2$ (trace c in FIG. 3) revealed in addition to the natural nucleosides dC, dG, dT and dA a new compound with a retention time of 16.2 min. This new compound was analyzed by coupled ESI-MS and the observed mass (m/z: 290 [M+Na]$^+$, 174 [N4-propenyl-cytosine+Na]$^+$) is in agreement with N4-propenyl-2'-deoxycytidine (dC$^{N4\text{-}Propenyl}$). Thus, the AdoMet analog 5 functions as a cofactor for M.BcnIB.

C.4 Duplex Oligodeoxynucleotide Analysis after Treatment with Cofactor 6 (—Z—R=—CH$_2$C≡CH) and M.BcnIB Fragmentation of the duplex oligodeoxynucleotide (trace d in FIG. 3) revealed only the natural nucleosides dC, dG, dT and dA. Thus, the AdoMet analog 6 does not function as a cofactor for M.BcnIB.

Example 3

Sequence-Specific Modifications of Long DNA with Cofactors 3-9 and DNA Methyltransferases from Different Classes Transfer kinetics of the activated ethyl (—CH$_2$CH$_3$), propyl (—CH$_2$CH$_2$CH$_3$), prop-2-enyl (—CH$_2$CH=CH$_2$), prop-2-ynyl (—CH$_2$C≡CH), but-2-ynyl (—CH$_2$C≡CCH$_3$), pent-2-ynyl (—CH$_2$C≡CCH$_2$CH$_3$) and benzyl group (—CH$_2$C$_6$H$_5$) from cofactors 3-9 by the DNA adenine-N6 methyltransferase M.TaqI and its variant V21 G, the DNA cytosine-C5 methyltransferase M.HhaI and its variant Q82A, the DNA cytosine-N4 methyltransferase M.BcnIB and the DNA cytosine-C5 methyltransferase M.SssI variant Q142A to phage lambda DNA (48502 base pairs) were investigated using a DNA protection assay. This assay makes use of the fact that DNA methyltransferase-catalyzed modifications of nucleobases within the recognition sequences of restriction endonucleases can protect the DNA against fragmentation by these enzymes. The principle of the DNA protection assay is illustrated in Scheme 8 using the DNA adenine-N6 methyltransferase M.TaqI and the restriction endonuclease R.TaqI as an example. Unmodified DNA containing 5'-TCGA-3' recognition sequences is readily fragmentated by R.TaqI. After DNA modification by M.TaqI in the presence of a cofactor with an activated group Z—R modified 5'-TCGA$^{Z—R}$-3' sequences are formed and, as a result, R.TaqI is unable to fragment the modified DNA. Occurrence of fragmentation is then analyzed by agarose gel electrophoresis.

Scheme 8: Principle of the DNA protection assay used to quantify the enzymatic activities of the different DNA methyltransferases with the natural cofactor 1 and the cofactor analogs 3-9. The coupled enzymatic assay is illustrated for the DNA adenine-N6 methyltransferase M.TaqI using the restriction endonuclease R.TaqI to analyze DNA modifications at 5'-TCGA-3' sequences (5'-TCGA-3' recognition sequences of M.TaqI and R.TaqI are shown as solid boxes).

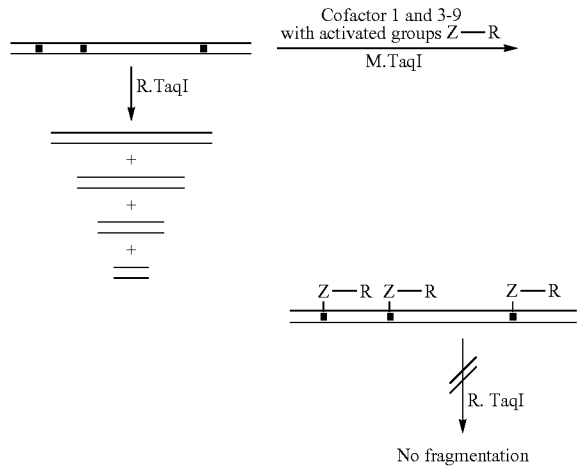

By varying the amounts of DNA methyltransferase, this assay is used to investigate the enzymatic activities of the different DNA methyltransferases with cofactors 3-9 and compare them to the enzymatic activities with the natural cofactor 1. The minimal amount of DNA methyltransferase needed to fully protect 1 μg of phage lambda DNA against restriction endonuclease fragmentation under the given experimental conditions is defined as one enzyme unit (u).

A.1 Enzymatic Activities of M.TaqI (Wild-Type Enzyme) with the Different Cofactors 1 and 3-9

Two fold serial dilutions (20 μL) of M.TaqI (starting with 200 ng, 4.18 μmol; produced as described in Goedecke et al., (2001) Nature Struct. Biol. 8, 121-125) in buffer (20 mM Tris acetate, 50 mM potassium acetate, 10 mM magnesium acetate, 1 mM dithiothreitol, and 0.01% Triton X-100, pH 7.9) containing bovine serum albumin (0.1 mg/mL), phage lambda DNA (1 μg, 31.3 fmol, 121 5'-TCGA-3' recognition sequences, 3.78 μmol recognition sequences, MBI Fermentas) and the natural cofactor 1 (300 μM) or cofactor analogs 3-9 (300 μM) were incubated at 60° C. for 4 h. Afterwards a solution (30 μL) containing R.TaqI restriction endonuclease (40 u, MBI Fermentas), bovine serum albumin (0.166 mg/mL) and buffer (16.6 mM Tris hydrochloride, 166 mM sodium chloride, 8.3 mM magnesium chloride, pH 8.0) was added to each dilution and incubation at 60-65° C. was continued for 15 min. Loading buffer (10 μL, 0.25% bromphenol blue, 30% glycerol) was added to each sample, and aliquots (12 μL) were analyzed for the degree of protection by agarose gel (1%) electrophoresis. Parallel control experiments were performed with phage lambda DNA in the absence of M.TaqI and in the presence of M.TaqI (200 ng).

The following specific activities of M.TaqI with the natural cofactor 1 or cofactor analogs 3-9 were observed under the given experimental conditions (FIG. 4): 1 40960 u/μg, 3 10 u/μg, 4<5 u/μg, 5 80 u/μg, 6 10 u/μg, 7 1280 u/μg, 8 640 u/μg and 9 640 u/μg. These results demonstrate that chemical groups larger than methyl can be transferred by M.TaqI with substantial activity provided that the carbon next to the sulfonium center is further activated by a flanking carbon-carbon double bond (allylic system), a flanking carbon-carbon triple bond (propargylic system) or a flanking aromatic ring (benzylic system).

A.2 Enzymatic Activities of M.TaqI Variant V21G with the Different Cofactors 1 and 3-9

A structural comparison between the three-dimensional of M.TaqI in complex with DNA and a non-reactive cofactor analog (Goedecke et al., (2001) Nature Struct. Biol. 8, 121-125) and the three-dimensional of M.TaqI in complex with the natural cofactor 1 (Labahn et al., (1994) Proc. Natl. Acad. Sci. USA 91, 10957-10961) suggested that V21 could lead to unfavorable steric interactions with cofactor analogs containing extended methyl group replacements. Therefore, the codon for V21 was changed to a codon for glycine by standard PCR mutagenesis (Ho et al., (1989) Gene 77, 51-59) and the correct DNA sequence of the complete gene was verified by DNA sequencing. Expression and purification of the V21G variant was performed as described for the wild-type enzyme (Holz et al., (1998) Nucleic Acids Res. 26, 1076-1083; Goedecke et al., (2001) Nature Struct. Biol. 8, 121-125). The DNA protection assay with the V21G variant was performed as described for the wild type (Example 3A.1).

The following specific activities of M.TaqI-V21G with the natural cofactor 1 or cofactor analogs 3-9 were observed (FIG. 5): 1 320 u/μg, 3 5 u/μg, 4<5 u/μg, 5 640 u/μg, 6 20 u/μg, 7 80 u/μg, 8 80 u/μg and 9 2560 u/μg. The V21G variant of M.TaqI is more active with cofactor 5 and 9 than with the natural cofactor 1. In addition, the V21G variant possesses a substantial higher activity with cofactors 5, 6 and 9 than the wild-type enzyme.

B.1 Enzymatic Activities of M.HhaI (Wild-Type Enzyme) with the Different Cofactors 1 and 3-8

Two fold serial dilutions (15 μL) of M.HhaI (starting with 278 ng, 7.5 μmol; produced as described in Kumar et al., (1992) Biochemistry 31, 8648-8653 and Klimasauskas et al., (1998) EMBO J. 17, 317-324) in buffer (50 mM Tris hydrochloride, 10 mM sodium chloride, 0.5 mM ethylenediaminetetraacetic acid, 2 mM 2-mercaptoethanol, pH 7.4 for cofactors 3-5, 7 and 8; 25 mM 3-morpholino-propanesulfonic acid, 25 mM 2-morpholino-ethanesulfonic acid, 10 mM sodium chloride, 0.5 mM ethylenediaminetetraacetic acid, 2 mM 2-mercaptoethanol, pH 6.0 for cofactor 6) containing bovine serum albumin (0.2 mg/mL), phage lambda DNA (1.16 μg, 36.3 fmol, 215 5'-GCGC-3' recognition sequences, 7.8 μmol recognition sequences, MBI Fermentas) and the natural cofactor 1 (300 μM) or cofactor analogs 3-8 (300 μM) were incubated at 37° C. for 4 h. Afterwards, the reactions were stopped by heating to 80° C. for 10 min. A solution (10 μL) containing R.Hin6I (restriction endonuclease which recognizes the same sequence as M.HhaI and does not cleave modified DNA) (12 u, MBI Fermentas), bovine serum albumin (0.1 mg/mL) and buffer (33 mM Tris acetate, 66 mM potassium acetate, 26.5 mM magnesium chloride, pH 7.9) was added to each dilution and incubation at 37° C. was continued for 1 h. Orange Loading Dye Solution (5 μL, 0.2% orange G, 0.05% xylene cyanol FF, 60 mM ethylenediaminetetraacetic acid, 60% glycerol, MBI Fermentas) was added to each sample, and aliquots (15 μL) were analyzed for the degree of protection by agarose gel (1%) electrophoresis. Parallel control experiments were performed with phage lambda DNA in the absence of M.HhaI and in the presence of M.HhaI (278 ng).

The following specific activities of M.HhaI with the natural cofactor 1 or cofactor analogs 3-8 were observed under the given experimental conditions (FIG. 6): 1 460 u/μg, 3<4 u/μg, 4 0 u/μg, 5 7 u/μg, 6<4 u/μg, 7 29 u/μg and 8 <4 u/μg. These results demonstrate that chemical groups larger than methyl can be transferred by M.HhaI with substantial activity provided that the carbon next to the sulfonium center is further activated by a flanking carbon-carbon double bond (allylic system) or a flanking carbon-carbon triple bond (propargylic system).

B.2 Enzymatic Activities of M.HhaI Variant Q82A with the Different Cofactors 1 and 3-8

The DNA protection assay with the M.HhaI variant Q82A (see Example 2B) was performed as described for the wild type enzyme (Example 3B.1).

The following specific activities of M.HhaI-Q82A with the natural cofactor 1 or cofactor analogs 3-8 were observed (FIG. 7): 1 1115 u/μg, 3 7 u/μg, 4 0 u/μg, 5 29 u/μg, 6<4 u/μg, 7 58 u/μg and 8<4 u/μg. The Q82A variant possesses higher activities with cofactors carrying enlarged methyl group replacements (except cofactor 4) in comparison to wild-type M.HhaI.

C. Enzymatic Activities of M.BcnIb (Wild-Type Enzyme) with the Different Cofactors 1 and 3-8

Two fold serial dilutions (15 μL) of M.BcnIB (starting with 144 ng, 3.8 pmol) in buffer (50 mM Tris hydrochloride, 10 mM sodium chloride, 0.5 mM ethylenediaminetetraacetic acid, 2 mM 2-mercaptoethanol, pH 7.4 for cofactors 3-5, 7 and 8; 25 mM 3-morpholino-propanesulfonic acid, 25 mM 2-morpholino-ethanesulfonic acid, 10 mM sodium chloride, 0.5 mM ethylenediaminetetraacetic acid, 2 mM 2-mercaptoethanol, pH 6.0 for cofactor 6) containing bovine serum albumin (0.2 mg/mL), phage lambda DNA (1.10 μg, 34.4 pmol, 114 5'-CCSGG-3' recognition sequences, S=C or G, 3.9 pmol recognition sequences, MBI Fermentas) and the natural cofactor 1 (300 μM) or cofactor analogs 3-8 (300 μM) were incubated at 37° C. for 4 h. Afterwards the reactions were stopped by heating to 80° C. for 10 min. A solution (10 μL) containing R.BcnI restriction endonuclease (12 u, MBI Fermentas), bovine serum albumin (0.1 mg/mL) and buffer (33 mM Tris acetate, 66 mM potassium acetate, 26.5 mM magnesium chloride, pH 7.9) was added to each dilution and incubation at 37° C. was continued for 1 h. Orange Loading Dye Solution (5 μL, 0.2% orange G, 0.05% xylene cyanol FF, 60 mM ethylenediaminetetraacetic acid, 60% glycerol, MBI Fermentas) was added to each sample, and aliquots (15 μL) were analyzed for the degree of protection by agarose gel (1%) electrophoresis. Parallel control experiments were performed with phage lambda DNA in the absence of M.BcnIB and in the presence of M.BcnIB (144 ng).

The following specific activities of M.BcnIB with the natural cofactor 1 or cofactor analogs 3-8 were observed under the given experimental conditions (FIG. 8): 1 444 u/μg, 3<7 u/μg, 4<7 u/μg, 5<7 u/μg, 6 0 u/μg, 7 28 u/μg and 8 14 u/μg. These results demonstrate that chemical groups larger than methyl can be transferred by M.BcnI with substantial activity provided that the carbon next to the sulfonium center is further activated by a flanking carbon-carbon triple bond (propargylic system).

D. Enzymatic Activities of M.SssI Variant Q142A with the Different Cofactors 1, 5 and 7

M.SssI is a DNA cytosine-C5 methyltransferase and recognizes the short double-stranded 5'-CG-3' DNA sequence. The wild-type enzyme shows almost no enzymatic activity with the cofactors 3-6. However, a three-dimensional structural model of M.SssI (Koudan et al., (2004) J. Biomol. Struct. Dyn. 22, 339-346) suggested that Q142 (homologous to Q82 in M.HhaI) could lead to unfavorable steric interactions with cofactor analogs containing extended methyl group replacements. Therefore, the codon for Q142 was changed to a codon for alanine by standard PCR mutagenesis (Ho et al., (1989) Gene 77, 51-59) and the correct DNA sequence of the complete gene was verified by DNA sequencing.

Two fold serial dilutions (20 μL) of M.SssI-Q142A (starting with 3300 ng, 73 pmol) in buffer (10 mM Tris hydrochloride, 50 mM sodium chloride, 1 mM dithiothreitol, pH 7.9), phage lambda DNA (1 μg, 31.3 fmol, 3113 5'-CG-3' recognition sequences, 97 μmol recognition sequences, MBI Fermentas) and the natural cofactor 1 (300 μM) or cofactor analogs 5 and 7 (300 μM) were incubated at 37° C. for 4 h. Afterwards the reactions were stopped by heating to 65° C. for 20 min. Solutions of magnesium chloride (1 μL, 200 mM) and R.BstUI restriction endonuclease (1 μL, 10 u, New England Biolabs), were added to each dilution and incubation at 60° C. was continued for 1 h. Loading buffer (10 μL, 0.25% bromphenol blue, 30% glycerol) was added to each sample, and aliquots (15 μL) were analyzed for the degree of protection by agarose gel (1%) electrophoresis. A parallel control assay performed in the absence of any cofactor did not lead to full protection of phage lambda DNA.

Figure 9:
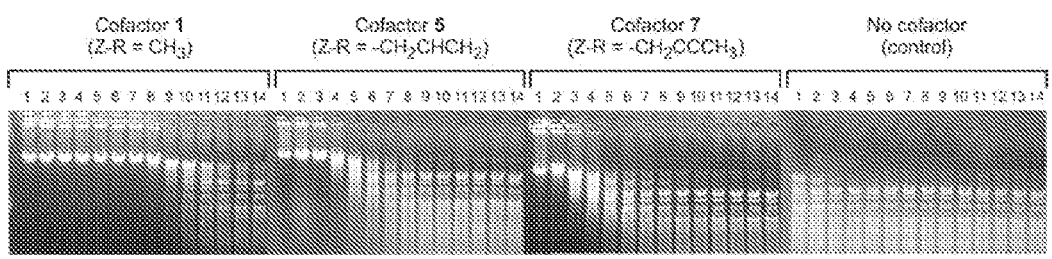
FIG. 9 shows the result of a DNA protection assay for M.SssI variant Q142A-catalyzed transfer of different chemical groups Z—R from the natural cofactor 1 and cofactor analogs 5 and 7 to phage lambda DNA. DNA (1 µg) and cofactors (300 µM) were first incubated with different amounts of M.SssI-Q142A (two fold serial dilutions from lanes 1 to 14 starting with 3300 ng in lanes 1) and then subjected to fragmentation by R.BstUI. A parallel control experiment with phage lambda DNA was performed in the absence of cofactor.

The following specific activities of M.SssI-Q142A with the natural cofactor 1 or cofactor analogs 5 and 7 were observed under the given experimental conditions (FIG. 9): 1 20 u/μg, 5 1.2 u/μg and 7 0.6 u/μg. These results demonstrate that chemical groups larger than methyl can be transferred by the Q142A variant of M.SssI with substantial activity.

Example 4

Sequence-Specific Two-Step DNA Labeling

Sequence-specific DNA labeling was achieved by DNA methyltransferase-catalyzed transfer of an activated side chain containing a primary amino group (cofactor analog 10) followed by chemo-selective modification with an amine-reactive fluorescent label (two-step labeling).

A. Synthesis of Cofactor Analog 10

Chemical synthesis of cofactor analog 10 (Z=—CH$_2$ and R=—C≡CCH$_2$NHCOCH$_2$CH$_2$CH$_2$NH$_2$) with a primary amino group in the side chain was performed as shown in Scheme 9.

Scheme 9: Chemical syntheses of cofactor analog 10 according to the present invention.

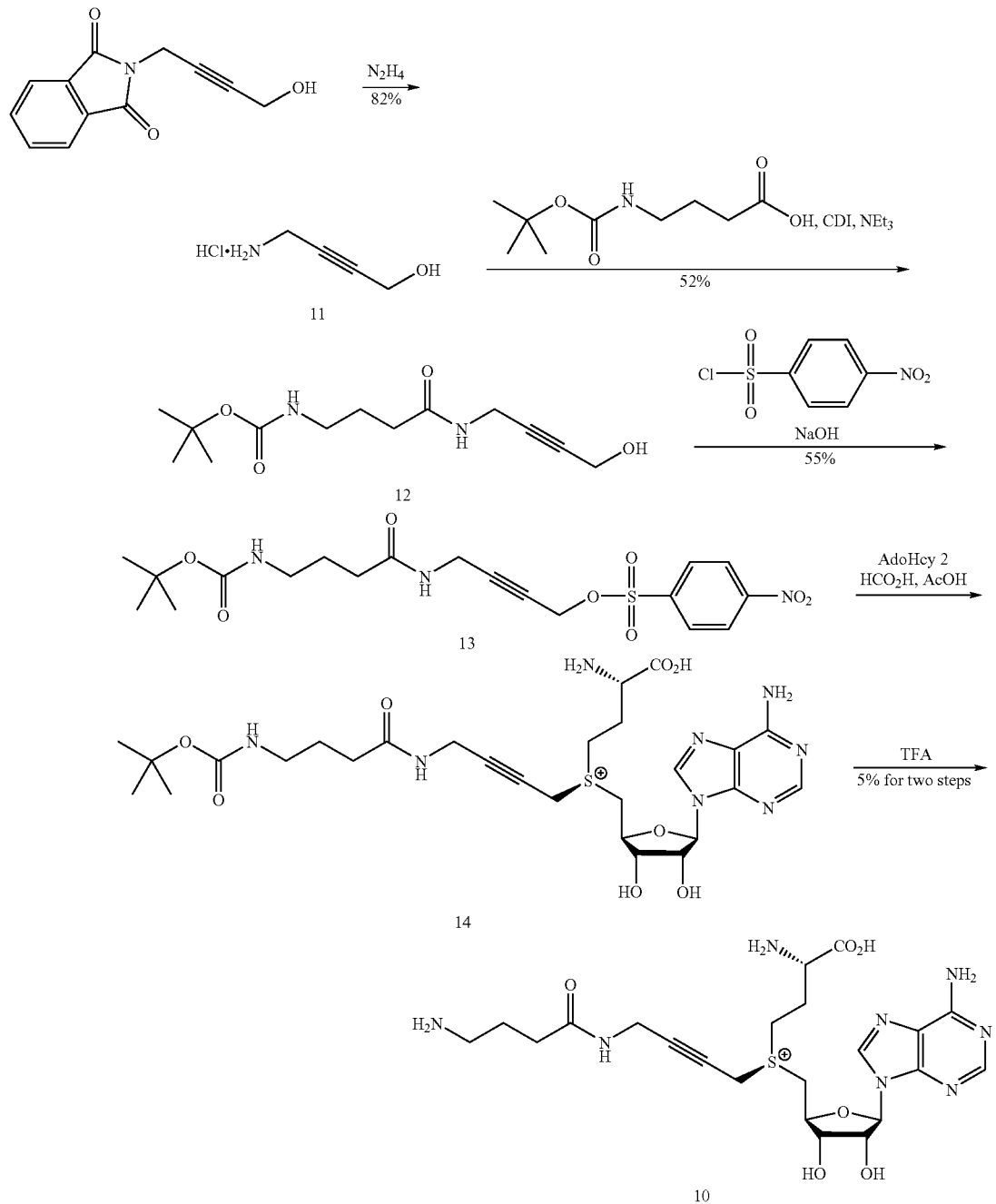

A.1 4-Aminobut-2-yn-1-ol Hydrochloride, Compound 11

To 4-Phthalimidobut-2-yn-1-ol (7.66 g, 35.6 mmol, prepared according to Thomson et al., (2003) Synth. Commun. 33, 3631-3641) in methanol (150 mL) was added hydrazine hydrate (3.46 mL, 71.2 mmol). The reaction mixture was heated at reflux for 2 h and after cooling to room temperature the solvent was removed under reduced pressure. Water and ethanol (100 mL, 1:1 mixture) and conc. hydrochloric acid (100 mL) were added to the residue. The mixture was heated at reflux for 20 min and the precipitate removed by filtration. The filtrate was concentrated under reduced pressure and the resulting residue crystallized from methanol to yield compound II (3.57 g. 82%) as a white solid.

$^1$H-NMR (300 MHz, D$_2$O): δ=3.77 (t, $^4$J=2.0 Hz, 2H, CH$_2$), 4.18 (t, $^4$J=2.0, 2H, CH$_2$); $^{13}$C-NMR (75 MHz, D$_2$O): δ=32.09, 52.23, 79.15, 87.96.

A.2 4-[(tert.-Butoxycarbonylamino)butanamido]but-2-yn-1-ol, Compound 12

4-[(tert.-butoxycarbonyl)amino]butanoic acid (5.20 g, 25.6 mmol, prepared in analogy to Houssin et al., (1988)

Synthesis 3, 259-261) was dissolved in anhydrous tetrahydrofuran (20 mL), carbonyldiimidazole (CDI) (4.56 g, 28.1 mmol) was added and the resulting clear solution was stirred at room temperature for 2 h. Then, the primary amine 11 (3.11 g 25.6 mmol) and trietylamine (7.10 mL, 50.9 mmol) were added and stirring was continued at room temperature for 2 h. The solvent was removed under reduced pressure and the crude product was purified by column chromatography (silica gel, 40 g, chloroform/ethylacetate 1:1) to give compound 12 (3.59 g, 52%) as a light yellow oil ($R_f$ 0.3, chloroform/ethyl acetate 1:1).

$^1$H-NMR (300 MHz, CDCl$_3$): δ=1.41 (s, 9H, CH$_3$), 1.78 (quint, $^3$J=6.8 Hz, 2H, CH$_2$), 2.22 (t, $^3$J=7.1 Hz, 2H, CH$_2$), 3.13 (q, $^3$J=6.4 Hz, 2H, CH$_2$), 4.03-4.09 (m, 2H, CH$_2$), 4.09-4.14 (m, 2H, CH$_2$), 4.84 (br. s, 1H, NH), 6.67 (br. s, 1H, NH); $^{13}$C-NMR (75 MHz, CDCl$_3$): δ=26.38, 28.64, 29.62, 33.52, 40.05, 50.74, 79.63, 81.22, 81.86, 153.87, 171.53.

A.3 4-[4-(tert.-Butoxycarbonylamino)butanamido]but-2-ynyl 4-nitrobenzenesulfonate, Compound 13

To a solution of alcohol 12 (1.0 g, 3.7 mmol) in methylene chloride (15 mL) 4-nitrobenzenesulfonyl chloride (0.90 g, 4.07 mmol) and sodium hydroxide (0.74 g, 18.5 mmol) were added at 0° C. The resulting solution was stirred at room temperature for 3 h. Then, cold water (20 mL) was added, the reaction mixture extracted with methylene chloride (3×10 mL) and the combined organic layers dried over sodium sulfate. After filtration the solvent removed under reduced pressure to yield compound 13 (0.93 g, 55%) as a light yellow solid.

$^1$H-NMR (300 MHz, CDCl$_3$): δ=1.43 (s, 9H, CH$_3$), 1.76 (quint, $^3$J=6.6 Hz, 2H, CH$_2$), 2.19 (t, $^3$J=7.1, 2H, CH$_2$), 3.13 (q, $^3$J=6.4 Hz, 2H, CH$_2$), 3.92 (dt, $^4$J=1.8 Hz, $^3$J=5.3 Hz, 2H, CH$_2$), 4.74 (br. s, 1H, NH), 4.83 (t, $^4$J=1.8 Hz, 2H, CH$_2$), 6.61 (br. s, 1H, NH), 8.09-8.17 (m, 2H, arom. H), 8.38-8.45 (m, 2H, arom. H); $^{13}$C-NMR (75 MHz, CDCl$_3$): δ=26.96, 28.64, 29.26, 33.37, 39.66, 59.33, 74.19, 79.89, 87.08, 124.69, 129.74, 142.36, 151.20, 162.76, 172.64.

A.4 5'-[(S)-[(3S)-3-Amino-3-carboxypropyl]-4-[4-(tert.-butoxycarbonylamino)butanamido]but-2-ynyl-sulfonio]-5'-deoxyadenosine, Compound 14

S-Adenosyl-L-homocysteine (2) (20 mg, 52 µmol) was dissolved in a 1:1 mixture of formic acid and acetic acid (0.4 mL) and sulfonate 13 (16 equivalents) was added at 0° C. The solution was allowed to warm up at room temperature and incubated at room temperature with shaking. The progress of the reaction was analyzed by analytical reversed-phase HPLC as described in Example 1 for cofactors 7 and 8 except that compounds were eluted with a linear methanol gradient (to 80% in 5 min and then 80% for 3 min) at 30° C. using a Discovery HS C18 reversed-phase column (75×2.1 mm, 3 µm, Supelco, Germany) equipped with a Supelguard Discovery HS C18 pre-column (20×2.1 mm, 5 µm).

The reaction was quenched by adding water (4 mL) after 8 h and the aqueous phases were extracted with diethyl ether (3×4 mL). The aqueous phase containing compound 14 was removed under reduced pressure and the resulting light yellow oil was dissolved in ammonium formate buffer (10 mL, 20 mM, pH 3.5). Purification was performed by preparative reversed-phase HPLC (Discovery HS C18 150×10 mm, 5 µm, equipped with a Supelguard Discovery HS C18 10×10 mm, 5 µm pre-column, Supelco, Germany). Compounds were eluted with methanol (linear gradients from 10% to 13.2% in 9 min and to 80% in 2 min followed by 80% for 2 min) in aqueous ammonium formate (20 mM, pH 3.5) and a flow of 4.0 mL/min at 30° C. and detected at 210 nm, 260 nm and 280 nm. The product 14 and its epimer at sulfur eluted with a retention time of 9.3 min and 8.8 min, respectively. Product containing fractions were collected and solvents quickly removed under reduced pressure.

ESI-MS m/z (relative intensity): 637.3 (100) [M]$^+$, 536.2 (15) [5'-(4-(4-(tert.-butoxycarbonylamino)butanamido)but-2-ynyl)thio-5'-deoxyadenosine+H]$^+$, 558.2 (12) [5'-(4-(4-(tert-butoxycarbonylamino)butanamido)but-2-ynyl)thio-5'-deoxy-adenosine+Na]$^+$, 250.1 (10) [5'-deoxyadenosine]$^+$.

A.5 5'-[(S)-[(3S)-3-Amino-3-carboxypropyl]-4-[4-aminobutanamido]but-2-ynylsulfonio]-5'-deoxyadenosine, Cofactor 10

Compound 14 was dissolved in water and deprotection was carried out by adding two volumes of trifluoroacetic acid. The progress of the reaction was analyzed by analytical reversed-phase HPLC (see Example 4A.4) and cofactor 10 eluted with a retention time of 3.2 min. After incubation at room temperature for 1 h solvents were removed under reduced pressure and the residue was dissolved in aqueous ammonium formate buffer (20 mM, pH 3.5).

Purification was performed by reversed-phase column chromatography (reversed-phase silica gel 100 C18, Fluka) and compounds were eluted with ammonium formate buffer (20 mM, pH 3.5) containing 5% acetonitrile. Product containing fractions were collected, solvents removed under reduced pressure and the residue was dissolved in water. The amount of product 10 (2.5 µmol, 5% for the last two steps) was determined by UV spectroscopy using an extinction coefficient of 15400 L mol$^{-1}$ cm$^{-1}$ at 260 nm for the adenine chromophore.

ESI-MS m/z (relative intensity): 537.3 (25) [M]$^+$, 458.1 (33) [5'-(4-(4-aminobutanamido)but-2-ynyl)thio-5'-deoxy-adenosine+Na]$^+$, 436.2 (100) [5'-(4-(4-aminobutanamido)but-2-ynyl)thio-5'-deoxyadenosine+H]$^+$.

B. Sequence-Specific Modification of Short Duplex Oligodeoxynucleotides with Cofactor 10 and DNA Methyltransferases from Different Classes Transfer of the activated 4-(4-aminobutanamido)but-2-ynyl group (Z—R=—CH$_2$C≡CCH$_2$NHCOCH$_2$CH$_2$NH$_2$) from cofactor 10 by the DNA adenine-N6 methyltransferase M.TaqI and the DNA cytosine-C5 methyltransferase M.HhaI variant Q82A/N304A was first investigated using short duplex oligodeoxynucleotides as substrates. After enzymatic transfer the duplex oligodeoxy-nucleotides were enzymatically fragmented and the resulting modified nucleosides were analyzed by reversed-phase HPLC coupled with ESI-MS.

B.1 Modification of Adenine-N6 within a Duplex Oligodeoxynucleotide by M.TaqI

The hemimethylated duplex oligodeoxynucleotide I.II (compare Scheme 5, Example 2A) was produced by mixing equal molar amounts of complementary single-stranded oligodeoxynucleotide I (5'-GCCGCTCGATGCCG-3') (SEQ. ID NO. 1) and II (5'-CGGCATCGA$^{Me}$GCGGC-3', A$^{Me}$=N6-methyl-2'-deoxyadenosine) (SEQ ID NO. 2) in water, heating at 85° C. for 5 min and slow cooling to room temperature. Enzymatic modification was performed by incubation of duplex oligodeoxynucleotide I.II (10 µM) with cofactor 10 (300 µM) and M.TaqI (12.5 µM, produced as described in Goedecke et al., (2001) Nature Struct. Biol. 8, 121-125) in buffer (20 mM Tris-acetate, 50 mM potassium acetate, 10 mM magnesium acetate, 1 mM dithiothreitol, 0.01% Triton X-100 reduced, pH 7.9) at 37° C. over night. The solution was heated to 95° C. for 10 min, supplemented with Proteinase K and incubated at 55° C. for 2 h. Hydrolysis products were removed by gel filtration (G-25 column, Amersham Biosciences).

The obtained solution was treated with buffer (1/10 volume, 100 mM Tris hydrochlorid, 100 mM magnesium chloride, 10 mM zinc acetate, pH 7.5) containing Nuclease P1 (1.14 u, Sigma, Taufkirchen, Germany) and calf intestine alkaline phosphatase (18 u, MBI Fermentas), incubated at 42° C. for 4 h and passed through a Microcon YM-3 spin column (Amicon). Nucleosides were analyzed by reversed-phase HPLC (Discovery HS C18 75×2.1 mm, 3 µm, equipped with a Supelguard Discovery HS C18 20×2.1 mm, 5 µm, pre-column, Supelco, Germany) coupled with a mass spectrometric detector (HP 1100 series ESI-MS equipped with single quadruple). Compounds were eluted with methanol (0% for 3 min, followed by linear gradients to 20% in 15 min and to 80% in 2 min) in ammonium formate buffer (20 mM, pH 3.5) at a flow of 0.3 mL/min. For on-line mass spectrometric detection post-column mobile phase modification (equal co-flow of 96% methanol, 4% formic acid and 1 mM sodium hydroxide) was used to enhance the detection efficiency of 2'-deoxyadenosine, 2'-deoxycytidine and their derivatives. Mass spectra were recorded in 50-600 m/z range.

Fragmentation of the modified duplex oligodeoxynucleotide $I^{Z-R}$.II with —Z—R═ $CH_2C$≡$CCH_2NHCOCH_2CH_2CH_2NH_2$ (curve a in FIG. 10, upper) revealed in addition to the natural nucleosides dC, dG, dT, dA and $dA^{Me}$ a new compound with a longer retention time (19.1 min) than $dA^{Me}$. This new compound was analyzed by coupled ESI-MS and the observed masses (m/z: 426 [M+Na]$^+$, 310 [N6-(4-(4-aminobutanamido)but-2-ynyl)adenine+Na]$^+$) are in agreement with N6-[4-(4-aminobutanamido)but-2-ynyl]-2'-deoxyadenosine ($dA^{4-(4-Aminobutanamido)but-2-ynyl}$). The experimental determined nucleotide composition of the modified duplex oligodeoxynucleotide $I^{Z-R}$.II was found to be in good agreement with the theoretical nucleotide composition (given in brackets): dC 10.2 (11), dG 11.8 (11), dT 3.0 (3), dA 1.0 (1), $dA^{Me}$ 1.0 (1) and $dA^{4-(4-Aminobutanamido)but-2-ynyl}$ 1.1 (1). Thus, the AdoMet analog 10 functions as a cofactor for M.TaqI.

B.2 Modifications of Cytosine-C5 within a Duplex oligodeoxynucleotide by the M.HhaI variant Q82A/N304A The three-dimensional structure of M.HhaI in complex with DNA and the natural cofactor AdoMet 1 (PDB id: 6 MHT; Kumar et al., (1997) Nucleic Acids Res. 25, 2773-2783) suggested that N304 (in addition to Q82) could lead to unfavorable steric interactions with cofactor analogs containing extended methyl group replacements. Therefore, the codon for N304 was changed to a codon for alanine by standard Megaprimer PCR mutagenesis (Sambrook and Russell, (2001) Cold Spring Harbor Laboratory Press, 13.31-13.35) and the fragment containing this mutation was cloned into the plasmid containing the Q82A mutation (Example 2B, Example 3B.2. The correct DNA sequence of the complete gene was verified by DNA sequencing. Expression and purification of the Q82A/N304A variant was performed as described for the wild-type enzyme (Kumar et al., (1992) Biochemistry 31, 8648-8653; Klimasauskas et al., (1998) EMBO J. 17, 317-324). The presence of the amino acid substitution was verified by mass spectrometric analysis of purified M.HhaI-Q82A/N304A.

The duplex oligodeoxynucleotide III.IV (compare Scheme 6, Example 2B) was produced by mixing equal molar amounts (2.5 nmol) of complementary single-stranded oligodeoxynucleotide III (5'-CATTACGCGCCGGGTCCTGG CTAT-3') (SEQ ID NO. 3) and IV (5'-ATAGCCAGGAC- CCGGCGCGTAATG-3') (SEQ. ID NO. 4) in water, heating at 85° C. for 5 min and slow cooling to room temperature. Enzymatic modification was performed by incubation of duplex oligodeoxynucleotide III.IV (10 µM) with cofactor 10 (300 µM) and M.HhaI-Q82A/N304A (12.5 µM) in buffer (50 mM Tris hydrochloride, 15 mM sodium chloride, 0.5 mM ethylenediaminetetraacetic acid, 2 mM 2-mercaptoethanol, 0.2 mg/mL bovine serum albumin) at 37° C. over night. The solution was heated to 80° C. for 10 min, supplemented with Proteinase K and incubated at 55° C. for 2 h. Hydrolysis products were removed by gel filtration (G-25 column, Amersham Biosciences). Enzymatic fragmentation and ESI-MS-coupled reversed-phase HPLC analysis of resulting nucleosides was performed as described under Example 4B.1).

Fragmentation of the modified duplex oligodeoxynucleotide (III.IV)$^{Z-R}$ with —Z—R═ $CH_2C$≡$CCH_2NHCOCH_2CH_2CH_2NH_2$ (curve a in FIG. 10, lower) revealed in addition to the natural nucleosides dC, dG, dT and dA a new compound with a retention time of 11.5 min. This new compound was analyzed by coupled ESI-MS and the observed masses (m/z: 402 [M+Na]$^+$, 286 [C5-(4-(4-aminobutanamido)but-2-ynyl)cytosine+Na]$^+$) are in agreement with C5-[4-(4-aminobutanamido)but-2-ynyl]-2'-deoxycytidine ($dC^{C5-[4-(4-Aminobutanamido)but-2-ynyl]}$). Thus, the AdoMet analog 10 functions as a cofactor for M.HhaI-Q82A/N304A.

C. Sequence-Specific Modification of Long DNA with Cofactor 10 and DNA Methyltransferases from Different Classes Enzymatic activities of the DNA adenine-N6 methyltransferase M.TaqI and the DNA cytosine-C5 methyltransferase M.HhaI variant Q82A/N304A with the cofactor 10 were investigated using a DNA protection assay (compare Scheme 8, Example 3).

C.1 Enzymatic Activity of M.TaqI (Wild-Type Enzyme) with the Cofactor 10

Two fold serial dilutions (15 µL) of M.TaqI (starting with 180 ng, 3.75 µmol; produced as described in Goedecke et al., (2001) Nature Struct. Biol. 8, 121-125) in buffer (20 mM Tris acetate, 50 mM potassium acetate, 10 mM magnesium acetate, 1 mM dithiothreitol, and 0.01% Triton X-100 reduced, pH 7.9), phage lambda DNA (1.03 µg, 32.3 fmol, 121 5'-TCGA-3' recognition sequences, 3.91 pmol recognition sequences, MBI Fermentas) and the cofactor analog 10 (300 µM) were incubated at 60° C. for 1 h. Afterwards a solution (10 µL) containing R.TaqI restriction endonuclease (10 u, MBI Fermentas), bovine serum albumin (0.1 mg/mL) and buffer (33 mM Tris acetate, 66 mM potassium acetate, 10 mM magnesium acetate, pH 7.9) was added to each dilution and incubation was continued at 65° C. for 1 h. Orange Loading Dye Solution (5 µL, 0.2% orange G, 0.05% xylene cyanol FF, 60 mM ethylenediaminetetraacetic acid, 60% glycerol, MBI Fermentas) was added to each sample, and aliquots (15 µL) were analyzed for the degree of protection by agarose gel (1%) electrophoresis. Parallel control experiments were performed with phage lambda DNA in the absence of M.TaqI and in the presence of M.TaqI (180 ng).

Figure 11A:
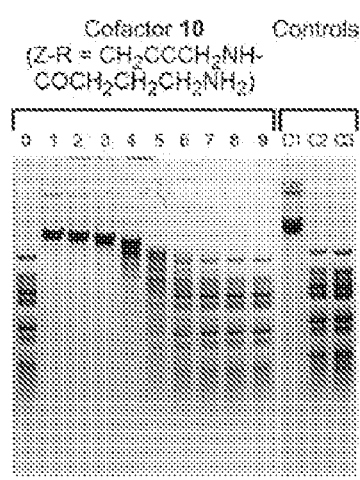
FIG. 11 shows the results of DNA protection assays for DNA methyltransferase-catalyzed transfer of the chemical group Z—R with $Z=CH_2$, and $R=\!\!-\!\!C\!\!\equiv\!\!CCH_2NHCOCH_2CH_2CH_2NH_2$ from cofactor analog 10 to phage lambda DNA. Left: DNA (1.03 µg) and cofactor 10 (300 µM) were first incubated with different amounts of M.TaqI (two fold serial dilutions from lanes 1 to 9 starting with 180 ng in lane 1; M.TaqI is absent in lane 0) for 1 h and then subjected to fragmentation by R.TaqI. Parallel control experiments with phage lambda DNA were performed in the absence of M.TaqI and cofactor 10 (C1 without R.TaqI and C2 with R.TaqI) and in the presence of M.TaqI (C3 with R.TaqI). Right: DNA (1.16 µg) and cofactor 10 (300 µM) were first incubated with different amounts of M.HhaI-Q82A/N304A (two fold serial dilutions from lanes 1 to 9 starting with 1100 ng in lane 1; M.HhaI-Q82A/N304A is absent in lane 0) for 1 h and then subjected to fragmentation by R.Hin6I. Parallel control experiments with phage lambda DNA were performed in the absence of M.HhaI-Q82A/N304A and cofactor 10 (C1 without R.Hin6I and C2 with R.Hin6I) and in the presence of M.HhaI-Q82A/N304A (C3 with R.Hin6I).
Figure 11B:
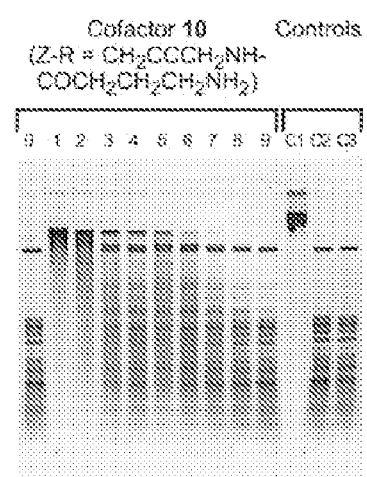

The specific activity of M.TaqI with the cofactor 10 (FIG. 11, left) under the given experimental conditions was 11 u/µg. For comparing the specific activities of M.TaqI obtained with cofactors 1, 3-9 given in Example 3A.1 this number should be multiplied by a factor of four because incubation with M.TaqI was only for 1 h and not for 4 h as used for Example 3A.1. The obtained result demonstrates that an elongated and amino-functionalized side chain can be transferred by M.TaqI with substantial activity provided that the carbon next to the sulfonium center is further activated by a flanking carbon-carbon triple bond (propargylic system).

C.2 Enzymatic Activity of M.HhaI Variant Q82A/N304A with the Cofactor 10

Two fold serial dilutions (15 µL) of M.HhaI variant Q82A/N304A (starting with 1100 ng, 30 µmol; produced as described in Example 4B.2) in buffer (50 mM Tris hydrochloride, 15 mM sodium chloride, 0.5 mM ethylenediaminetetraacetic acid, 2 mM 2-mercaptoethanol, pH 7.4) containing bovine serum albumin (0.2 mg/mL), phage lambda DNA (1.16 µg, 36.3 fmol, 215 5'-GCGC-3' recognition sequences, 7.8 µmol recognition sequences, MBI Fermentas) and the cofactor analog 10 (300 µM) were incubated at 37° C. for 1 h. Afterwards, the reactions were stopped by heating to 80° C. for 10 min. A solution (10 µL) containing R.Hin6I (restriction endonuclease which recognizes the same sequence as M.HhaI and does not cleave modified DNA) (12 u, MBI Fermentas), bovine serum albumin (0.1 mg/mL) and buffer (33 mM Tris acetate, 66 mM potassium acetate, 26.5 mM magnesium chloride, pH 7.9) was added to each dilution and incubation at 37° C. was continued for 1 h. Orange Loading Dye Solution (5 µL, 0.2% orange G, 0.05% xylene cyanol FF, 60 mM ethylenediaminetetraacetic acid, 60% glycerol, MBI Fermentas) was added to each sample, and aliquots (15 µL) were analyzed for the degree of protection by agarose gel (1%) electrophoresis. Parallel control experiments were performed with phage lambda DNA in the absence of M.HhaI-Q82A/N304A and in the presence of M.HhaI-Q82A/N304A (1100 ng).

The M.HhaI variant Q82A/N304A with the cofactor 10 (FIG. 11, right) leads to almost protected phage lambda DNA. This result demonstrates that an elongated and amino-functionalized side chain can be transferred by M.HhaI-Q82A/N304A provided that the carbon next to the sulfonium center is further activated by a flanking carbon-carbon triple bond (propargylic system).

D. Sequence-Specific Two-Step Labeling of pBR322 Plasmid DNA Using Cofactor 10 and DNA Methyltransferases from Different Classes Sequence-specific labeling of long plasmid DNA was performed by first sequence-specific transfer of the activated 4-(4-aminobutanamido)but-2-ynyl group (Z—R=—CH$_2$C≡CCH$_2$NHCOCH$_2$CH$_2$CH$_2$NH$_2$) from cofactor 10 to pBR322 plasmid DNA using the DNA adenine-N6 methyltransferase M.TaqI and the DNA cytosine-C5 methyltransferase M.HhaI variant Q82A/N304A as catalysts and second reaction of 6-(fluorescein-5(and -6)-carboxamido)hexanoic acid N-hydroxysuccinimidyl ester with the primary amino group of sequence-specifically modified pBR322 plasmid DNA (Scheme 10). Sequence-specificity of DNA labeling was verified by fragmentation of labeled pBR322 plasmid DNA with different restriction endonucleases, separation of the resulting DNA fragments by agarose gel electrophoresis and fluorescence imaging of the agarose gel (FIG. 12).

Scheme 10: Sequence-specific two-step flourescent labeling of DNA according to the present invention.

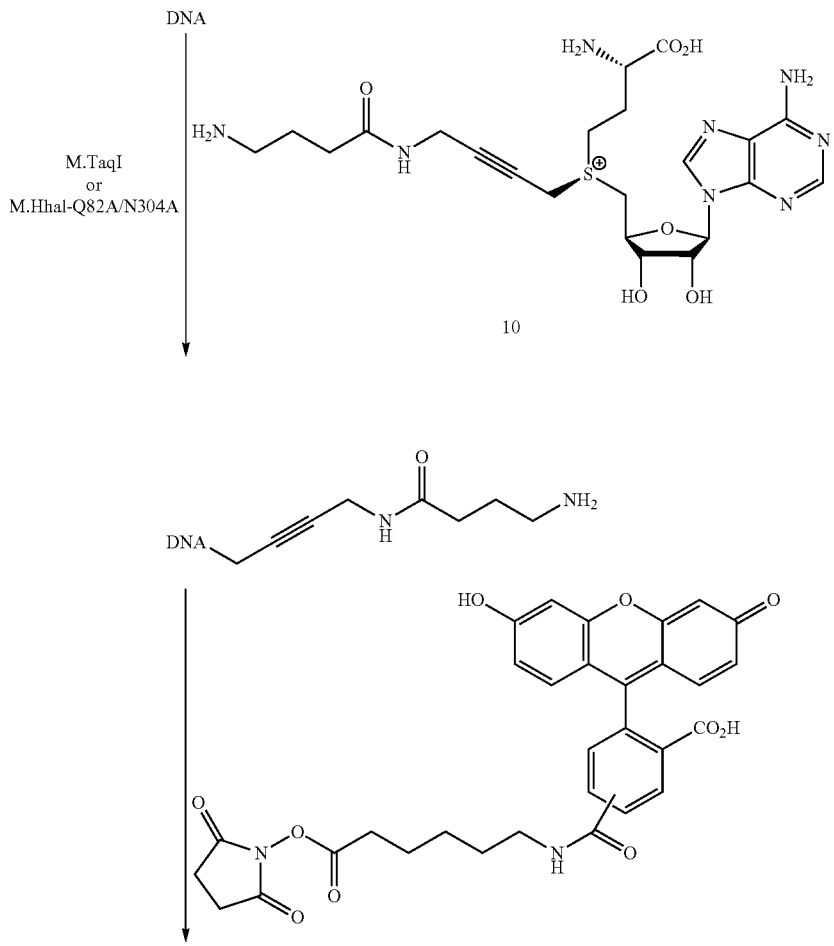

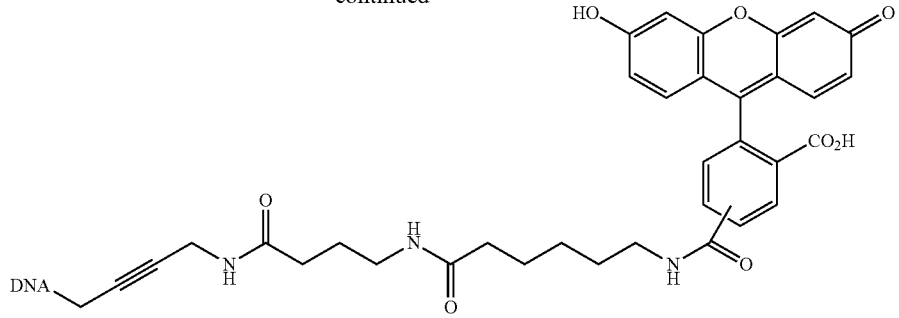

D.1 Sequence-Specific Transfer from Cofactor 10 to 5'-TCGA-3' DNA Sequences in pBR322 Plasmid DNA by the DNA Adenine-N6 Methyltransferase M.TaqI pBR322 plasmid DNA (20.4 µg, 7.14 µmol, 7 5'-TCGA-3' recognition sequences, 50 µmol recognition sequences, MBI Fermentas), M.TaqI (2.39 µg, 50 µmol; produced as described in Goedecke et al., (2001) Nature Struct. Biol. 8, 121-125) and the cofactor analog 10 (300 µM) were incubated in buffer (100 µL, 20 mM Tris acetate, 50 mM potassium acetate, 10 mM magnesium acetate, 1 mM dithiothreitol, and 0.01% Triton X-100 reduced, pH 7.9) at 60° C. for 4 h. Afterwards, the reaction mixture was extracted with a phenol solution (1×100 µL), with a 25:24:1 mixture of phenol solution, chloroform and isoamyl alcohol (1×100 µL) and chloroform (3×100 µL). The aqueous phase was supplemented with sodium acetate (10 µL, 3 M, pH 7.0) and isopropanol (80 µL). The precipitate was collected by centrifugation at 15000 g and room temperature for 15 min. The supernatant was removed and the pellet washed with aqueous ethanol (100 µL, 75%). The pellet was dried and dissolved in water (100 µL).

D.2 Sequence-Specific Transfer from Cofactor 10 to 5'-GCGC-3' DNA Sequences in pBR322 Plasmid DNA by the DNA Cytosine-C5 Methyl-Transferase M.HhaI Variant Q82A/N304A pBR322 plasmid DNA (23.1 µg, 8.06 µmol, 31 5'-GCGC-3' recognition sequence, 250 µmol recognition sequences, MBI Fermentas), M.HhaI variant Q82A/N304A (9.25 µg, 250 µmol; produced as described in Example 4B.2) and the cofactor analog 10 (300 µM) were incubated in buffer (100 µL, 50 mM Tris hydrochloride, 15 mM sodium chloride, 0.5 mM ethylenediaminetetraacetic acid, 2 mM 2-mercaptoethanol, pH 7.4) containing bovine serum albumin (0.2 mg/mL) at 37° C. for 4 h. Afterwards, the reaction mixture was extracted with a phenol solution (1×100 µL), with a 25:24:1 mixture of phenol solution, chloroform and isoamyl alcohol (1×100 µL) and chloroform (3×100 µL). The aqueous phase was supplemented with sodium acetate (10 µL, 3 M, pH 7.0) and isopropanol (80 µL). The precipitate was collected by centrifugation at 15000 g and room temperature for 15 min. The supernatant was removed and the pellet washed with aqueous ethanol (100 µL, 75%). The pellet was dried and dissolved in water (100 µL).

D.3 Fluorescence Labeling of M.TaqI- and M.HhaI-Q82A/N304A-Modified pBR322 plasmid DNA Solutions (90 µL) containing modified pBR322 plasmid DNA from Example 4D.1 or D.2 (40 µL), 6-(fluorescein-5 (and -6)-carboxamido)hexanoic acid N-hydroxysuccinimidyl ester (222 µg, 368 nmol; pre-dissolved in dimethylsufoxide) and sodium hydrogencarbonate (0.15 M, pH 9.0) were incubated in the dark at room temperature for 1 h. Afterwards, the reaction mixtures were passed through NAP5 columns (Amersham Biosciences) and plasmid DNA precipitated by adding isopropanol (4/5 volume). The precipitates were collected by centrifugation at 15000 g and room temperature for 15 min. The supernatants were removed and the pellets washed with aqueous ethanol (2×100 µL, 75%). The pellets were dried and dissolved in water (40 µL).

D.4 Analysis of Fluorescence-Labeled pBR322 Plasmid DNA

Modified pBR322 plasmid DNA from Example 4D.3 (3 µL) was fragmented with different restriction endonucleases or combinations of restriction endonucleases (R.XceI, R.MbiI+R.Eco88I, R.BpiI+R.BseSI, R.BpiI+R.PvuII and R.GsuI, MBI Fermentas) according to the instructions of the manufacturer. Afterwards, a solution (1/5 volume) of proteinase K (2 mg/mL) and sodium dodecyl sulfate (1%) was added to each fragmentation reaction and the samples were incubated at 55° C. for 30 min. Orange Loading Dye Solution (1/6 volume, 0.2% orange G, 0.05% xylene cyanol FF, 60 mM ethylenediaminetetraacetic acid, 60% glycerol, MBI Fermentas) was added to each sample and DNA fragments were separated by agarose gel (1.5%) electrophoresis (10 V/cm) in the absence of ethidium bromide. The agarose gel was scanned with a Fuji gel imaging system FLA-5100 using a 473 nm laser and the LPB filter set (FIG. 12, upper). Afterwards, the agarose gel was stained with ethidium bromide and scanned again for comparison (FIG. 12, upper).

DNA fragments derived from pBR322 modification with M.TaqI which do not contain any M.TaqI recognition sequence were not visible in the absence of ethidium bromide staining (FIG. 12, indicated by white ellipses). In addition, fluorescence intensities of individual DNA fragments correlated well with the number of M.TaqI or M.HhaI recognition sequences in these fragments (Table 5). These results demonstrate that amino-modified DNA obtained with M.TaqI or M.HhaI-Q82A/N304A in the presence of AdoMet analog 10 can be labeled with an N-hydroxysuccinimidyl ester and that labeling is sequence-specific.

TABLE 5

Quantitative fluorescence agarose gel analysis of labeled pBR322 plasmid DNA fragments (compare FIG. 12) obtained after fragmentation with various restriction endonucleases (REases).

| REase(s) | Fragment size/bp | M. TaqI sites number (%) | Rel. fluorescence intensity/% | M. HhaI sites number (%) | Rel. fluorescence intensity/% |
|---|---|---|---|---|---|
| R. Xcel | 2450 | 4 (57) | 62 | 16 (52) | 49 |
|  | 1254 | 3 (43) | 38 | 10 (32) | 32 |
|  | 365 | 0 (0) | — | 4 (13) | 15 |
|  | 292 | 0 (0) | — | 1 (3) | 4 |
| R. Mbil + | 1801 | 2 (29) | 30 | 8 (26) | 24 |
| R. Eco88l | 1579 | 5 (71) | 70 | 15 (48) | 41 |
|  | 981 | 0 (0) | — | 8 (26) | 35 |
| R. Bpil + | 1246 | 1 (14) | 14 | 6 (19) | 18 |
| R. BseSl | 863 | 2 (29) | 29 | 7 (23) | 23 |
|  | 747 | 3 (43) | 43 | 8 (26) | 26 |
|  | 700 | 0 (0) | — | 5 (16) | 16 |
|  | 498 | 1 (14) | 14 | 4 (13) | 14 |
|  | 307 | 0 (0) | — | 1 (3) | 3 |
| R. Bpil + | 2278 | 2 (29) | 33 | 14 (45) | 44 |
| R. Pvull | 863 | 2 (29) | 25 | 8 (26) | 23 |
|  | 747 | 3 (43) | 42 | 7 (23) | 26 |
|  | 473 | 0 (0) | — | 2 (6) | 7 |
| R. Gsul | 1757 | 4 (57) | 53 | 14 (45) | 41 |
|  | 1434 | 1 (14) | 15 | 10 (32) | 31 |
|  | 616 | 0 (0) | — | 4 (13) | 16 |
|  | 554 | 2 (29) | 32 | 3 (10) | 12 |

The invention claimed is:

1. A compound represented by formula (I)

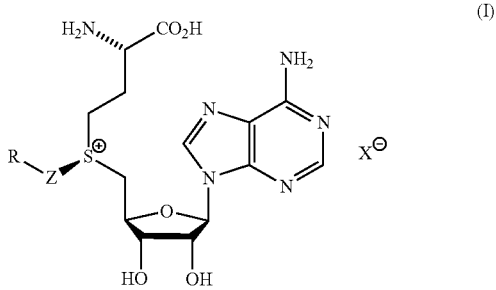

wherein R comprises a carbon-carbon double bond, carbon-sulfur double bond, carbon-nitrogen double bond, -a carbon-carbon triple bond, carbon-nitrogen triple bond or an aromatic carbocyclic or heterocyclic system in β-position to the sulfonium center, $X^\ominus$ is an organic or inorganic anion carrying one or more negative charges, Z is —$CR^1R^2$—, —O—, —S— or —$NR^3$— and $R^1$, $R^2$ and $R^3$ are independently selected from the group consisting of H, D and $C_1$-$C_{12}$ alkyl.

2. The compound of claim 1, wherein Z is —$CR^1R^2$—.

3. The compound of claim 2, wherein $R^1$ and $R^2$ are independently H or D.

4. The compound of claim 1, wherein R comprises —CH═CH—, —C≡C—, or a phenyl group in β-position to the sulfonium center.

5. The compound of claim 1, wherein said organic or inorganic anion is selected from the group consisting of trifluoroacetate, formate, halide and sulfonate.

6. The compound of claim 1, wherein R additionally comprises at least one functional group, a heavy atom or a heavy atom cluster suitable for phasing of X-ray diffraction data, a radioactive or stable rare isotope, or a residue of a member selected from the group consisting of a fluorophore, fluorescence quencher, affinity tag, crosslinking agent, nucleic acid cleaving reagent, spin label, chromophor, protein, peptide or amino acid, nucleotide, nucleoside, nucleic acid, carbohydrate, lipid, transfection reagent, intercalating agent, nanoparticle and bead.

7. The compound of claim 6, wherein R comprises a functional group selected from the group consisting of an amino group, a thiol group, a 1,2-diol group, a hydrazino group, a hydroxyamino group, a haloacetamide group, a maleimide group, an aldehyde group, a ketone group, an 1,2-aminothiol group, an azido group, an alkyne group, a 1,3-diene function, a dienophilic function, an arylhalide group, a terminal alkyne group, an arylboronic acid group, a terminal haloalkyne group, a terminal silylalkyne group, a protected amino group, a protected thiol group, a protected 1,2-diol group, a protected hydrazino group, a protected hydroxyamino group, a protected aldehyde group, a protected ketone group, and a protected 1,2-aminothiol group.

8. The compound of claim 6, wherein R comprises a fluorophore selected from the group consisting of:

an Alexa fluorophore, BODIPY, bimane, coumarin, Cascade blue, dansyl, dapoxyl, fluorescein, mansyl, MANT, Oregon green, pyrene, rhodamine, Texas red, TNS, fluorescent nanocrystals (quantom dots), and a cyanine fluorophore.

9. The compound of claim 6, wherein R comprises a fluorescence quencher selected from the group consisting of: dabcyl, or a compound sold under the trade name of QSY™ or BHQ™.

10. The compound of claim 6, wherein R comprises an affinity tag selected from the group consisting of: peptide tag, metal-chelating group, isotope coded affinity tag, biotin, maltose, mannose, glucose, N-acetylglucosamine, N-acetylneuraminic acid, galactose, N-acetylgalactosamine, digoxygenin or dinitrophenol.

11. The compound of claim 10, wherein said affinity tag is a peptide tag selected from the group consisting of: a his-tag, tag with metal chelating properties, strep-tag, flag-tag, c-myc-tag, HA-tag, epitope or glutathione.

12. The compound of claim 10, wherein said affinity tag is a metal-chelating group selected from the group consisting of: nitrilotriacetic acid, ethylenediaminetetraacetic acid (EDTA), 1,10-phenanthroline, a crown ether or a $His_{4-8}$ peptide.

13. The compound of claim 6, wherein R comprises a crosslinking agent selected from the group consisting of a mono- or bifunctional platinum(II) complex, maleimide, iodoacetamide, aldehyde, and a photocrosslinking agent.

14. The compound of claim 13, wherein said crosslinking agent is a photocrosslinking agent selected from the group consisting of an arylazide, a diazo compound, a 2-nitrophenyl compound, psoralen or a benzophenone compound.

15. The compound of claim 6, wherein R comprises a heavy atom or heavy atom cluster selected from the group consisting of selected from the group consisting of copper, zinc, selenium, bromine, iodine, ruthenium, palladium, cadmium, tungsten, platinum, gold, mercury, bismuth, samarium, europium, terbium, uranium, $Ta_6Br_{14}$, $Fe_4S_4$, and $P_2W_{18}O_{62}$.

16. The compound of claim 6, wherein R comprises a nucleic acid cleaving reagent selected from the group consisting of iron-ethylenediaminetetraacetic acid (iron-EDTA), copper-1,10-phenanthroline, acridine or a derivative thereof, an enediyne compound or a rhodium complex.

17. A complex of a compound of claim 1 and a methyltransferase which is capable of using S-adenosyl-L-methionine as a cofactor.

18. The complex of claim 17, wherein said methyltransferase is capable of transferring a methyl residue of S-adenosyl-L-methionine onto a nucleic acid molecule, a polypeptide, a carbohydrate or a small molecule.

19. The complex of claim 18, wherein said methyltransferase is an orphan DNA methyltransferase or part of a bacterial restriction modification system.

20. The complex of claim 19, wherein the methyltransferase is a DNA methyltransferase selected from the group consisting of M.TaqI, M.HhaI, M.BcnIB (M2.BcnI), M.SssI, M.BseCI, M.RsrI, M2.BfiI (M.BfiC2), and M2.Eco31I.

21. A kit comprising a compound of claim 1, and a suitable container.

22. The kit of claim 21 further comprising a methyltransferase.

23. A kit comprising a complex of claim 17, and a suitable container.

24. A pharmaceutical composition comprising a compound of claim 1, and a pharmaceutically acceptable carrier.

25. A pharmaceutical composition of claim 24 further comprising a methyltransferase.

26. A pharmaceutical composition of claim 25, wherein the compound forms a complex with the methyltransferase.

27. A method for the preparation of a modified target molecule comprising the incubation of the target molecule with a compound of claim 1 in the presence of a methyltransferase which is capable of using the compound as a cofactor and under conditions which allow for the transfer of Z—R onto the target molecule.

28. The method of claim 27, wherein Z—R comprises a label selected from the group consisting of a fluorophore, fluorescence quencher, affinity tag, spin label, radioactive or stable rare isotope, chromophor or a detectable nanoparticle.

29. The method of claim 27, wherein Z—R comprises at least a first functional group group selected from the group consisting of: an amino group, a thiol group, a 1,2-diol group, a hydrazino group, a hydroxyamino group, a haloacetamide group, a maleimide group, an aldehyde group, a ketone group, an 1,2-aminothiol group, an azido group, an alkyne group, a 1,3-diene function, a dienophilic function, an arylhalide group, a terminal alkyne group, an arylboronic acid group, a terminal haloalkyne group, a terminal silylalkyne group, a protected amino group, a protected thiol group, a protected 1,2-diol group, a protected hydrazino group, a protected hydroxyamino group, a protected aldehyde group, a protected ketone group, and a protected 1,2-aminothiol group.

30. The method of claim 29, further comprising the step of reacting the modified target molecule with a label comprising a second functional group, wherein said second functional group is selected from the group consisting of: thiol; primary amine; hydrazine; hydroxylamine; aldehyde; ketone; 1,2-aminothiol; azide; alkyne; diene; dienophile; terminal alkyne; arylhalide; arylboronic acid; terminal haloalkyne; terminal silylalkyne; N-hydroxysuccinimidyl ester; acyl azide; acyl nitrile; acyl chloride; pentafluorophenyl ester; thioester; sulfonyl chloride; isothiocyanate; imidoester; aziridine; and phosphane ester.

31. A method for detecting sequence-specific methylation in a biomolecule, comprising:
    (a) contacting a biomolecule with an S-adenosyl-L-methionine-dependent methyltransferase in the presence of a detectable cofactor of said methyltransferase; and
    (b) detecting whether the recognition site of said methyltransferase has been modified with the cofactor or a derivative thereof, wherein modification of the recognition site of said methyltransferase is indicative of an absence of methylation at said recognition site;
wherein said cofactor is a compound of claim 1.

* * * * *

UNITED STATES PATENT AND TRADEMARK OFFICE
CERTIFICATE OF CORRECTION

| | | |
|---|---|---|
| PATENT NO. | : 8,008,007 B2 | Page 1 of 1 |
| APPLICATION NO. | : 11/871016 | |
| DATED | : August 30, 2011 | |
| INVENTOR(S) | : Elmar Weinhold et al. | |

It is certified that error appears in the above-identified patent and that said Letters Patent is hereby corrected as shown below:

In section (73) Assignees' name should read:

RWTH AACHEN, AACHEN (DE)
--INSTITUTE OF BIOTECHNOLOGY, VILNIUS (LT)--

Signed and Sealed this
Thirteenth Day of December, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 14
<212> TYPE: DNA
<213> ORGANISM: artificial sequence
<220> FEATURE:
<221> NAME/KEY: source
<223> OTHER INFORMATION:
    /note="Description of artificial sequence: as
    shown in example 2A and 4B1"

<400> SEQUENCE: 1
gccgctcgat gccg                                                            14

<210> SEQ ID NO 2
<211> LENGTH: 14
<212> TYPE: DNA
<213> ORGANISM: artificial sequence
<220> FEATURE:
<221> NAME/KEY: source
<223> OTHER INFORMATION: /note="Description of artificial sequence: as
    shown in example 2A and 4B1"
<220> FEATURE:
<221> NAME/KEY: misc_feature
<222> LOCATION: (9)..(9)
<223> OTHER INFORMATION: n = A^Me = N6-methyl-2'-deoxyadenosine

<400> SEQUENCE: 2
cggcatcgng cggc                                                            14

<210> SEQ ID NO 3
<211> LENGTH: 24
<212> TYPE: DNA
<213> ORGANISM: artificial sequence
<220> FEATURE:
<221> NAME/KEY: source
<223> OTHER INFORMATION: /note="Description of artificial sequence: as
    shown in examples 2B, 4B2 and 2C"

```
<400> SEQUENCE: 3
cattacgcgc cgggtcctgg ctat                                               24

<210> SEQ ID NO 4
<211> LENGTH: 24
<212> TYPE: DNA
<213> ORGANISM: artificial sequence
<220> FEATURE:
<221> NAME/KEY: source
<223> OTHER INFORMATION: /note="Description of artificial sequence: as
      shown in example 2B and 4B2"

<400> SEQUENCE: 4
atagccagga cccggcgcgt aatg                                               24
```